(12) United States Patent
Winder

(10) Patent No.: US 9,707,265 B2
(45) Date of Patent: Jul. 18, 2017

(54) TREATMENT OF MUSCULAR DYSTROPHY

(71) Applicant: The University of Sheffield, Sheffield, South Yorkshire (GB)

(72) Inventor: Steven J. Winder, Sheffield (GB)

(*) Notice: Subject to any disclaimer, the term of this patent is extended or adjusted under 35 U.S.C. 154(b) by 63 days.

(21) Appl. No.: 14/414,001

(22) PCT Filed: Jul. 12, 2013

(86) PCT No.: PCT/GB2013/051849
§ 371 (c)(1),
(2) Date: Jan. 9, 2015

(87) PCT Pub. No.: WO2014/009738
PCT Pub. Date: Jan. 16, 2014

(65) Prior Publication Data
US 2015/0343012 A1 Dec. 3, 2015

(30) Foreign Application Priority Data

Jul. 12, 2012 (GB) .................................. 1212456.6

(51) Int. Cl.
| | | |
|---|---|---|
| *A61K 38/07* | (2006.01) | |
| *A61K 31/198* | (2006.01) | |
| *A61K 31/496* | (2006.01) | |
| *A61K 31/506* | (2006.01) | |
| *A61K 31/4155* | (2006.01) | |
| *A61K 31/517* | (2006.01) | |
| *A61K 31/69* | (2006.01) | |
| *G01N 33/50* | (2006.01) | |
| *A61K 38/17* | (2006.01) | |
| *A01K 67/027* | (2006.01) | |

(52) U.S. Cl.
CPC .......... *A61K 38/07* (2013.01); *A01K 67/0275* (2013.01); *A61K 31/198* (2013.01); *A61K 31/4155* (2013.01); *A61K 31/496* (2013.01); *A61K 31/506* (2013.01); *A61K 31/517* (2013.01); *A61K 31/69* (2013.01); *A61K 38/1709* (2013.01); *G01N 33/5041* (2013.01); *A01K 2217/052* (2013.01); *A01K 2217/054* (2013.01); *A01K 2217/15* (2013.01); *A01K 2227/105* (2013.01); *A01K 2267/0306* (2013.01); *G01N 2333/9015* (2013.01); *G01N 2800/10* (2013.01)

(58) Field of Classification Search
None
See application file for complete search history.

(56) References Cited

U.S. PATENT DOCUMENTS

2010/0292306 A1 11/2010 Carlson et al.

FOREIGN PATENT DOCUMENTS

| WO | 0136475 A3 | 5/2001 |
|---|---|---|
| WO | 0211750 A2 | 2/2002 |
| WO | 0211750 A3 | 2/2002 |
| WO | 0229056 A3 | 4/2002 |
| WO | 2006002284 A1 | 1/2006 |
| WO | 2007059356 A2 | 5/2007 |
| WO | 2007059356 A3 | 5/2007 |
| WO | 2011064661 A1 | 6/2011 |
| WO | 2012164234 A1 | 12/2012 |

OTHER PUBLICATIONS

M. James et al., "Adhesion-dependent tyrosine phosphorylation of beta-dystroglycan regulates its interaction with utrophin", Journal of Cell Science, vol. 113, No. 10, May 2000, pp. 1717-1726.
X. Huang et al., "Structure of a WW domain containing fragments of dystrophin in complex with beta-dystroglycan", Nature Structural Biology, vol. 7, No. 8, Aug. 2000, pp. 634-638.
A.V. Pereboev et al., "Epitopes in the interacting regions of beta-dystroglycan (PPxY motif) and dystrophin (WW domain)", Biochimica et Biophysica Acta, vol. 1527, No. 1-2, Jul. 2, 2001, pp. 54-60.
F. Sotgia et al., "Tyrosine phosphorylation of beta-dystroglycan at its WW domain binding motif, PPxY, recruits SH2 domain containing protein", Biochemistry, vol. 40, No. 48, Dec. 4, 2001, pp. 14585-14582.
A.S. Yatsenko et al., "The conserved WW-domain binding sites in Dystroglycan C-terminus are essential but partially redundant for Dystroglycan function", BMC Developmental Biology, vol. 9, No. 1, Feb. 27, 2009, 9 pages.
E. Gazzerro et al., "Therapeutic Potential of Protepsome Inhibition in Duchenne and Becker Muscular Dystropies", American Journal of Pathology, vol. 176, No. 4, Apr. 2010, pp. 1863-1877.
Sarah Allnutt, Authorized Officer, European Patent Office, "International Search Report" in connection with related PCT Patent Application No. PCT/GB2013/051849, dated Jul. 12, 2013, 7 pages.
Sarah Allnutt, Authorized Officer, European Patent Office, "Written Opinion" in connection with related Patent Application No. PCT/GB2013/051849, dated Jul. 12, 2013, 12 pages.
Luise, Monica et al., "Dystrophin is phosphorylated by endogenous protein kinases", Biochemistry Journal, vol. 293, 1993, pp. 243-247.
Muchir, Antoine et al., "Inhibition of extracellular signal-regulated kinase signaling to prevent cardiomyopathy caused by mutation in the gene encodng A-type lamins", Human Molecular Genetics, vol. 18, No. 2, Oct. 16, 2008, pp. 241-247.
Roffe, Suzy et al., "Halofuginone inhibits Smad3 phosphorylation via the PI3K/Akt and MAPK/ERK pathways in muscle cells: Effect on myotube fusion", Experimental Cell Research, vol. 316, Jan. 11, 2010, pp. 1061-1069.
Pines, Mark et al., "Halofuginone and muscular dystrophy", Histology and Histopathology Cellular and Molecular Biology, vol. 26, 2011, pp. 135-146.
Carmignac, Virginie et al., "Autophagy is increased in laminin α2 chain-deficient muscle and its inhibition improves muscle morphology in a mouse model of MDC1A", Human Molecular Genetics, vol. 20, No. 24, Sep. 14, 2011, pp. 4891-4902.

(Continued)

*Primary Examiner* — Christine J Saoud
*Assistant Examiner* — Jon M Lockard
(74) *Attorney, Agent, or Firm* — Kolisch Hartwell, P.C.

(57) ABSTRACT

The invention provides a compound capable of inhibiting ubiquitination for use in treating a disorder or symptom associated with reduced dystroglycan function in a subject.

9 Claims, 31 Drawing Sheets

(56) References Cited

OTHER PUBLICATIONS

Miller, Gaynor et al., "Preventing phosphorylation of dystroglycan ameliorates the dystrophic phenotype in mdx mouse", Human Molecular Genetics, vol. 21, No. 20, Jul. 18, 2012, pp. 4508-4520.
U.K. Intellectual Property Office, "Search Report" in connection with related U.K. Patent Application No. GB1212456.6, dated Nov. 7, 2012, 5 pages.
U.K. Intellectual Property Office, "Search Report" in connection with related U.K. Patent Application No. GB1212456.6, dated Apr. 25, 2013, 6 pages.
U.K. Intellectual Property Office, "Search Report" in connection with related U.K. Patent Application No. GB1212456.6, dated Apr. 25, 2013, 3 pages.

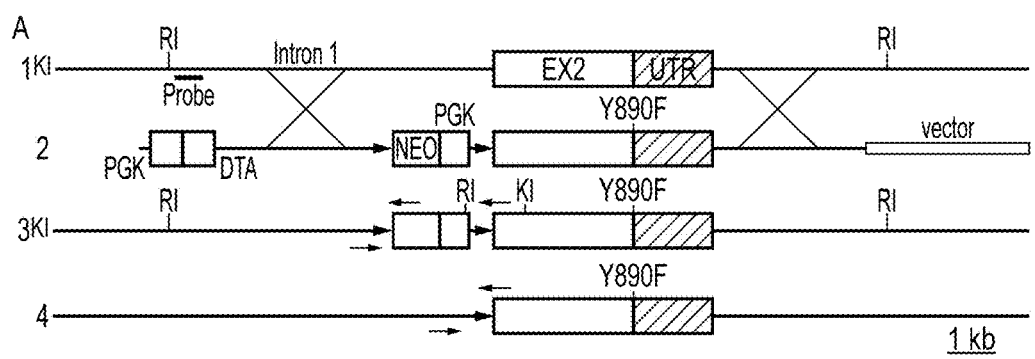
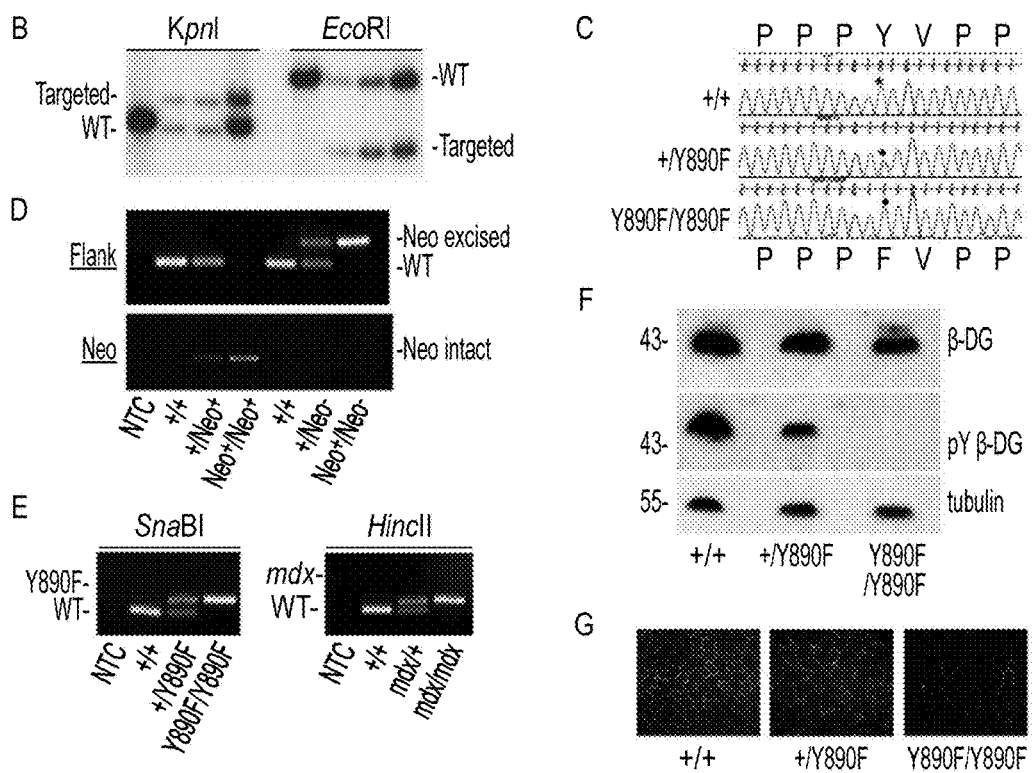
FIG. 1

E13 PKNMTPYRSPPPYVP
E14 KNMTPYRSPPPYVPP
E15 KNMTPYRSPPPpYVPP

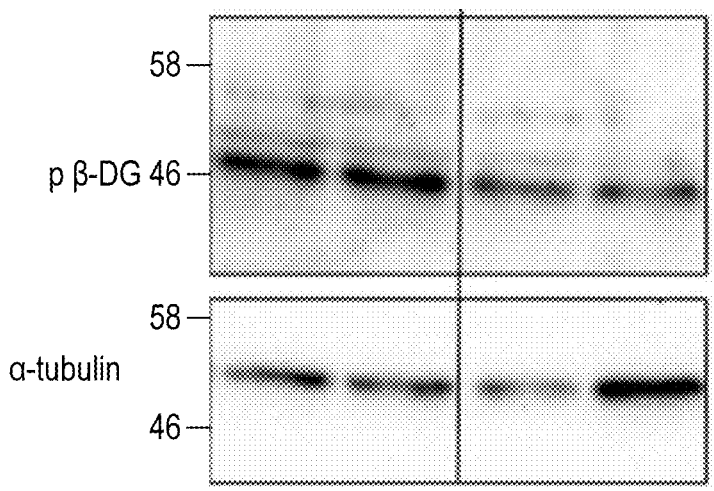
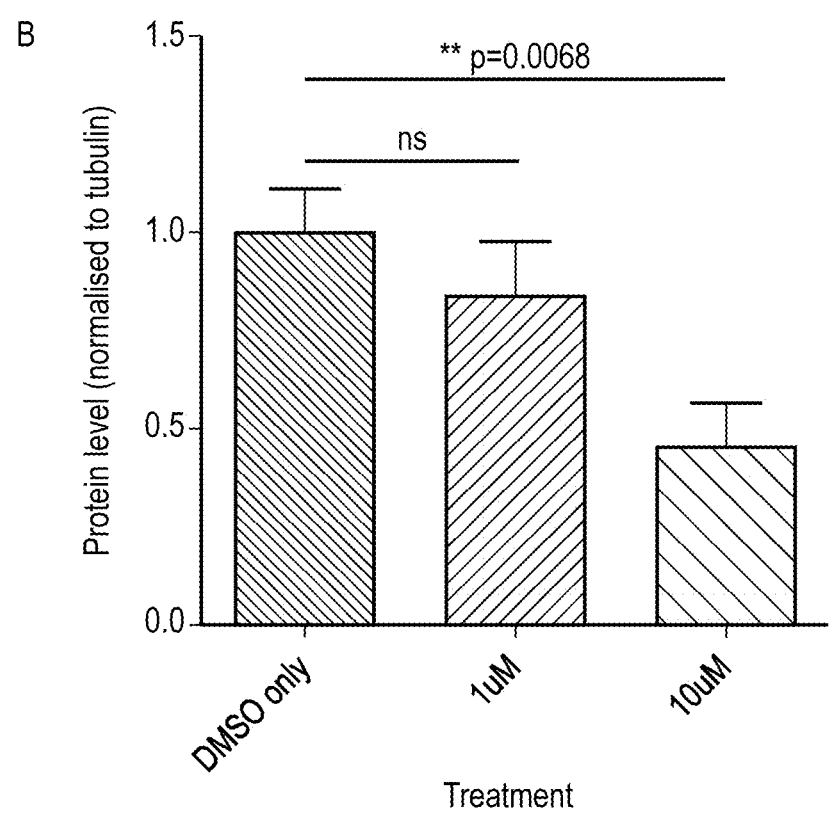
FIG. 13

SEQ ID NO:1

Human Dystroglycan

```
    mrmsvglsll lplwgrtfll llsvvmaqsh wpsepseavr dwenqleasm hsvlsdlhea
 61 vptvvgipdg tavvgrsfrv tiptdliass gdiikvsaag kealpswlhw dsqshtlegl
121 pldtdkgvhy isvsatrlga ngshipqtss vfsievyped hsdlqsvrta spdpgevvss
181 acaadepvtv ltvildadit kmtpkqridl lhrmrsfsev elhnmklvpv vnnrlfdmsa
241 fmagpgnpkk vvengallsw klgcslnqns vpdihgveap aregamsaql gypvvgwhia
301 nkkpplpkrv rrqihatptp vtaigpptta iqeppsrivp tptspaiapp tetmappvrd
361 pvpgkptvti rtrgaiiqtp tlgpiqptrv seagttvpgq irptmtipgy veptavatpp
421 ttttkkprvs tpkpatpstd sttttrrpt kkprtprpvp rvttkvsitr letaspptri
481 rtttsgvprg gepnqrpelk nhidrvdawv gtyfevkips dtfydhedtt tdklkltlkl
541 reqqlvgeks wvqfnsnsql myglpdsshv gkheyfmhat dkgglsavda feihvhrrpq
601 gdraparfka kfvgdpalvl ndihkkialv kklafafgdr ncstitlqni trgsivvewt
661 nntlplepcp keqiaglsrr iaeddgkprp afsnalepdf katsitvtgs gscrhlqfip
721 vvpprrvpse apptevpdrd peksseddvy lhtvipavvv aailliagii amicyrkkrk
781 gkltledqat fikkgvpiif adelddskpp psssmplilq eekaplpppe ypnqsvpett
841 plnqdtmgey tplrdedpna ppyqppppft vpmegkgsrp knmtpyrspp pyvpp
```

FIG. 17

SEQ ID NO:2

Human Dystroglycan Y892F

```
mrmsvglsll lplwgrtfll llsvvmaqsh wpsepseavr dwenqleasm hsvlsdlhea
61  vptvvgipdg tavvqrsfrv tiptdliass gdiikvsaag kealpswlhw dsqshtlegl
121 pldtdkgvhy isvsatrlga ngshipqtss vfsievyped hsdlqsvrta spdpgevvss
181 acaadepvtv ltvildadlt kmtpkqridl lhrmrsfsev elhnmklvpv vnnrlfdmsa
241 fmagpgnpkk vvengallsw klgcslnqns vpdihgveap aregamsaql gypvvgwhia
301 nkkpplpkrv rrqihatptp vtaigpptta iqeppsrivp tptspaiapp tetmappvrd
361 pvpgkptvti rtrgaiiqtp tlgpiqptrv seagttvpgq irptmtipgy veptavatpp
421 ttttkkprvs tpkpatpstd sttttrrpt kkprtprpvp rvttkvsitr letaspptri
481 rtttsgvprg gepnqrpelk nhidrvdawv gtyfevkips dtfydhedtt tdklkltlkl
541 reqqlvgeks wvqfnsnsql myglpdsshv gkheyfmhat dkgglsavda feihvhrrpq
601 gdraparfka kfvgdpalvl ndihkkialv kklafafgdr ncstitlqni trgsivvewt
661 nntlplepcp keqiaglsrr iaeddgkprp afsnalepdf katsitvtgs gscrhlqfip
721 vvpprrvpse apptevpdrd peksseddvy lhtvipavvv aailliagii amicyrkkrk
781 gkltledqat fikkgvpiif adelddskpp psssmplilq eekaplpppe ypnqsvpett
841 plnqdtmgey tplrdedpna ppyqppppft vpmegkgsrp knmtpyrspp pFvpp
```

FIG. 18

SEQ ID NO:3

Mouse Dystroglycan

```
    msvdnwllhp lwgqtfllll svavaqahwp sepseavrdw knqleasmhs vlsdfqeavp
 61 tvvgipdgta vvgrsfrvsi ptdliassge iikvsaagke alpswlhwdp hshileglpl
121 dtdkgvhyis vsaarlgang shvpqtssvf sievypedhn epqsvraass dpgevvpsac
181 aadepvtvlt vildadltkm tpkqridlln rmqsfsevel hnmklvpvvn nrlfdmsafm
241 agpgnakkvv engallswkl gcslnqnsvp dirgvetpar egamsaqlgy pvvgwhiank
301 kptlpkrlrr qihatptpvt aigppttaiq eppsrivptp tspaiappte tmappvrdpv
361 pgkptvtirt rgaiiqtptl gpiqptrvse agttvpgqir ptltipgyve ptavitpptt
421 ttkkprvstp kpatpstdss ttttrrptkk prtprpvprv ttkapitrle taspptrirt
481 ttsqvprgge pnqrpelknh idrvdawvqt yfevkipsdt fydnedtttd klkltlklre
541 qqlvgekswv qfnsnsqlmy glpdsshvgk heyfmhatdk gglsavdafe ihvhkrpqgd
601 kaparfkarl agdpapvvnd ihkkialvkk lafafgdrnc ssitlqnitr gsivvewtnn
661 tlplepcpke qiiglsrria dengkprpaf snalepdfka lsiavtgsgs crhlqfipva
721 ppspgssaap atevpdrdpe ksseddvylh tvipavvvaa illiagiiam icyrkkrkgk
781 ltledqatfi kkgvpiifad elddskppps ssmplilqee kaplpppeyp nqsmpettpl
841 nqdtvgeytp lrdedpnapp yqppppftap megkgsrpkn mtpyrspppy vpp
```

FIG. 19

SEQ ID NO:4

Mouse Dystroglycan Y890F

```
msvdnwllhp lwgqtfllll svavaqahwp sepseavrdw knqleasmhs vlsdfqeavp
61 tvvgipdgta vvgrsfrvsi ptdliassge iikvsaagke alpswlhwdp hshileglpl
121 dtdkgvhyis vsaarlgang shvpqtssvf sievypedhn epqsvraass dpgevvpsac
181 aadepvtvlt vildadltkm tpkqridlln rmqsfsevel hnmklvpvvn nrlfdmsafm
241 agpgnakkvv engallswkl gcsinqnsvp dirgvetpar egamsaqlgy pvvgwhiank
301 kptlpkrlrr qihatptpvt aigppttaiq eppsrivptp tspaiappte tmappvrdpv
361 pgkptvtirt rgaiiqtptl gpiqptrvse agttvpgqir ptltipgyve ptavitpptt
421 ttkkprvstp kpatpstdss ttttrrptkk prtprpvprv ttkapitrle taspptrirt
481 ttsgvprgge pnqrpelknh idrvdawvgt yfevkipsdt fydnedtttd klkltlklre
541 qqlvgekswv qfnsnsqlmy glpdsshvgk heyfmhatdk gglsavdafe ihvhkrpqgd
601 kaparfkarl agdpapvvnd ihkkialvkk lafafgdrnc ssitlqnitr gsivvewtnn
661 tlplepcpke qiiglsrria dengkprpaf snalepdfka lsiavtgsgs crhlqfipva
721 ppspgssaap atevpdrdpe ksseddvylh tvipavvvaa illiagiiam icyrkkrkgk
781 ltledqatfi kkgvpiifad elddskppps ssmplilqee kaplpppeyp nqsmpettpl
841 nqdtvgeytp lrdedpnapp yqppppftap megkgsrpkn mtpyrspppF vpp
```

FIG. 20

SEQ ID NO:5
Human Dystroglycan

```
     gggccagtcg gcgccgcgcg gagctggccg ctggattggc tgcaacactc gcgtgtcagg
  61 cggttgctag gctccggccg cgcgccccgc ccttgcgctc agcgccctct caccgcccgg
 121 tacgtgctcg cgcgaaggct gcggcgcggc gctcgcgcct cttaggcttg gcggtggcgg
 181 cggcggcagc ttcgccgcga atccgccggg agcggcggtg gcggcgtcct ggggccagga
 241 ggagcgaaca cctgcgcgg tcctcccgcc ggcgctggc tctgtgtgct ccggcgatgga
 301 gcaggtgtgc agagggtgag aacccagctc tgggaccaag tcacttgctt ccttacttag
 361 caagactatc gacttgagca aacttggacc tgggatgagg atgtctgtgg gcctctcgct
 421 gctgctgccc ctctggggga ggacctttct cctcctgctc tctgtggtta tggctcagtc
 481 ccactggccc agtgaaccct cagaggctgt cagggactgg gaaaaccagc ttgaggcatc
 541 catgcactca gtgctctcag acctccacga ggctgttccc acagtggttg cattcctga
 601 tggcacggct gtcgtcgggc gctcatttcg agtgaccatt ccaacagatt tgattgcctc
 661 cagtggagat atcatcaagg tatcagccgc agggaaggag gctttgccat cttggctgca
 721 ctgggactca cagagccaca ccctggaggg cctccccctt gacactgata agggtgtgca
 781 ttacatttca gtgagcgcta cacggctggg ggccaacggg agccacatcc cccagacctc
 841 cagtgtgttc tccatcgagg tctaccctga agaccacagt gatctgcagt cggtgaggac
 901 agcctcccca gaccctggtg aggtggtatc atctgcctgt gctgcggatg aacctgtgac
 961 tgttttgacg gtgatttgg atgccgacct caccaagatg acccaaagc aaaggattga
1021 cctcctgcac aggatgcgga gcttctcaga agtagagctt cacaacatga aattagtgcc
1081 ggtggtgaat aacagactat ttgacatgtc ggccttcatg ctggccgcgg gaaatccaaa
1141 aaaggtggtg gagaatgggg ccctctctc ctggaagctg ggctgctccc tgaaccagaa
1201 cagtgtgcct gacattcatg gtgtagaggc ccctgccagg gagggcgcaa tgtctgctca
1261 gcttggctac cctgtggtgg gttggcacat cgccaataag aagccccctc ttcccaaacg
1321 cgtccggagg caqatccatq ctacacccac acctgtcact gccattgggc cccaaccac
1381 ggctatccag gagcccccat ccaggatcgt gccaaccccc acatctccag ccattgctcc
1441 tccaacagag accatggctc ctccagtcag ggatcctgtt cctgggaaac ccacggtcac
1501 catccggact cgaggcgcca ttattcaaac cccaacccta ggccccatcc agcctactcg
1561 ggtgtcagaa gctgcacca cagttcctgg ccagttcgc ccaacgatca ccattcctgg
1621 ctatgtggag cctactcag ttgctacccc tcccacaacc accaccaaga agccacgagt
1681 atccacacca aaaccagcaa cgccttcaac tgactccacc accaccacga ctcgcaggcc
1741 aaccaagaaa ccacggacac cccggccagt gccccgggtc accaccaaag tttccatcac
1801 cagattggaa actgcctcac cgcctactcg tattcgcacc accaccagtg gagtgccccg
1861 tggcggagaa cccaaccagc gcccagagct caagaaccat attgacaggg tagatgcctg
1921 ggttggcacc tactttgagg tgaagatccc gtcagacact ttctatgacc atgaggacac
1981 caccactgac aagctgaagc tgaccctgaa actgcgggag cagcagctgg tgggcgagaa
2041 gtcctggta cagttcaaca gcaacagcca gctcatgtat ggccttcccg acagcagcca
2101 cgtgggcaaa cacgagtatt tcatgcatgc cacagacaag gggggcctgt cggctgtgga
2161 tgccttcgag atccacgtcc acaggcgccc caagggcgat agggctcctg caaggttcaa
2221 ggccaagttt gtgggtgacc cggcactggt gttgaatgac atccacaaga gattgccctt
2281 ggtaaagaaa ctggccttcg cctttggaga ccgaaactgt agcaccatca ccctgcagaa
2341 tatcacccgg ggctccatcg tggtggaatg gaccaacaac acactgccct ggagccctg
2401 ccccaaggag cagatgctg gctgagccg ccggatcgct gaggatgatg gaaaacctcg
2461 gcctgccttc tccaacgccc tagagcctga ctttaaggcc acaagcatca ctgtgacggg
2521 ctctggcagt gtgcggcacc tacagtttat ccctgtggta ccaccagga gagtgccctc
2581 agaggcgccg cccacagaag tgcctgacag ggaccctgag aagagcagtg aggatgatgt
2641 ctacctgcac acagtcattc cggcgtgt ggtcgcagcc atcctgctca ttgctggcat
2701 cattgccatg atctgctacc gcaagaagcg gaagggcaag ttacccttg aggaccagg
2761 caccttcatc aagaagggg tgcctatcat ctttgcagac gaactggacg actccaagcc
2821 cccaccctcc tccagcatgc cactcattct gcaggaggag aaggctcccc tacccctcc
2881 tgagtacccc aaccagagtg tgcccgagac cactcctctg aaccaggaca ccatgggaga
2941 gtacacgccc ctgcgggatg aggatccaaa tgcgcctccc taccagcccc caccgccttt
3001 cacagtaccc atgggggca aggctcccg tcccaagaac atgacccat accggtcacc
3061 tcctcctat gtccaccttg aaccgcaag cgcctggtg gaggcaggt agggcagggc
3121 cctggagacg acatggtgtt gtctgtggag accggtggcc tgcagaccat gcccaccgg
3181 gagccgacac ctgacctagc acacactgac acaggggcct ggacaagccc gccctctctg
3241 gtcctcccaa accccaaagc agctggagag actttgggga cttttttatt ttattttttt
3301 gcctaacagc ttttggtttg ttcatagaga actcttcgct tcattttga tggctggctc
3361 tgaaagcacc atgtggagtg gaggtggagg gaccgaggaa ccatgaatga actcgcaggc
3421 agtgccgggc ggcccctgg ctctctgcgt tttgccttta acactaactg tactgttttt
3481 tctattcacg tgtgtctage tgcaggtaga aacatgagaaa acagtaacta aagattaaat
3541 tcaaaggact ttcagaagtt aaggttaagt ttttacgttt aatctgctgt ttacctaaac
3601 ttgtatgtat aatttttggg tgggtatggg gaattgcttt gctaaaaata agctcccagg
3661 gtgtttcaaa cttagagaag accaagggac agtattttt atcaaaggaa tactattttt
3721 tcacactacg tcaacttggt tgctctgata ccccagagcc tgattggggg cctcccggcc
```

FIG. 21

```
3781 ctggctcacg ccaagtccct ggtgctgggt ttgctctccc gctgttgcca ggggctggaa
3841 gctggagggg tctcttgggc catggacatc cccacttcca gcccatgtac actagtggcc
3901 cacgaccaag gggtcttcat ttccatgaaa aagggactcc aagaggcagt ggtggctgtg
3961 gcccccaact ttggtgctcc agggtgggcc aactgcttgt ggggcacct gggaggtcaa
4021 aggtctccac cacatcaacc tattttgttt tacccttttt ctgtgcattg ttttttttt
4081 tcctcctaaa aggaatatca cggtttttg aaacactcag tgggggacat tttggtgaag
4141 atgcaatatt tttatgtcat gtgatgctct ttcctcactt gaccttggcc gctttgtcct
4201 aacagtccac agtcctgccc cgacccaccc catccttttt ctctggcact ccagtccagc
4261 ttgggcctga actactggaa aaggtctggc ggctggggag gagtgccagc aatagttcat
4321 aataaaaatc tgttagctct caaagctaat tttttactaa agttttata cagcctcaaa
4381 ttgttttatt aaaaaaaaga tttaaaatgg tgatgcttac agcagtttgt acgagctctt
4441 aagtgttgat tccatggaac tgacggcttt gcttgttttg attcttttcc ccctactttt
4501 cctaatggtt taaattctgg aattacactg gggttcttt gccttttta gcagaacatc
4561 cgtccgtcca tctgcatctc tgtcccatga ctcaggggcg cccactctgc ttcgattctc
4621 ctcctgtgga agaaaccatt ttgagcatga cttttcttga tgtctgaagc gttattttgg
4681 gtacttttta gggaggaatg cctttcgcaa taatgtatcc attccctga ttgagggtgg
4741 gtgggtggac ccaggctccc tttgcacaca gagcagctac ttctaagcca tatcgactgt
4801 tttgcagagg atttgtgtgt cctccctcag gaggggaggc ctggtaggag ggggggagag
4861 ttctctgtcc tactgctctc aagagggcat ttccccttgc gccttctccc acagggccca
4921 gcccctctcc cctgcccaag tccccagggg gtactctgga gtgagcagtc ccctgtggg
4981 ggagcctgta aatgcgggct cagtggacca ctggtgactg ggctcatgcc tccaagtcag
5041 agtttcccct ggtgcccag agacaggagc acaagtggga tctgacctgg tgagattatt
5101 tctgatgacc tcatcaaaaa ataaacaatt cccaatgttc caggtgaggg ctttgaaagg
5161 ccttccaaac agctccgtcg ccctagcaa ctccaccatt gggcactgcc atgcagagac
5221 gtggctggcc cagaatggcc tgttgccata gcaactggag gcgatggggc agtgaacaga
5281 ataacaacag caacaatgcc tttgcaggca gcctgctccc ctgagcgctg ggctggtgat
5341 ggccgttgga ctctgtgaga tggagagcca atctcacatt caagtgttca ccaaccactg
5401 atgtgttttt atttccttct atatgatttt aagatgtgtt ttctgcattc tgtaaagaaa
5461 catatcaaac taaataaaag cagtgtcttt att
```

FIG. 21 (continued)

SEQ ID NO:6
Mouse Dystroglycan
```
     ggggctcggg ggcggcagcg gcggtagctt cgcgcggagt cccggggag tggcggcggt
  61 gtccctgggc ccggaggagc gaacacctgc cgcggcctgc ccgtggtgct gggtgagtgc
 121 gcctcccgcc tctgcctccc ggtgcctgcc tgctggggcc gggatccccg ctgcagccga
 181 ccgagcctcc cgcggaacac ctgctgctgc tccctttcgg cccggggcgg ggacacggcc
 241 acggacgtcc ttgcggggcc tgtgctctct aggaagataa ggttttcaac actgcctggc
 301 actggagggt gaggctctgg gtgctctagg atggaacagc tgtgcagagg gtgaggatcc
 361 aaccctggga ccacatcatt tgctttcttc cttagcaact ggtggcttga acaaacacta
 421 gcctggtga ggatgtctgt ggacaactgg ctactgcacc cctctgggg acagaccttt
 481 ctcctcctcc tgtctgtggc tgtggctcag gcccactggc ccagtgaacc ctcagaggct
 541 gtgagggact ggaagaacca gcttgaggcg tccatgcact cagttctctc cgacttccag
 601 gaggctgttc ccaccgtggt tggcattcca gacggtacgg ctgttgtcgg gcgctcattt
 661 cgagtgagca ttccaacgga tttaattgcc tccagtgggg agatcatcaa ggtgtctgca
 721 gcagggaagg aggccttacc gtcttggcta cactgggacc cacacagtca tattttggaa
 781 ggccttcctc ttgacactga taaaggtgtg cattacatct cagtgagtgc tgcacgcctg
 841 ggagccaatg gaagccacgt ccccagact tccagtgtgt tctctatcga ggtctaccct
 901 gaagaccaca atgagccaca gtctgtacgg gcagcctcat cagaccctgg tgaggtagtg
 961 ccatctgcct gtgctgctga tgagccagtg actgtcctta cagtgattct ggatgctgac
1021 ctcaccaaga tgaccccaaa gcaaaggatc gatctgttga acagaatgca gagcttctca
1081 gaagtagaaac ttcacaacat gaagttggtg cctgtagtga ataatagact atttgacatg
1141 tcggccttca tggctggccc aggaaatgca aagaaagtgg tagagaatgg ggctctcctg
1201 tcctggaaac taggctgctc cttgaaccag aatagcgtcc ctgacatccg tggtgtagaa
1261 accctgcta gggagggtgc tatgtctgcc caacttggtt atcctgtggt gggttggcac
1321 attgccaata agaagcccac tctcccaaa cgactccgga ggcagatcca cgccacacct
1381 acacctgtta ctgccattgg acccccaacc acggccattc aggagccacc atcgcggata
1441 gtgcctacgc ctacatctcc agccattgca cctccaacag agaccatggc tcctcctgtc
1501 agggatcctg ttccagggaa gcccacggtc accattcgga cgcgaggtgc cattattcag
1561 accccaactc tgggccctat ccagctact cggctgtcag aagctggtac cacggttcct
1621 ggccagattc gcccaacact gacaattcct ggctatgtag agcccacagc cgttattact
1681 cctccaacaa ctaccacaaa gaagccacga gtgtccacgc caaagccagc aacgccttca
1741 actgattcgt caactaccac aactcggagg ccaaccaaaa aaccacggac accccgacca
1801 gtgccccgag tcaccaccaa agcacccatc accaggttgg agacagcttc cccacccact
1861 cgaatccgta ctaccaccag tggagtgccc cgtgggggag aacctaacca gcggccagag
1921 ctcaagaatc acattgacag ggtagatgcc tgggtgggaa cctattttga ggtaaagatt
1981 ccatcagaatc ccttctatga caatgaggat accactaccg acaagtcaa gctgaccctg
2041 aagcttcgag agcagcagtt agtaggtgag aaatcgtggg ttcagtttaa cagcaacagc
2101 cagctcatgt atggcctgcc tgacagcagc catgtgggaa acatgagta ttttatgcat
2161 gccacagaca aggggggcct ctcgctgtg gatgccttcg agatccatgt tcacaagcgc
2221 ccacaagggg acaaggctcc tgcacggttc aaggccaggc ttgcagggga tccagcaccg
2281 gtggtgaatg acattcacaa gaaaattgct ttggtaaaga gctagcttt gcttttggg
2341 gatcgaaact gcagctccat cacccttcag aacatcactc ggggctctat cgtggtggaa
2401 tggaccaaca acactctgcc cctggagccc tgcccaagg agcagatcat agggctgagc
2461 cgcaggattg ctgatgaaaa tgggaagcct cgtcctgcct tctccaatgc tctggagcct
2521 gactttaagg ctctgagtat tgctgtgacg ggctctggca gttgtcggca cctccagttt
2581 atccctgtgg caccaccctc tcctggaagc tcagctgcac cagccacaga ggttccagac
2641 agggaccccg agaagagcag tgaggacgat gtttacctgc acaccgttat ccagccgtg
2701 gtggtcgcgg ccatcctgct cattgctgga atcattgcta tgatctgcta tcgcaagaag
2761 aggaagggca agctgaccct tgaggaccag gccacctta ttaagaaggg ggtgcctatc
2821 atctttgcgg atgagctgga tgactctaag cccccgcccc ttccagcat gccgctcatc
2881 ttgcaggaag agaaggctcc cctcccacct cctgagtacc ccaaccagag tatgccgag
2941 accactcctc tgaaccagga cactgtggga gagtacacac ccctgcggga tgaggatcct
3001 aacgcacctc cctatcagcc cccccaccc ttcacggctc ccatggaggg caagggctcc
3061 cgtcccaaga acatgaccccc ataccgatca cccctccgt atgttccccc ttaacccaca
3121 agcgctgggg tggaggcagg ggtagggcag gggcctggag acaacttggt gttgtctgta
3181 gagaccggga gcccacaggc agctgacctc tggtccccaa cacctgacct agcacacact
3241 gacaacaggg cctggacaag cccgccctct ctggtcctcc caaaccccaa agctgctgga
3301 gagactttgg gggactttt tattttcatt tttgcctaa cagcttttg tttgttcata
3361 gaaaagtctt cgctgcgttt tttgatggct ctgaagcact gtttgagtag aggtagaagg
3421 agggagcgag gaaccgtgaa tgaactcgca ggcagtgctg ggcggcccca gctctctgca
3481 ttttgccttt aacactaact gtactgtttt ttctattcac gtgtgtctag ctgcaggatg
3541 taacatggaa aacagtagct aaagattaca ttcaaaggac ttcagaaat taaggttaag
3601 tttttacatt taatctgctg tttacctaaa cttgtacgta taattttgg gtgggtatgg
3661 gaaattgctt tgctaaaaat aagatcccag ggtgtttcaa acttagagaa gaccaaggga
3721 cagtattttt tatcaaagga atcctatttt ttcacactat gtcaacttgg ttgctctgat
```

FIG. 22

```
3781 atcccagagc ctgactgagg gcctcctggt cctggctcgg gtgccagggc cctggtgctg
3841 ggttcgctct cccgctgttg ccaggggctg gaagctggag gggcctcttg ggccatggac
3901 atcctgacct ctacccatg cacgctagtg gcctaccacc aaggggtct tcatttctgt
3961 gggaaaggga ctccaaaagg cattggtggc tatggcctcc aacctaggtg ctccaaggtg
4021 ggccagctgc tcgtaggggc acctgggaag gtcgaaggac tccacctcat caacctttct
4081 tttcccttct ctgtggtttg gtttggtttg gttctgttct ttcccttccc tcttaaaagg
4141 aatatcacgg tctttgaaac actcagtggg ggacattttg gtgaagatgc aatatttta
4201 tgtcatgtga tgctctttcc tcacttgacc ttggccactt tgtcccaaca gtccacagcc
4261 ctaccccata taccctgccc ctcttctctg gcgctccagt cctgggccgt gggcctgtgg
4321 ctggggagga gtgccagcaa tagttcatag taaaagtctg tgggctctca aagctaattt
4381 tttactaaag tttttataca gcctcaaatt gtttt
```

FIG. 22 (continued)

SEQ ID NO:27

Mouse Dystroglycan Y890F

```
     ggggctcggg ggcggcagcg gcggtagctt cgcgcggagt ccccggggag tggcggcggt
  61 gtccctgggc ccggaggagc gaacacctgc cgcggcctgc ccgtggtgct ggtgagtgc
 121 gcctcccgcc tctgcctccc ggtgcctgcc tgctgggcc gggatccccg ctgcagccga
 181 ccgagccttc cgcggaacac ctgctgctgc tcccttcgg cccggggcgg ggacacggcc
 241 acggacgtcc ttgcggggcc tgtgctctct aggaagataa ggttttcaac actgcctggc
 301 actggagggt gaggctctgg gtgctctagg atgaacagc tgtgcagagg gtgaggatcc
 361 aaccctggga ccacatcatt tgctttcttc cttagcaact ggtggcttga acaaacacta
 421 gcctgggtga ggatgtctgt ggacaactgg ctactgcacc ccctctgggg acagaccttt
 481 ctcctcctcc tgtctgtggc tgtggctcag gcccactggc ccagtgaacc ctcagaggct
 541 gtgagggact ggaagaacca gcttgaggcg tccatgcact cagttctctc cgacttccag
 601 gaggctgttc ccaccgtggt tggcattcca gacggtacgg ctgttgtcgg gcgctcattt
 661 cgagtgagca ttccaacgga tttaattgcc tccagtgggg agatcatcaa ggtgtctgca
 721 gcagggaagg aggccttacc gtcttggcta cactgggacc cacacagtca tattttggaa
 781 ggccttcctc ttgacactga taaggtgtg cattacatct cagtgagtgc tgcacgcctg
 841 ggagccaatg aagccacgt cccccagact tccagtgtgt tctctatcga ggtctaccct
 901 gaagaccaca atgagccaca gtctgtacgg gcagcctcat cagaccctgg tgaggtagtg
 961 ccatctgcct gtgctgctga tgagccagtg actgtcctta cagtgattct ggatgctgac
1021 ctcaccaaga tgacccccaa gcaaggatc gatctgttga acagaatgca gagcttctca
1081 gaagtagaac ttcacaacat gaagttggtg cctgtagtga ataatagact atttgacatg
1141 tcggccttca tggctggccc aggaaatgca agaaagtgg tagagaatgg ggctctcctg
1201 tcctggaaac taggctgctc cttgaaccag aatagcgtcc ctgacatccg tggtgtagaa
1261 accctgcta gggagggtgc tatgtctgcc caacttggtt atcctgtggt gggttggcac
1321 attgccaata agaagcccac tctcccccaaa cgactccgga ggcagatcca cgccacacct
1381 acacctgtta ctgccattgg acccccaacc acggccattc aggagccacc atcgcggata
1441 gtgcctacgc ctacatctcc agccattgca cctccaacag agaccatggc tcctcctgtc
1501 agggatcctg ttccagggaa gcccacggtc accattcgga cgcgaggtgc cattattcag
1561 accccaactc tgggccctat ccagcctact cgggtgtcag aagctggtac cacggttcct
1621 ggccagattc gcccaacact gacaattcct ggctatgtag agcccacagc cgttattact
1681 cctccaacaa ctaccacaaa gaagccacga gtgtccacgc caaagccagc aacgccttca
1741 actgattcgt caactaccac aactcggagg ccaacaaaa aaccacggac accccgacca
1801 gtgcccgag tcaccaccaa agcaccccatc accaggttgg agacagcttc cccaccccact
1861 cgaatccgta ctaccaccag tggagtgccc cgtggggag aacctaacca gcgccagag
1921 ctcaagaatc acattgacag ggtagatgcc tgggtgggaa cctatttga ggtaaagatt
1981 ccatcagaca ccttctatga caatgaggat accactaccg acaagctcaa gctgacctg
2041 aagcttcgag agcagcagtt agtaggtgag aaatcgtggg ttcagtttaa cagcaacagc
2101 cagctcatgt atggcctgcc tgacagcagc catgtgggaa acatgagta tttatgcat
2161 gccacagaca aaggggcct ctccgctgtg gatgccttcg agatccatgt tcaaaagcgc
2221 ccacaagggg acaaggctcc tgcacggttc aaggccaggc ttgcagggga tccagcaccg
2281 gtggtgaatg acattcacaa gaaaattgct ttggtaaaga gctagcttt tgcttttggg
2341 gatcgaaact gcagctccat caccttcag aacatcactc ggggctctat cgtggtggaa
2401 tggaccaaca acactctgcc cctggagccc tgcccaagg agcagatcat agggctgagc
2461 cgcaggattg ctgatgaaaa tggaagcct cgtcctgcct tctccaatgc tctggagcct
2521 gactttaagg ctctgagtat tgctgtgacg ggctctggca gttgtcggca cctccagttt
2581 atccctgtgg caccaccctc tcctggaagc tcagctgcac cagccacaga ggttccagac
2641 agggaccccg agaagagcag tgaggacgat gtttacctgc acaccgttat cccagccgtg
2701 gtggtcgcgg ccatcctgct cattgctgga atcattgcta tgatctgcta tcgcaagaag
2761 aggaagggca gctgaccct tgaggaccag gccacctta ttaagaaggg ggtgcctatc
2821 atctttgcgg atgagctgga tgactctaag ccccgccct cttccagcat gccgctcatc
2881 ttgcaggaag agaaggctcc cctcccacct cctgagtacc caaccagag tatgcccgag
2941 accactcctc tgaaccagga cactgtggga gagtacacac ccctgcggga tgaggatcct
3001 aacgcaccc cctatcagcc cccccaccctc ccatggaggg caaggggctcc
3061 cgtcccaaga acatgaccc ataccgatcc cccctccgt Ttgttccccc ttaacccaca
3121 agcgcctggg tggaggcagg ggtagggcag gggcctgag acaacttggt gttgtctgta
3181 gagaccggtg gcccacaggc cattgcccac tggtcccaa cacctgacct agcacacact
3241 gacaacaggg cctggacaag cccgcccctct ctggtcctcc caaacccaa agctgctgga
3301 gagactttgg gggactttt tatttcatt ttttgcctaa cagctttttg ttgttcata
3361 gaaaagtctt cgctgcgttt tttgatggct ctgaagcact gtttgagtag aggtagaagg
3421 agggagcgga gaaccgtgaa tgaactgcca ggcagtgctg ggcgcccca gctctctgca
3481 ttttgccttt aacactaact gtactgtttt ttctattcac gtgtgtctag ctgcaggatg
3541 taacatggaa aacagtagct aaagattaca ttcaaaggac tttcagaaat taaggttaag
3601 ttttttacatt taatctgctg tttacctaaa cttgtacgta taattttgg gtgggtatgg
```

FIG. 23

```
3661 gaaattgctt tgctaaaaat aagatcccag ggtgtttcaa acttagagaa gaccaaggga
3721 cagtatttt tatcaaagga atcctatttt ttcacactat gtcaacttgg ttgctctgat
3781 atcccagagc ctgactgagg gcctcctggt cctggctcgg gtgccagggc cctggtgctg
3841 ggttcgctct cccgctgttg ccaggggctg gaagctggag gggcctcttg ggccatggac
3901 atcctgacct ctaccccatg cacgctagtg gcctaccacc aagggggtct tcatttctgt
3961 gggaaaggga ctccaaaagg cattggtggc tatggcctcc aacctaggtg ctccaaggtg
4021 ggccagctgc tcgtaggggc acctgggaag gtcgaaggac tccacctcat caacctttct
4081 tttcccttct ctgtggtttg gtttggtttg gttctgttct ttcccttccc tcttaaaagg
4141 aatatcacgg tctttgaaac actcagtggg ggacattttg gtgaagatgc aatattttta
4201 tgtcatgtga tgctctttcc tcacttgacc ttggccactt tgtcccaaca gtccacagcc
4261 ctaccccata taccctgccc ctcttctctg gcgctccagt cctgggccgt gggcctgtgg
4321 ctggggagga gtgccagcaa tagttcatag taaaagtctg tgggctctca aagctaattt
4381 tttactaaag ttttataca gcctcaaatt gtttt
```

FIG. 23 (continued)

SEQUENCE LISTING

<160> NUMBER OF SEQ ID NOS: 23

<210> SEQ ID NO 1
<211> LENGTH: 895
<212> TYPE: PRT
<213> ORGANISM: Homo sapiens

<400> SEQUENCE: 1

Met Arg Met Ser Val Gly Leu Ser Leu Leu Leu Pro Leu Trp Gly Arg
1               5                   10                  15

Thr Phe Leu Leu Leu Leu Ser Val Val Met Ala Gln Ser His Trp Pro

-continued

```
                20                  25                  30
Ser Glu Pro Ser Glu Ala Val Arg Asp Trp Glu Asn Gln Leu Glu Ala
            35                  40                  45
Ser Met His Ser Val Leu Ser Asp Leu His Glu Ala Val Pro Thr Val
        50                  55                  60
Val Gly Ile Pro Asp Gly Thr Ala Val Val Gly Arg Ser Phe Arg Val
65                  70                  75                  80
Thr Ile Pro Thr Asp Leu Ile Ala Ser Ser Gly Asp Ile Ile Lys Val
                85                  90                  95
Ser Ala Ala Gly Lys Glu Ala Leu Pro Ser Trp Leu His Trp Asp Ser
            100                 105                 110
Gln Ser His Thr Leu Glu Gly Leu Pro Leu Asp Thr Asp Lys Gly Val
        115                 120                 125
His Tyr Ile Ser Val Ser Ala Thr Arg Leu Gly Ala Asn Gly Ser His
130                 135                 140
Ile Pro Gln Thr Ser Ser Val Phe Ser Ile Glu Val Tyr Pro Glu Asp
145                 150                 155                 160
His Ser Asp Leu Gln Ser Val Arg Thr Ala Ser Pro Asp Pro Gly Glu
                165                 170                 175
Val Val Ser Ser Ala Cys Ala Ala Asp Glu Pro Val Thr Val Leu Thr
            180                 185                 190
Val Ile Leu Asp Ala Asp Leu Thr Lys Met Thr Pro Lys Gln Arg Ile
        195                 200                 205
Asp Leu Leu His Arg Met Arg Ser Phe Ser Glu Val Glu Leu His Asn
    210                 215                 220
Met Lys Leu Val Pro Val Val Asn Asn Arg Leu Phe Asp Met Ser Ala
225                 230                 235                 240
Phe Met Ala Gly Pro Gly Asn Pro Lys Lys Val Val Glu Asn Gly Ala
                245                 250                 255
Leu Leu Ser Trp Lys Leu Gly Cys Ser Leu Asn Gln Asn Ser Val Pro
            260                 265                 270
Asp Ile His Gly Val Glu Ala Pro Ala Arg Glu Gly Ala Met Ser Ala
        275                 280                 285
Gln Leu Gly Tyr Pro Val Val Gly Trp His Ile Ala Asn Lys Lys Pro
    290                 295                 300
Pro Leu Pro Lys Arg Val Arg Arg Gln Ile His Ala Thr Pro Thr Pro
305                 310                 315                 320
Val Thr Ala Ile Gly Pro Pro Thr Thr Ala Ile Gln Glu Pro Pro Ser
                325                 330                 335
Arg Ile Val Pro Thr Pro Thr Ser Pro Ala Ile Ala Pro Pro Thr Glu
            340                 345                 350
Thr Met Ala Pro Pro Val Arg Asp Pro Val Pro Gly Lys Pro Thr Val
        355                 360                 365
Thr Ile Arg Thr Arg Gly Ala Ile Ile Gln Thr Pro Thr Leu Gly Pro
    370                 375                 380
Ile Gln Pro Thr Arg Val Ser Glu Ala Gly Thr Thr Val Pro Gly Gln
385                 390                 395                 400
Ile Arg Pro Thr Met Thr Ile Pro Gly Tyr Val Glu Pro Thr Ala Val
                405                 410                 415
Ala Thr Pro Pro Thr Thr Thr Lys Lys Pro Arg Val Ser Thr Pro
            420                 425                 430
Lys Pro Ala Thr Pro Ser Thr Asp Ser Thr Thr Thr Thr Arg Arg
        435                 440                 445
```

-continued

Pro Thr Lys Lys Pro Arg Thr Pro Arg Pro Val Pro Arg Val Thr Thr
    450                 455                 460
Lys Val Ser Ile Thr Arg Leu Glu Thr Ala Ser Pro Pro Thr Arg Ile
465                 470                 475                 480
Arg Thr Thr Thr Ser Gly Val Pro Arg Gly Gly Glu Pro Asn Gln Arg
                485                 490                 495
Pro Glu Leu Lys Asn His Ile Asp Arg Val Asp Ala Trp Val Gly Thr
            500                 505                 510
Tyr Phe Glu Val Lys Ile Pro Ser Asp Thr Phe Tyr Asp His Glu Asp
        515                 520                 525
Thr Thr Thr Asp Lys Leu Lys Leu Thr Leu Lys Leu Arg Glu Gln Gln
    530                 535                 540
Leu Val Gly Glu Lys Ser Trp Val Gln Phe Asn Ser Asn Ser Gln Leu
545                 550                 555                 560
Met Tyr Gly Leu Pro Asp Ser Ser His Val Gly Lys His Glu Tyr Phe
                565                 570                 575
Met His Ala Thr Asp Lys Gly Gly Leu Ser Ala Val Asp Ala Phe Glu
            580                 585                 590
Ile His Val His Arg Arg Pro Gln Gly Asp Arg Ala Pro Ala Arg Phe
        595                 600                 605
Lys Ala Lys Phe Val Gly Asp Pro Ala Leu Val Leu Asn Asp Ile His
    610                 615                 620
Lys Lys Ile Ala Leu Val Lys Lys Leu Ala Phe Ala Phe Gly Asp Arg
625                 630                 635                 640
Asn Cys Ser Thr Ile Thr Leu Gln Asn Ile Thr Arg Gly Ser Ile Val
                645                 650                 655
Val Glu Trp Thr Asn Asn Thr Leu Pro Leu Glu Pro Cys Pro Lys Glu
            660                 665                 670
Gln Ile Ala Gly Leu Ser Arg Arg Ile Ala Glu Asp Asp Gly Lys Pro
        675                 680                 685
Arg Pro Ala Phe Ser Asn Ala Leu Glu Pro Asp Phe Lys Ala Thr Ser
    690                 695                 700
Ile Thr Val Thr Gly Ser Gly Ser Cys Arg His Leu Gln Phe Ile Pro
705                 710                 715                 720
Val Val Pro Pro Arg Arg Val Pro Ser Glu Ala Pro Pro Thr Glu Val
                725                 730                 735
Pro Asp Arg Asp Pro Glu Lys Ser Ser Glu Asp Val Tyr Leu His
            740                 745                 750
Thr Val Ile Pro Ala Val Val Ala Ala Ile Leu Leu Ile Ala Gly
        755                 760                 765
Ile Ile Ala Met Ile Cys Tyr Arg Lys Lys Arg Lys Gly Lys Leu Thr
    770                 775                 780
Leu Glu Asp Gln Ala Thr Phe Ile Lys Lys Gly Val Pro Ile Ile Phe
785                 790                 795                 800
Ala Asp Glu Leu Asp Asp Ser Lys Pro Pro Ser Ser Ser Met Pro
                805                 810                 815
Leu Ile Leu Gln Glu Glu Lys Ala Pro Leu Pro Pro Glu Tyr Pro
            820                 825                 830
Asn Gln Ser Val Pro Glu Thr Thr Pro Leu Asn Gln Asp Thr Met Gly
        835                 840                 845
Glu Tyr Thr Pro Leu Arg Asp Glu Asp Pro Asn Ala Pro Pro Tyr Gln
    850                 855                 860

Pro Pro Pro Phe Thr Val Pro Met Glu Gly Lys Gly Ser Arg Pro
865                 870                 875                 880

Lys Asn Met Thr Pro Tyr Arg Ser Pro Pro Tyr Val Pro
            885                 890                 895

<210> SEQ ID NO 2
<211> LENGTH: 895
<212> TYPE: PRT
<213> ORGANISM: Homo sapiens

<400> SEQUENCE: 2

Met Arg Met Ser Val Gly Leu Ser Leu Leu Pro Leu Trp Gly Arg
1               5                   10                  15

Thr Phe Leu Leu Leu Leu Ser Val Val Met Ala Gln Ser His Trp Pro
                20                  25                  30

Ser Glu Pro Ser Glu Ala Val Arg Asp Trp Glu Asn Gln Leu Glu Ala
            35                  40                  45

Ser Met His Ser Val Leu Ser Asp Leu His Glu Ala Val Pro Thr Val
    50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Asp Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
        195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Pro Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
305                 310                 315                 320

Val Thr Ala Ile Gly Pro Pro Thr Thr Ala Ile Gln Glu Pro Pro Ser
                325                 330                 335

Arg Ile Val Pro Thr Pro Thr Ser Pro Ala Ile Ala Pro Pro Thr Glu
            340                 345                 350

```
Thr Met Ala Pro Pro Val Arg Asp Pro Val Pro Gly Lys Pro Thr Val
            355                 360                 365

Thr Ile Arg Thr Arg Gly Ala Ile Ile Gln Thr Pro Thr Leu Gly Pro
        370                 375                 380

Ile Gln Pro Thr Arg Val Ser Glu Ala Gly Thr Thr Val Pro Gly Gln
385                 390                 395                 400

Ile Arg Pro Thr Met Thr Ile Pro Gly Tyr Val Glu Pro Thr Ala Val
                405                 410                 415

Ala Thr Pro Pro Thr Thr Thr Lys Lys Pro Arg Val Ser Thr Pro
            420                 425                 430

Lys Pro Ala Thr Pro Ser Thr Asp Ser Thr Thr Thr Thr Arg Arg
            435                 440                 445

Pro Thr Lys Lys Pro Arg Thr Pro Arg Pro Val Pro Arg Val Thr Thr
            450                 455                 460

Lys Val Ser Ile Thr Arg Leu Glu Thr Ala Ser Pro Pro Thr Arg Ile
465                 470                 475                 480

Arg Thr Thr Thr Ser Gly Val Pro Arg Gly Gly Glu Pro Asn Gln Arg
                485                 490                 495

Pro Glu Leu Lys Asn His Ile Asp Arg Val Asp Ala Trp Val Gly Thr
            500                 505                 510

Tyr Phe Glu Val Lys Ile Pro Ser Asp Thr Phe Tyr Asp His Glu Asp
            515                 520                 525

Thr Thr Thr Asp Lys Leu Lys Leu Thr Leu Lys Leu Arg Glu Gln Gln
        530                 535                 540

Leu Val Gly Glu Lys Ser Trp Val Gln Phe Asn Ser Asn Ser Gln Leu
545                 550                 555                 560

Met Tyr Gly Leu Pro Asp Ser Ser His Val Gly Lys His Glu Tyr Phe
                565                 570                 575

Met His Ala Thr Asp Lys Gly Gly Leu Ser Ala Val Asp Ala Phe Glu
            580                 585                 590

Ile His Val His Arg Arg Pro Gln Gly Asp Arg Ala Pro Ala Arg Phe
        595                 600                 605

Lys Ala Lys Phe Val Gly Asp Pro Ala Leu Val Leu Asn Asp Ile His
            610                 615                 620

Lys Lys Ile Ala Leu Val Lys Lys Leu Ala Phe Ala Phe Gly Asp Arg
625                 630                 635                 640

Asn Cys Ser Thr Ile Thr Leu Gln Asn Ile Thr Arg Gly Ser Ile Val
                645                 650                 655

Val Glu Trp Thr Asn Asn Thr Leu Pro Leu Glu Pro Cys Pro Lys Glu
            660                 665                 670

Gln Ile Ala Gly Leu Ser Arg Arg Ile Ala Glu Asp Asp Gly Lys Pro
            675                 680                 685

Arg Pro Ala Phe Ser Asn Ala Leu Glu Pro Asp Phe Lys Ala Thr Ser
            690                 695                 700

Ile Thr Val Thr Gly Ser Gly Ser Cys Arg His Leu Gln Phe Ile Pro
705                 710                 715                 720

Val Val Pro Pro Arg Arg Val Pro Ser Glu Ala Pro Pro Thr Glu Val
                725                 730                 735

Pro Asp Arg Asp Pro Glu Lys Ser Ser Glu Asp Asp Val Tyr Leu His
            740                 745                 750

Thr Val Ile Pro Ala Val Val Ala Ala Ile Leu Leu Ile Ala Gly
            755                 760                 765
```

```
Ile Ile Ala Met Ile Cys Tyr Arg Lys Lys Arg Lys Gly Lys Leu Thr
770                 775                 780

Leu Glu Asp Gln Ala Thr Phe Ile Lys Lys Gly Val Pro Ile Ile Phe
785                 790                 795                 800

Ala Asp Glu Leu Asp Asp Ser Lys Pro Pro Ser Ser Ser Met Pro
            805                 810                 815

Leu Ile Leu Gln Glu Glu Lys Ala Pro Leu Pro Pro Glu Tyr Pro
            820                 825                 830

Asn Gln Ser Val Pro Glu Thr Thr Pro Leu Asn Gln Asp Thr Met Gly
            835                 840                 845

Glu Tyr Thr Pro Leu Arg Asp Glu Asp Pro Asn Ala Pro Pro Tyr Gln
850                 855                 860

Pro Pro Pro Pro Phe Thr Val Pro Met Glu Gly Lys Gly Ser Arg Pro
865                 870                 875                 880

Lys Asn Met Thr Pro Tyr Arg Ser Pro Pro Phe Val Pro Pro
            885                 890                 895

<210> SEQ ID NO 3
<211> LENGTH: 892
<212> TYPE: PRT
<213> ORGANISM: Mus musculus

<400> SEQUENCE: 3

Met Ser Val Asp Asn Trp Leu Leu His Pro Leu Trp Gly Gln Thr Phe
1               5                   10                  15

Leu Leu Leu Leu Ser Val Ala Val Ala Gln Ala His Trp Pro Ser Glu
            20                  25                  30

Pro Ser Glu Ala Val Arg Asp Trp Lys Asn Gln Leu Glu Ala Ser Met
        35                  40                  45

His Ser Val Leu Ser Asp Phe Gln Glu Ala Val Pro Thr Val Val Gly
    50                  55                  60

Ile Pro Asp Gly Thr Ala Val Val Gly Arg Ser Phe Arg Val Ser Ile
65                  70                  75                  80

Pro Thr Asp Leu Ile Ala Ser Ser Gly Glu Ile Ile Lys Val Ser Ala
            85                  90                  95

Ala Gly Lys Glu Ala Leu Pro Ser Trp Leu His Trp Asp Pro His Ser
        100                 105                 110

His Ile Leu Glu Gly Leu Pro Leu Asp Thr Asp Lys Gly Val His Tyr
    115                 120                 125

Ile Ser Val Ser Ala Ala Arg Leu Gly Ala Asn Gly Ser His Val Pro
130                 135                 140

Gln Thr Ser Ser Val Phe Ser Ile Glu Val Tyr Pro Glu Asp His Asn
145                 150                 155                 160

Glu Pro Gln Ser Val Arg Ala Ala Ser Ser Asp Pro Gly Glu Val Val
            165                 170                 175

Pro Ser Ala Cys Ala Ala Asp Glu Pro Val Thr Val Leu Thr Val Ile
        180                 185                 190

Leu Asp Ala Asp Leu Thr Lys Met Thr Pro Lys Gln Arg Ile Asp Leu
    195                 200                 205

Leu Asn Arg Met Gln Ser Phe Ser Glu Val Glu Leu His Asn Met Lys
210                 215                 220

Leu Val Pro Val Val Asn Asn Arg Leu Phe Asp Met Ser Ala Phe Met
225                 230                 235                 240

Ala Gly Pro Gly Asn Ala Lys Lys Val Val Glu Asn Gly Ala Leu Leu
            245                 250                 255
```

```
Ser Trp Lys Leu Gly Cys Ser Leu Asn Gln Asn Ser Val Pro Asp Ile
            260                 265                 270

Arg Gly Val Glu Thr Pro Ala Arg Glu Gly Ala Met Ser Ala Gln Leu
            275                 280                 285

Gly Tyr Pro Val Val Gly Trp His Ile Ala Asn Lys Lys Pro Thr Leu
            290                 295                 300

Pro Lys Arg Leu Arg Arg Gln Ile His Ala Thr Pro Thr Pro Val Thr
305                 310                 315                 320

Ala Ile Gly Pro Pro Thr Thr Ala Ile Gln Glu Pro Pro Ser Arg Ile
                325                 330                 335

Val Pro Thr Pro Thr Ser Pro Ala Ile Ala Pro Pro Thr Glu Thr Met
            340                 345                 350

Ala Pro Pro Val Arg Asp Pro Val Pro Gly Lys Pro Thr Val Thr Ile
            355                 360                 365

Arg Thr Arg Gly Ala Ile Ile Gln Thr Pro Thr Leu Gly Pro Ile Gln
370                 375                 380

Pro Thr Arg Val Ser Glu Ala Gly Thr Thr Val Pro Gly Gln Ile Arg
385                 390                 395                 400

Pro Thr Leu Thr Ile Pro Gly Tyr Val Glu Pro Thr Ala Val Ile Thr
                405                 410                 415

Pro Pro Thr Thr Thr Thr Lys Lys Pro Arg Val Ser Thr Pro Lys Pro
                420                 425                 430

Ala Thr Pro Ser Thr Asp Ser Ser Thr Thr Thr Arg Arg Pro Thr
            435                 440                 445

Lys Lys Pro Arg Thr Pro Arg Pro Val Pro Arg Val Thr Thr Lys Ala
            450                 455                 460

Pro Ile Thr Arg Leu Glu Thr Ala Ser Pro Pro Thr Arg Ile Arg Thr
465                 470                 475                 480

Thr Thr Ser Gly Val Pro Arg Gly Gly Glu Pro Asn Gln Arg Pro Glu
                485                 490                 495

Leu Lys Asn His Ile Asp Arg Val Asp Ala Trp Val Gly Thr Tyr Phe
            500                 505                 510

Glu Val Lys Ile Pro Ser Asp Thr Phe Tyr Asp Asn Glu Asp Thr Thr
            515                 520                 525

Thr Asp Lys Leu Lys Leu Thr Leu Lys Leu Arg Glu Gln Gln Leu Val
530                 535                 540

Gly Glu Lys Ser Trp Val Gln Phe Asn Ser Asn Ser Gln Leu Met Tyr
545                 550                 555                 560

Gly Leu Pro Asp Ser Ser His Val Gly Lys His Glu Tyr Phe Met His
                565                 570                 575

Ala Thr Asp Lys Gly Gly Leu Ser Ala Val Asp Ala Phe Glu Ile His
            580                 585                 590

Val His Lys Arg Pro Gln Gly Asp Lys Ala Pro Ala Arg Phe Lys Ala
            595                 600                 605

Arg Leu Ala Gly Asp Pro Ala Pro Val Val Asn Asp Ile His Lys Lys
            610                 615                 620

Ile Ala Leu Val Lys Lys Leu Ala Phe Ala Phe Gly Asp Arg Asn Cys
625                 630                 635                 640

Ser Ser Ile Thr Leu Gln Asn Ile Thr Arg Gly Ser Ile Val Val Glu
                645                 650                 655

Trp Thr Asn Asn Thr Leu Pro Leu Glu Pro Cys Pro Lys Glu Gln Ile
            660                 665                 670
```

```
Ile Gly Leu Ser Arg Arg Ile Ala Asp Glu Asn Gly Lys Pro Arg Pro
            675                 680                 685

Ala Phe Ser Asn Ala Leu Glu Pro Asp Phe Lys Ala Leu Ser Ile Ala
690                 695                 700

Val Thr Gly Ser Gly Ser Cys Arg His Leu Gln Phe Ile Pro Val Ala
705                 710                 715                 720

Pro Pro Ser Pro Gly Ser Ser Ala Ala Pro Ala Thr Glu Val Pro Asp
            725                 730                 735

Arg Asp Pro Glu Lys Ser Ser Glu Asp Val Tyr Leu His Thr Val
            740                 745                 750

Ile Pro Ala Val Val Ala Ala Ile Leu Leu Ile Ala Gly Ile Ile
            755                 760                 765

Ala Met Ile Cys Tyr Arg Lys Lys Arg Lys Gly Lys Leu Thr Leu Glu
770                 775                 780

Asp Gln Ala Thr Phe Ile Lys Lys Gly Val Pro Ile Ile Phe Ala Asp
785                 790                 795                 800

Glu Leu Asp Asp Ser Lys Pro Pro Ser Ser Met Pro Leu Ile
            805                 810                 815

Leu Gln Glu Glu Lys Ala Pro Leu Pro Pro Glu Tyr Pro Asn Gln
            820                 825                 830

Ser Met Pro Glu Thr Thr Pro Leu Asn Gln Asp Thr Val Gly Glu Tyr
835                 840                 845

Thr Pro Leu Arg Asp Glu Asp Pro Asn Ala Pro Pro Tyr Gln Pro Pro
            850                 855                 860

Pro Pro Phe Thr Ala Pro Met Glu Gly Lys Gly Ser Arg Pro Lys Asn
865                 870                 875                 880

Met Thr Pro Tyr Arg Ser Pro Pro Pro Tyr Val Pro
            885                 890

<210> SEQ ID NO 4
<211> LENGTH: 893
<212> TYPE: PRT
<213> ORGANISM: Mus musculus

<400> SEQUENCE: 4

Met Ser Val Asp Asn Trp Leu Leu His Pro Leu Trp Gly Gln Thr Phe
1               5                   10                  15

Leu Leu Leu Leu Ser Val Ala Val Ala Gln Ala His Trp Pro Ser Glu
            20                  25                  30

Pro Ser Glu Ala Val Arg Asp Trp Lys Asn Gln Leu Glu Ala Ser Met
        35                  40                  45

His Ser Val Leu Ser Asp Phe Gln Glu Ala Val Pro Thr Val Val Gly
50                  55                  60

Ile Pro Asp Gly Thr Ala Val Val Gly Arg Ser Phe Arg Val Ser Ile
65                  70                  75                  80

Pro Thr Asp Leu Ile Ala Ser Ser Gly Glu Ile Ile Lys Val Ser Ala
                85                  90                  95

Ala Gly Lys Glu Ala Leu Pro Ser Trp Leu His Trp Asp Pro His Ser
            100                 105                 110

His Ile Leu Glu Gly Leu Pro Leu Asp Thr Asp Lys Gly Val His Tyr
        115                 120                 125

Ile Ser Val Ser Ala Ala Arg Leu Gly Ala Asn Gly Ser His Val Pro
130                 135                 140

Gln Thr Ser Ser Val Phe Ser Ile Glu Val Tyr Pro Glu Asp His Asn
145                 150                 155                 160
```

-continued

```
Glu Pro Gln Ser Val Arg Ala Ala Ser Ser Asp Pro Gly Glu Val Val
                165                 170                 175
Pro Ser Ala Cys Ala Ala Asp Glu Pro Val Thr Val Leu Thr Val Ile
            180                 185                 190
Leu Asp Ala Asp Leu Thr Lys Met Thr Pro Lys Gln Arg Ile Asp Leu
        195                 200                 205
Leu Asn Arg Met Gln Ser Phe Ser Glu Val Glu Leu His Asn Met Lys
    210                 215                 220
Leu Val Pro Val Val Asn Asn Arg Leu Phe Asp Met Ser Ala Phe Met
225                 230                 235                 240
Ala Gly Pro Gly Asn Ala Lys Lys Val Val Glu Asn Gly Ala Leu Leu
                245                 250                 255
Ser Trp Lys Leu Gly Cys Ser Leu Asn Gln Asn Ser Val Pro Asp Ile
            260                 265                 270
Arg Gly Val Glu Thr Pro Ala Arg Glu Gly Ala Met Ser Ala Gln Leu
        275                 280                 285
Gly Tyr Pro Val Val Gly Trp His Ile Ala Asn Lys Lys Pro Thr Leu
    290                 295                 300
Pro Lys Arg Leu Arg Arg Gln Ile His Ala Thr Pro Thr Pro Val Thr
305                 310                 315                 320
Ala Ile Gly Pro Pro Thr Thr Ala Ile Gln Glu Pro Pro Ser Arg Ile
                325                 330                 335
Val Pro Thr Pro Thr Ser Pro Ala Ile Ala Pro Pro Thr Glu Thr Met
            340                 345                 350
Ala Pro Pro Val Arg Asp Pro Val Pro Gly Lys Pro Thr Val Thr Ile
        355                 360                 365
Arg Thr Arg Gly Ala Ile Ile Gln Thr Pro Thr Leu Gly Pro Ile Gln
    370                 375                 380
Pro Thr Arg Val Ser Glu Ala Gly Thr Val Pro Gly Gln Ile Arg
385                 390                 395                 400
Pro Thr Leu Thr Ile Pro Gly Tyr Val Glu Pro Thr Ala Val Ile Thr
                405                 410                 415
Pro Pro Thr Thr Thr Lys Lys Pro Arg Val Ser Thr Pro Lys Pro
            420                 425                 430
Ala Thr Pro Ser Thr Asp Ser Ser Thr Thr Thr Arg Arg Pro Thr
        435                 440                 445
Lys Lys Pro Arg Thr Pro Arg Pro Val Pro Arg Val Thr Lys Ala
    450                 455                 460
Pro Ile Thr Arg Leu Glu Thr Ala Ser Pro Pro Thr Arg Ile Arg Thr
465                 470                 475                 480
Thr Thr Ser Gly Val Pro Arg Gly Gly Glu Pro Asn Gln Arg Pro Glu
                485                 490                 495
Leu Lys Asn His Ile Asp Arg Val Asp Ala Trp Val Gly Thr Tyr Phe
            500                 505                 510
Glu Val Lys Ile Pro Ser Asp Thr Phe Tyr Asp Asn Glu Asp Thr Thr
        515                 520                 525
Thr Asp Lys Leu Lys Leu Thr Leu Lys Leu Arg Glu Gln Gln Leu Val
    530                 535                 540
Gly Glu Lys Ser Trp Val Gln Phe Asn Ser Asn Ser Gln Leu Met Tyr
545                 550                 555                 560
Gly Leu Pro Asp Ser Ser His Val Gly Lys His Glu Tyr Phe Met His
                565                 570                 575
```

Ala Thr Asp Lys Gly Gly Leu Ser Ala Val Asp Ala Phe Glu Ile His
                580                 585                 590

Val His Lys Arg Pro Gln Gly Asp Lys Ala Pro Ala Arg Phe Lys Ala
            595                 600                 605

Arg Leu Ala Gly Asp Pro Ala Pro Val Val Asn Asp Ile His Lys Lys
        610                 615                 620

Ile Ala Leu Val Lys Lys Leu Ala Phe Ala Phe Gly Asp Arg Asn Cys
625                 630                 635                 640

Ser Ser Ile Thr Leu Gln Asn Ile Thr Arg Gly Ser Ile Val Val Glu
                645                 650                 655

Trp Thr Asn Asn Thr Leu Pro Leu Glu Pro Cys Pro Lys Glu Gln Ile
            660                 665                 670

Ile Gly Leu Ser Arg Arg Ile Ala Asp Glu Asn Gly Lys Pro Arg Pro
        675                 680                 685

Ala Phe Ser Asn Ala Leu Glu Pro Asp Phe Lys Ala Leu Ser Ile Ala
690                 695                 700

Val Thr Gly Ser Gly Ser Cys Arg His Leu Gln Phe Ile Pro Val Ala
705                 710                 715                 720

Pro Pro Ser Pro Gly Ser Ser Ala Ala Pro Ala Thr Glu Val Pro Asp
                725                 730                 735

Arg Asp Pro Glu Lys Ser Ser Glu Asp Val Tyr Leu His Thr Val
            740                 745                 750

Ile Pro Ala Val Val Val Ala Ala Ile Leu Leu Ile Ala Gly Ile Ile
        755                 760                 765

Ala Met Ile Cys Tyr Arg Lys Lys Arg Lys Gly Lys Leu Thr Leu Glu
770                 775                 780

Asp Gln Ala Thr Phe Ile Lys Lys Gly Val Pro Ile Ile Phe Ala Asp
785                 790                 795                 800

Glu Leu Asp Asp Ser Lys Pro Pro Ser Ser Met Pro Leu Ile
                805                 810                 815

Leu Gln Glu Glu Lys Ala Pro Leu Pro Pro Glu Tyr Pro Asn Gln
            820                 825                 830

Ser Met Pro Glu Thr Thr Pro Leu Asn Gln Asp Thr Val Gly Glu Tyr
        835                 840                 845

Thr Pro Leu Arg Asp Glu Asp Pro Asn Ala Pro Pro Tyr Gln Pro Pro
850                 855                 860

Pro Pro Phe Thr Ala Pro Met Glu Gly Lys Gly Ser Arg Pro Lys Asn
865                 870                 875                 880

Met Thr Pro Tyr Arg Ser Pro Pro Phe Val Pro Pro
                885                 890

<210> SEQ ID NO 5
<211> LENGTH: 5493
<212> TYPE: DNA
<213> ORGANISM: Homo sapiens

<400> SEQUENCE: 5
gggccagtcg gcgccgcgcg gagctggccg ctggattggc tgcaacactc gcgtgtcagg    60
cggttgctag gctccggccg cgcgccccgc ccttgcgctc agcgccctct caccgcccgg   120
tacgtgctcg cgcgaaggct gcggcgcggc gctcgcgcct cttaggcttg gcggtggcgg   180
cggcggcagc ttcgcgccga atccccgggg agcggcggtg gcggcgtcct ggggccagga   240
ggagcgaaca cctgccgcgg tcctcccgcc ggcgctgggc tctgtgtgct ccggatgga    300 gcaggtgtgc agagggtgag aacccagctc tggaccaag tcacttgctt ccttacttag    360

```
caagactatc gacttgagca aacttggacc tgggatgagg atgtctgtgg gcctctcgct    420
gctgctgccc ctctggggga ggacctttct cctcctgctc tctgtggtta tggctcagtc    480
ccactggccc agtgaaccct cagaggctgt cagggactgg gaaaaccagc ttgaggcatc    540
catgcactca gtgctctcag acctccacga ggctgttccc acagtggttg cattcctga     600 tggcacggct gtcgtcgggc gctcatttcg agtgaccatt ccaacagatt tgattgcctc    660
cagtggagat atcatcaagg tatcagcggc agggaaggag gctttgccat cttggctgca    720
ctgggactca cagagccaca ccctggaggg cctcccccttt gacactgata agggtgtgca   780
ttacatttca gtgagcgcta cacggctggg ggccaacggg agccacatcc cccagacctc    840
cagtgtgttc tccatcgagg tctaccctga agaccacagt gatctgcagt cggtgaggac    900
agcctcccca gaccctggtg aggtggtatc atctgcctgt gctgcggatg aacctgtgac    960
tgttttgacg gtgatttttgg atgccgacct caccaagatg accccaaagc aaaggattga   1020
cctcctgcac aggatgcgga gcttctcaga agtagagctt cacaacatga aattagtgcc    1080
ggtggtgaat aacagactat tgacatgtc ggccttcatg gctggcccgg gaaatccaaa     1140
aaaggtggtg gagaatgggg ccttctctc tggaagctg ggctgctccc tgaaccagaa      1200
cagtgtgcct gacattcatg gtgtagaggc ccctgccagg gagggcgcaa tgtctgctca    1260
gcttggctac cctgtggtgg gttggcacat cgccaataag aagccccctc ttcccaaacg    1320
cgtccggagg cagatccatg ctacacccac acctgtcact gccattgggc ccccaaccac    1380
ggctatccag gagcccccat ccaggatcgt gccaaccccc acatctccag ccattgctcc    1440
tccaacagag accatggctc ctccagtcag ggatcctgtt cctgggaaac ccacggtcac    1500
catccggact cgaggcgcca ttattcaaac cccaacccta ggccccatcc agcctactcg    1560
ggtgtcagaa gctggcacca cagttcctgg ccagattcgc caacgatga ccattcctgg     1620 ctatgtggag cctactgcag ttgctacccc tcccacaacc accaccaaga agccacgagt    1680
atccacacca aaaccagcaa cgccttcaac tgactccacc accaccacga ctcgcaggcc    1740
aaccaagaaa ccacggacac cccggccagt gccccgggtc accaccaaag tttccatcac    1800
cagattggaa actgcctcac cgcctactcg tattcgcacc accaccagtg gagtgccccg    1860
tggcggagaa cccaaccagc gcccagagct caagaaccat attgacaggg tagatgcctg    1920
ggttggcacc tactttgagg tgaagatccc gtcagacact ttctatgacc atgaggacac    1980
caccactgac aagctgaagc tgaccctgaa actgcgggag cagcagctgg tgggcgagaa    2040
gtcctgggta cagttcaaca gcaacagcca gctcatgtat ggccttcccg acagcagcca    2100
cgtgggcaaa cacgagtatt tcatgcatgc cacagacaag gggggcctgt cggctgtgga    2160
tgccttcgag atccacgtcc acaggcgccc caagggggat agggctcctg caaggttcaa    2220
ggccaagttt gtgggtgacc cggcactggt gttgaatgac atccacaaga agattgcctt    2280
ggtaaagaaa ctgccttcg cctttggaga ccgaaactgt agcaccatca ccctgcagaa     2340
tatcacccgg ggctccatcg tggtggaatg gaccaacaac acactgccct ggagccctg    2400 ccccaaggag cagatcgctg ggctgagccg ccggatcgct gaggatgatg gaaaacctcg    2460
gcctgccttc tccaacgccc tagagcctga ctttaaggcc acaagcatca ctgtgacggg    2520
ctctggcagt tgtcggcacc tacagtttat ccctgtggta ccacccagga gagtgccctc    2580
agaggcgccg cccacagaag tgcctgacag ggaccctgag aagagcagtg aggatgatgt    2640
ctacctgcac acagtcattc cggccgtggt ggtcgcagcc atcctgctca ttgctggcat    2700
```

```
cattgccatg atctgctacc gcaagaagcg gaagggcaag cttacccttg aggaccaggc    2760
caccttcatc aagaaggggg tgcctatcat ctttgcagac gaactggacg actccaagcc    2820
cccaccctcc tccagcatgc cactcattct gcaggaggag aaggctcccc taccccctcc    2880
tgagtacccc aaccagagtg tgcccgagac cactcctctg aaccaggaca ccatgggaga    2940
gtacacgccc ctgcgggatg aggatcccaa tgcgcctccc taccagcccc caccgccctt    3000
cacagtaccc atggagggca agggctcccg tcccaagaac atgacccat accggtcacc    3060 tcctccctat gtcccacctt aacccgcaag cgcctgggtg gaggcagggt agggcagggc    3120
cctggagacg acatggtgtt gtctgtggag accggtggcc tgcagaccat gcccaccgg    3180 gagccgacac ctgacctagc acacactgac acaggggcct ggacaagccc gccctctctg    3240
gtcctcccaa accccaaagc agctggagag acttttggga cttttttatt tttatttttt    3300
gcctaacagc ttttggtttg ttcatagaga actcttcgct tcattttga tggctggctc    3360 tgaaagcacc atgtgagtg gaggtggagg accgaggaa ccatgaatga actcgcaggc    3420
agtgccgggc ggcccctgg ctctctgcgt tttgcctta acactaactg tactgttttt    3480
tctattcacg tgtgtctagc tgcaggatgt aacatgaaaa acagtaacta aagattaaat    3540
tcaaaggact ttcagaagtt aaggttaagt ttttacgttt aatctgctgt ttacctaaac    3600
ttgtatgtat aattttggg tgggtatggg gaattgcttt gctaaaaata agctcccagg    3660
gtgtttcaaa cttagagaag accaaggac agtatttttt atcaaggaa tactattttt    3720 tcacactacg tcaacttggt tgctctgata ccccagagcc tgattggggg cctcccggcc    3780
ctggctcacg ccaagtccct ggtgctgggt ttgctctccc gctgttgcca ggggctggaa    3840
gctggagggg tctcttgggc catggacatc cccacttcca gcccatgtac actagtggcc    3900
cacgaccaag gggtcttcat ttccatgaaa aagggactcc aagaggcagt ggtggctgtg    3960
gcccccaact ttggtgctcc agggtgggcc aactgcttgt gggggcacct gggaggtcaa    4020
aggtctccac cacatcaacc tattttgttt taccctttt ctgtgcattg ttttttttt    4080 tcctcctaaa aggaatatca cggttttttg aaacactcag tgggggacat tttggtgaag    4140
atgcaatatt tttatgtcat gtgatgctct ttcctcactt gaccttggcc gctttgtcct    4200
aacagtccac agtcctgccc cgacccaccc catccctttt ctctggcact ccagtccagc    4260
ttgggcctga actactggaa aaggtctggc ggctggggag gagtgccagc aatagttcat    4320
aataaaaatc tgttagctct caaagctaat ttttactaa agttttata cagcctcaaa    4380 ttgttttatt aaaaaaaaga tttaaaatgg tgatgcttac agcagtttgt acgagctctt    4440
aagtgttgat tccatggaac tgacggcttt gcttgttttg attcttttcc ccctacttt    4500 cctaatggtt taaattctgg aattacactg gggttctttt gcctttttta gcagaacatc    4560
cgtccgtcca tctgcatctc tgtcccatga ctcaggggcg cccactctgc ttcgattctc    4620
ctcctgtgga agaaaccatt ttgagcatga cttttcttga tgtctgaagc gttattttgg    4680 gtactttta gggaggaatg cctttcgcaa taatgtatcc attccctga ttgagggtgg    4740 gtgggtggac ccaggctccc tttgcacaca gagcagctac ttctaagcca tatcgactgt    4800
tttgcagagg atttgtgtgt cctccctcag gaggggaggc ctggtaggag ggggggagag    4860
ttctctgtcc tactgctctc aagagggcat ttccccttgc gccttctccc acagggccca    4920
gcccctctcc cctgcccaag tcccaggggg gtactctgga gtgagcagtc cccctgtggg    4980
ggagcctgta aatgcgggct cagtggacca ctggtgactg ggctcatgcc tccaagtcag    5040
agtttcccct ggtgccccag agacaggagc acaagtggga tctgacctgg tgagattatt    5100
```

```
tctgatgacc tcatcaaaaa ataaacaatt cccaatgttc caggtgaggg ctttgaaagg    5160
ccttccaaac agctccgtcg cccctagcaa ctccaccatt gggcactgcc atgcagagac    5220
gtggctggcc cagaatggcc tgttgccata gcaactggag gcgatggggc agtgaacaga    5280
ataacaacag caacaatgcc tttgcaggca gcctgctccc ctgagcgctg ggctggtgat    5340
ggccgttgga ctctgtgaga tggagagcca atctcacatt caagtgttca ccaaccactg    5400
atgtgttttt atttccttct atatgatttt aagatgtgtt ttctgcattc tgtaaagaaa    5460
catatcaaac taaataaaag cagtgtcttt att                                  5493

<210> SEQ ID NO 6
<211> LENGTH: 4415
<212> TYPE: DNA
<213> ORGANISM: Mus musculus

<400> SEQUENCE: 6
ggggctcggg ggcggcagcg gcggtagctt cgcgcggagt ccccggggag tggcggcggt      60
gtccctgggc ccggaggagc gaacacctgc cgcggcctgc ccgtggtgct gggtgagtgc     120
gcctcccgcc tctgcctccc ggtgcctgcc tgctggggcc gggatccccg ctgcagccga     180
ccgagccttc cgcggaacac ctgctgctgc tcccttttcgg ccggggcgg ggacacggcc     240 acggacgtcc ttgcggggcc tgtgctctct aggaagataa ggttttcaac actgcctggc     300
actggagggt gaggctctgg gtgctctagg atggaacagc tgtgcagagg gtgaggatcc     360
aaccctggga ccacatcatt tgctttcttc cttagcaact ggtggcttga acaaacacta     420
gcctgggtga ggatgtctgt ggacaactgg ctactgcacc ccctctgggg acagaccttt     480
ctcctcctcc tgtctgtggc tgtggctcag gcccactggc ccagtgaacc tcagaggct      540 gtgagggact ggaagaacca gcttgaggcg tccatgcact cagttctctc cgacttccag     600
gaggctgttc ccaccgtggt tggcattcca gacggtacgg ctgttgtcgg gcgctcattt     660
cgagtgagca ttccaacgga tttaattgcc tccagtgggg agatcatcaa ggtgtctgca     720
gcagggaagg aggccttacc gtcttggcta cactgggacc cacacagtca tattttggaa     780
ggccttcctc ttgacactga taaaggtgtg cattacatct cagtgagtgc tgcacgcctg     840
ggagccaatg gaagccacgt cccccagact tccagtgtgt tctctatcga ggtctaccct     900
gaagaccaca atgagccaca gtctgtacgg gcagcctcat cagaccctgg tgaggtagtg     960
ccatctgcct gtgctgctga tgagccagtg actgtcctta cagtgattct ggatgctgac    1020
ctcaccaaga tgaccccaaa gcaaaggatc gatctgttga acagaatgca gagcttctca    1080
gaagtagaac ttcacaacat gaagttggtg cctgtagtga ataatagact atttgacatg    1140
tcggccttca tggctggccc aggaaatgca aagaaagtgg tagagaatgg gctctcctg    1200 tcctggaaac taggctgctc cttgaaccag aatagcgtcc ctgacatccg tggtgtagaa    1260 accccctgcta gggagggtgc tatgtctgcc caacttggtt atcctgtggt gggttggcac    1320
attgccaata agaagcccac tctccccaaa cgactccgga ggcagatcca cgccacacct    1380
acacctgtta ctgccattgg accccaacc acggccattc aggagccacc atcgcggata    1440
gtgcctacgc ctacatctcc agccattgca cctccaacag agaccatggc tcctcctgtc    1500
agggatcctg ttccagggaa gcccacggtc accattcgga cgcgaggtgc cattattcag    1560
accccaactc tgggccctat ccagcctact cgggtgtcag aagctggtac cacggttcct    1620
ggccagattc gcccaacact gacaattcct ggctatgtag agcccacagc cgttattact    1680
```

```
cctccaacaa ctaccacaaa gaagccacga gtgtccacgc caaagccagc aacgccttca   1740
actgattcgt caactaccac aactcggagg ccaaccaaaa aaccacggac accccgacca   1800
gtgccccgag tcaccaccaa agcacccatc accaggttgg agacagcttc cccacccact   1860
cgaatccgta ctaccaccag tggagtgccc cgtgggggag aacctaacca gcggccagag   1920
ctcaagaatc acattgacag ggtagatgcc tgggtgggaa cctattttga ggtaaagatt   1980
ccatcagaca ccttctatga caatgaggat accactaccg acaagctcaa gctgaccctg   2040
aagcttcgag agcagcagtt agtaggtgag aaatcgtggg ttcagtttaa cagcaacagc   2100
cagctcatgt atggcctgcc tgacagcagc catgtgggaa acatgagta tttatgcat    2160
gccacagaca aagggggcct ctccgctgtg gatgccttcg agatccatgt tcacaagcgc   2220
ccacaagggg acaaggctcc tgcacggttc aaggccaggc ttgcagggga tccagcaccg   2280
gtggtgaatg acattcacaa gaaaattgct ttggtaaaga agctagcttt tgcttttggg   2340
gatcgaaact gcagctccat caccctcag aacatcactc ggggctctat cgtggtggaa   2400
tggaccaaca acactctgcc cctggagccc tgccccaagg agcagatcat agggctgagc   2460
cgcaggattg ctgatgaaaa tgggaagcct cgtcctgcct tctccaatgc tctggagcct   2520
gactttaagg ctctgagtat tgctgtgacg ggctctggca gttgtcggca cctccagttt   2580
atccctgtgg caccaccctc tcctggaagc tcagctgcac cagccacaga ggttccagac   2640
agggaccccg agaagagcag tgaggacgat gtttacctgc acaccgttat cccagccgtg   2700
gtggtcgcgg ccatcctgct cattgctgga atcattgcta tgatctgcta tcgcaagaag   2760
aggaagggca agctgaccct tgaggaccag gccacccttta ttaagaaggg ggtgcctatc   2820
atctttgcgg atgagctgga tgactctaag cccccgccct cttccagcat gccgctcatc   2880
ttgcaggaag agaaggctcc cctcccacct cctgagtacc ccaaccagag tatgcccgag   2940
accactcctc tgaaccagga cactgtggga gagtacacac cctgcgggga tgaggatcct   3000
aacgcacctc cctatcagcc accccaccc ttcacggctc ccatggaggg caagggctcc   3060
cgtcccaaga acatgacccc ataccgatca cccctccgt atgttccccc ttaacccaca   3120
agcgcctggg tggaggcagg ggtagggcag gggcctggag acaacttggt gttgtctgta   3180
gagaccggtg gccacaggc cattgcccac tggtccccaa cacctgacct agcacacact   3240
gacaacaggg cctggacaag cccgccctct ctggtcctcc caaacccaa agctgctgga   3300
gagactttgg gggactttt tatttcatt ttttgcctaa cagcttttg tttgttcata    3360
gaaaagtctt cgctgcgttt tttgatggct ctgaagcact gtttgagtag aggtagaagg   3420
agggagcgag gaaccgtgaa tgaactcgca ggcagtgctg ggcggcccca gctctctgca   3480
ttttgccttt aacactaact gtactgtttt ttctattcac gtgtgtctag ctgcaggatg   3540
taacatggaa aacagtagct aaagattaca ttcaaaggac tttcagaaat taaggttaag   3600
ttttacatt taatctgctg tttacctaaa cttgtacgta taattttgg gtgggtatgg    3660
gaaattgctt tgctaaaaat aagatcccag ggtgtttcaa acttagagaa gaccaaggga   3720
cagtatttt tatcaaagga atcctatttt ttcacactat gtcaacttgg ttgctctgat   3780
atcccagagc ctgactgagg gcctcctggt cctggctcgg gtgccagggc cctggtgctg   3840
ggttcgctct cccgctgttg ccaggggctg gaagctggag gggcctcttg gccatggac    3900
atcctgacct ctaccccatg cacgctagtg gcctaccacc aaggggtct tcatttctgt    3960
gggaaaggga ctccaaaagg cattggtggc tatggcctcc aacctaggtg ctccaaggtg   4020
ggccagctgc tcgtagggc acctgggaag gtcgaaggac tccacctcat caacctttct   4080
```

```
tttcccttct ctgtggtttg gtttggtttg gttctgttct ttcccttccc tcttaaaagg    4140
aatatcacgg tctttgaaac actcagtggg ggacattttg gtgaagatgc aatattttta    4200
tgtcatgtga tgctctttcc tcacttgacc ttggccactt tgtcccaaca gtccacagcc    4260
ctaccccata taccctgccc ctcttctctg gcgctccagt cctgggccgt gggcctgtgg    4320
ctggggagga gtgccagcaa tagttcatag taaaagtctg tgggctctca aagctaattt    4380
tttactaaag tttttataca gcctcaaatt gtttt                               4415

<210> SEQ ID NO 7
<211> LENGTH: 4415
<212> TYPE: DNA
<213> ORGANISM: Mus musculus

<400> SEQUENCE: 7
ggggctcggg ggcggcagcg gcggtagctt cgcgcggagt ccccggggag tggcggcggt      60
gtccctgggc ccggaggagc gaacacctgc cgcggcctgc ccgtggtgct gggtgagtgc     120
gcctcccgcc tctgcctccc ggtgcctgcc tgctggggcc gggatccccg ctgcagccga     180
ccgagccttc cgcggaacac ctgctgctgc tcccttccgg ccccggggcgg ggacacggcc     240
acggacgtcc ttgcggggcc tgtgctctct aggaagataa ggttttcaac actgcctggc     300
actggagggt gaggctctgg gtgctctagg atggaacagc tgtgcagagg gtgaggatcc     360
aaccctggga ccacatcatt tgctttcttc cttagcaact ggtggcttga acaaacacta     420
gcctgggtga ggatgtctgt ggacaactgg ctactgcacc ccctctgggg acagaccttt     480
ctcctcctcc tgtctgtggc tgtggctcag gcccactggc ccagtgaacc ctcagaggct     540
gtgagggact ggaagaacca gcttgaggcg tccatgcact cagttctctc cgacttccag     600
gaggctgttc ccaccgtggt tggcattcca gacggtacgg ctgttgtcgg gcgctcattt     660
cgagtgagca ttccaacgga tttaattgcc tccagtgggg agatcatcaa ggtgctgca      720
gcagggaagg aggccttacc gtcttggcta cactgggacc cacacagtca tattttggaa     780
ggccttcctc ttgacactga taaaggtgtg cattacatct cagtgagtgc tgcacgcctg     840
ggagccaatg gaagccacgt cccccagact tccagtgtgt tctctatcga ggtctaccct     900
gaagaccaca atgagccaca gtctgtacgg gcagcctcat cagaccctgg tgaggtagtg     960
ccatctgcct gtgctgctga tgagccagtg actgtcctta cagtgattct ggatgctgac    1020
ctcaccaaga tgaccccaaa gcaaaggatc gatctgttga acagaatgca gagcttctca    1080
gaagtagaac ttcacaacat gaagttggtg cctgtagtga ataatagact atttgacatg    1140
tcggccttca tggctggccc aggaaatgca agaaagtgg tagagaatgg ggctctcctg    1200
tcctggaaac taggctgctc cttgaaccag aatagcgtcc ctgacatccg tggtgtagaa    1260
accctgcta ggggaggtgc tatgtctgcc caacttggtt atcctgtggt gggttggcac    1320
attgccaata agaagcccac tctccccaaa cgactccgga ggcagatcca cgccacacct    1380
acacctgtta ctgccattgg accccaacc acggccattc aggagccacc atcgcggata    1440
gtgcctacgc ctacatctcc agccattgca cctccaacag agaccatggc tcctcctgtc    1500
agggatcctg ttcagggaa gcccacggtc accattcgga cgcgaggtgc cattattcag    1560
accccaactc tgggccctat ccagcctact cgggtgtcag aagctggtac cacggttcct    1620
ggccagattc gcccaacact gacaattcct ggctatgtag agcccacagc cgttattact    1680
cctccaacaa ctaccacaaa gaagccacga gtgtccacgc caaagccagc aacgccttca    1740
```

-continued

```
actgattcgt caactaccac aactcggagg ccaaccaaaa aaccacggac accccgacca    1800
gtgcccgag tcaccaccaa agcacccatc accaggttgg agacagcttc cccacccact    1860
cgaatccgta ctaccaccag tggagtgccc cgtgggggag aacctaacca gcggccagag   1920
ctcaagaatc acattgacag ggtagatgcc tgggtgggaa cctattttga ggtaaagatt   1980
ccatcagaca ccttctatga caatgaggat accactaccg acaagctcaa gctgaccctg   2040
aagcttcgag agcagcagtt agtaggtgag aaatcgtggg ttcagtttaa cagcaacagc   2100
cagctcatgt atggcctgcc tgacagcagc catgtgggaa acatgagta tttatgcat    2160
gccacagaca aagggggcct ctccgctgtg gatgccttcg agatccatgt tcacaagcgc   2220
ccacaagggg acaaggctcc tgcacggttc aaggccaggc ttgcagggga tccagcaccg   2280
gtggtgaatg acattcacaa gaaaattgct ttggtaaaga agctagcttt tgcttttggg   2340
gatcgaaact gcagctccat cacccttcag aacatcactc ggggctctat cgtggtggaa   2400
tggaccaaca acactctgcc cctggagccc tgccccaagg agcagatcat agggctgagc   2460
cgcaggattg ctgatgaaaa tgggaagcct cgtcctgcct tctccaatgc tctggagcct   2520
gactttaagg ctctgagtat tgctgtgacg ggctctggca gttgtcggca cctccagttt   2580
atccctgtgg caccaccctc tcctggaagc tcagctgcac cagccacaga ggttccagac   2640
agggaccccg agaagagcag tgaggacgat gtttacctgc acaccgttat cccagccgtg   2700
gtggtcgcgc ccatcctgct cattgctgga atcattgcta tgatctgcta tcgcaagaag   2760
aggaagggca agctgaccct tgaggaccag gccaccttta ttaagaaggg ggtgcctatc   2820
atctttgcgg atgagctgga tgactctaag cccccgccct cttccagcat gccgctcatc   2880
ttgcaggaag agaaggctcc cctcccacct cctgagtacc ccaaccagag tatgcccgag   2940
accactcctc tgaaccagga cactgtggga gagtacacac ccctgcggga tgaggatcct   3000
aacgcacctc cctatcagcc accccacccc ttcacggctc ccatggaggg caagggctcc   3060
cgtcccaaga catgacccc ataccgatca cccctccgt ttgttcccc ttaacccaca     3120
agcgcctggg tggaggcagg ggtagggcag gggcctggag acaacttggt gttgtctgta   3180
gagaccggtg gccacaggc cattgcccac tggtccccaa cacctgacct agcacacact    3240
gacaacaggg cctggacaag cccgccctct ctggtcctcc caaacccaa agctgctgga    3300
gagactttgg gggactttt tattttcatt tttgcctaa cagcttttg tttgttcata     3360
gaaaagtctt cgctgcgttt tttgatggct ctgaagcact gtttgagtag aggtagaagg   3420
agggagcgag gaaccgtgaa tgaactcgca ggcagtgctg gcggccccca gctctctgca   3480
ttttgccttt aacactaact gtactgtttt ttctattcac gtgtgtctag ctgcaggatg   3540
taacatggaa aacagtagct aaagattaca ttcaaaggac tttcagaaat taaggttaag   3600
tttttacatt taatctgctg tttacctaaa cttgtacgta taatttttgg gtgggtatgg   3660
gaaattgctt tgctaaaaat aagatcccag ggtgtttcaa acttagagaa gaccaaggga   3720
cagtattttt tatcaaagga atcctatttt ttcacactat gtcaacttgg ttgctctgat   3780
atcccagagc ctgactgagg gcctcctggt cctggctcgg gtgccagggc cctggtgctg   3840
ggttcgctct cccgctgttg ccaggggctg gaagctggag gggcctcttg gccatggac    3900
atcctgacct ctaccccatg cacgctagtg gcctaccacc aagggggtct tcatttctgt   3960
gggaaaggga ctccaaaagg cattggtggc tatggcctcc aacctaggtg ctccaaggtg   4020
ggccagctgc tcgtaggggc acctgggaag gtcgaaggca tccacctcat caacctttct   4080
tttcccttct ctgtggtttg gtttggtttg gttctgttct ttcccttccc tcttaaaagg   4140
```

-continued

```
aatatcacgg tctttgaaac actcagtggg ggacattttg gtgaagatgc aatattttta    4200
tgtcatgtga tgctctttcc tcacttgacc ttggccactt tgtcccaaca gtccacagcc    4260
ctaccccata taccctgccc ctcttctctg gcgctccagt cctgggccgt gggcctgtgg    4320
ctggggagga gtgccagcaa tagttcatag taaaagtctg tgggctctca aagctaattt    4380
tttactaaag tttttataca gcctcaaatt gtttt                               4415
```

<210> SEQ ID NO 8
<211> LENGTH: 31
<212> TYPE: DNA
<213> ORGANISM: Artificial Sequence
<220> FEATURE:
<223> OTHER INFORMATION: Y890F substitution forward primer

<400> SEQUENCE: 8

```
ataccgatca ccccctccgt tgttcccccc t                                      31
```

<210> SEQ ID NO 9
<211> LENGTH: 30
<212> TYPE: DNA
<213> ORGANISM: Artificial Sequence
<220> FEATURE:
<223> OTHER INFORMATION: Y890F substitution reverse primer

<400> SEQUENCE: 9

```
acggaggggg tgatcggtat ggggtcatgt                                        30
```

<210> SEQ ID NO 10
<211> LENGTH: 31
<212> TYPE: DNA
<213> ORGANISM: Artificial Sequence
<220> FEATURE:
<223> OTHER INFORMATION: Phospho-glycerate Kinase (PGK) neomycin
      resistance selection cassette forward primer

<400> SEQUENCE: 10

```
taggatccat aacttcgtat aatgtatgct a                                      31
```

<210> SEQ ID NO 11
<211> LENGTH: 31
<212> TYPE: DNA
<213> ORGANISM: Artificial Sequence
<220> FEATURE:
<223> OTHER INFORMATION: phospho-glycerate kinase (pgk) neomycin
      resistance selection cassette reverse primer

<400> SEQUENCE: 11

```
taggatccat aacttcgtat agcatacatt a                                      31
```

<210> SEQ ID NO 12
<211> LENGTH: 26
<212> TYPE: DNA
<213> ORGANISM: Artificial Sequence
<220> FEATURE:
<223> OTHER INFORMATION: PGK diphtheria toxin A (DTA) cassette forward
      primer

<400> SEQUENCE: 12

```
tactcgagga cctgcagccc aagcta                                            26
```

<210> SEQ ID NO 13
<211> LENGTH: 30
<212> TYPE: DNA
<213> ORGANISM: Artificial Sequence

```
<220> FEATURE:
<223> OTHER INFORMATION: PGK diphtheria toxin A (DTA) cassette reverse
      primer

<400> SEQUENCE: 13
tagttaactg tccaattatg tcacaccaca                                    30

<210> SEQ ID NO 14
<211> LENGTH: 20
<212> TYPE: DNA
<213> ORGANISM: Artificial Sequence
<220> FEATURE:
<223> OTHER INFORMATION: Forward Primer

<400> SEQUENCE: 14
atgagttgga tttcccagca                                               20

<210> SEQ ID NO 15
<211> LENGTH: 20
<212> TYPE: DNA
<213> ORGANISM: Artificial Sequence
<220> FEATURE:
<223> OTHER INFORMATION: Reverse Primer

<400> SEQUENCE: 15
atggcctggc ctaaaatgat                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse Primer

<400> SEQUENCE: 16
atcgccttct atcgccttct                                               20

<210> SEQ ID NO 17
<211> LENGTH: 20
<212> TYPE: DNA
<213> ORGANISM: Artificial Sequence
<220> FEATURE:
<223> OTHER INFORMATION: Dag1 Forward Primer

<400> SEQUENCE: 17
ataccgatca ccccctacgt                                               20

<210> SEQ ID NO 18
<211> LENGTH: 19
<212> TYPE: DNA
<213> ORGANISM: Artificial Sequence
<220> FEATURE:
<223> OTHER INFORMATION: Dag1 Reverse Primer

<400> SEQUENCE: 18
cggtctctac agacaacac                                                19

<210> SEQ ID NO 19
<211> LENGTH: 22
<212> TYPE: DNA
<213> ORGANISM: Artificial Sequence
<220> FEATURE:
<223> OTHER INFORMATION: Dmd Forward Primer

<400> SEQUENCE: 19
gcaaagttct ttgaaaggtc aa                                            22
```

```
<210> SEQ ID NO 20
<211> LENGTH: 20
<212> TYPE: DNA
<213> ORGANISM: Artificial Sequence
<220> FEATURE:
<223> OTHER INFORMATION: Dmd Reverse Primer

<400> SEQUENCE: 20
caccaactgg gaggaaagtt                                              20

<210> SEQ ID NO 21
<211> LENGTH: 15
<212> TYPE: PRT
<213> ORGANISM: Artificial Sequence
<220> FEATURE:
<223> OTHER INFORMATION: E13

<400> SEQUENCE: 21

Pro Lys Asn Met Thr Pro Tyr Arg Ser Pro Pro Pro Tyr Val Pro
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: E14

<400> SEQUENCE: 22

Lys Asn Met Thr Pro Tyr Arg Ser Pro Pro Tyr Val Pro Pro
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: E15

<400> SEQUENCE: 23

Lys Asn Met Thr Pro Tyr Arg Ser Pro Pro Pro Tyr Val Pro Pro
1               5                   10                  15
```

TREATMENT OF MUSCULAR DYSTROPHY

The present invention relates to compounds and compound combinations for use in treating a disorder or symptom associated with reduced dystroglycan function in a subject. Methods for identifying agents useful in the treatment of such disorders or symptoms are also provided. The invention also provides a method for inhibiting degradation of β-dystroglycan, a mutant form of β-dystroglycan with the related nucleic acid molecules, vectors, plasmids and antibodies.

BACKGROUND

Muscular Dystrophy (MD) is a group of muscle disorders in which muscle fibers are unusually susceptible to damage. As a result, defects in muscle proteins accumulate, death of muscle cells and tissue occurs and the musculoskeletal system of affected individuals becomes progressively weaker. Nine major types of muscular dystrophy have been identified; Duchenne, Becker, limb-girdle, congenital, facioscapulohumeral, mytonic, oculopharyngeal, distal and Emery-Dreifuss muscular dystrophy. Several muscular dystrophy-like conditions have also been identified.

In normal striated muscle dystrophin associates with a large group of proteins known as the dystrophin glycoprotein complex (DGC) (1). The DGC serves to stabilise the sarcolemma by making regularly spaced connections between the muscle fibre cytoskeleton and extracellular matrix—part of the costameric cell adhesion complex (2). At the core of this cell adhesion complex is the adhesion receptor dystroglycan which binds laminin in the extracellular matrix and dystrophin on the cytoplasmic face (3). However, in a number of disorders, including the muscular dystrophies, generation of functional dystrophin protein and/or functional DGC is impaired.

Like many cell adhesion complexes, the DGC also has associated signalling activity. Tyrosine phosphorylation of dystroglycan has been identified as an important regulatory event in controlling the interaction between dystrophin and dystroglycan, and therefore plays an important role in maintaining the integrity of the DGC (4). Previous studies have shown that inhibition of the proteasome is able to restore other DGC components in both mdx mice that lack dystrophin and in explants of DMD patients (8, 9).

Duchenne muscular dystrophy (DMD) is a severe muscle wasting disease that affects approximately 1 in 3,500 male births and for which there is currently no cure or effective treatment. Various molecular genetic approaches to combat DMD have been devised but are unlikely to address the need of all DMD sufferers: gene replacement using a number of delivery methods, compensatory gene upregulation and cell based therapies have all met with some success in the laboratory but have failed for a variety of reasons to translate to the clinic (Pichavant. C, et al. Mol Ther, 2011). More recently, however, significant successes have been achieved using exon skipping approaches to splice out mutated parts of the DMD gene and restore some functional dystrophin gene (Kinali. M, et al Lancet Neurol., 2009. 8: 918). This is a rapidly developing area with phase II clinical trials of exon skipping in progress. These approaches provide real hope for the approximately 25% of DMD patients with no effective treatment. Clearly a therapeutic approach that could be effective for all DMD sufferers is still needed. Ideally, there is a need for a small molecule treatment which is simple to administer, does not require customisation to a particular individual, and is well tolerated with a good safety profile. Such a treatment does not currently exist.

BRIEF SUMMARY OF THE DISCLOSURE

The invention is based on the surprising finding that crossing an mdx mouse with a β-dystroglycan knock-in mouse (Dag1$^{Y890F/Y890F}$, with a tyrosine to phenylalanine substitution at residue 890 of dystroglycan), where dystroglycan cannot be phosphorylated at residue 890, results in a significant improvement in pathophysiology.

In a first aspect, the invention provides a compound capable of inhibiting ubiquitination for use in treating a disorder or symptom associated with reduced dystroglycan function in a subject. Preferably, the compound is capable of inhibiting ubiquitination of β-dystroglycan.

In a further aspect, the invention provides a compound capable of inhibiting tyrosine phosphorylation for use in treating a disorder or a symptom associated with reduced dystroglycan function in a subject.

Preferably, the compound is capable of inhibiting tyrosine phosphorylation of β-dystroglycan. More preferably, the compound is capable of inhibiting tyrosine phosphorylation of a PPxY domain of β-dystroglycan. More preferably, when the subject is a human, the compound is capable of inhibiting tyrosine phosphorylation of amino acid residue Y892.

In a further aspect, the invention provides a compound capable of inhibiting ubiquitination for use in treating a disorder or symptom associated with reduced dystroglycan function in a subject in combination with at least one compound selected from a proteasomal inhibitor and a compound capable of inhibiting phosphorylation.

In a further aspect, the invention provides a compound capable of inhibiting phosphorylation for use in treating a disorder or symptom associated with reduced dystroglycan function in a subject in combination with at least one compound selected from a proteasomal inhibitor and a compound capable of inhibiting ubiquitination.

In a further aspect, the invention provides a proteasomal inhibitor for use in treating a disorder or symptom associated with reduced dystroglycan function in a subject in combination with at least one compound selected from a compound capable of inhibiting ubiquitination and a compound capable of inhibiting phosphorylation.

In a further aspect, the invention provides a combination of a compound capable of inhibiting ubiquitination and at least one compound selected from a proteasomal inhibitor and a compound capable of inhibiting phosphorylation for use in treating a disorder or symptom associated with reduced dystroglycan function in a subject.

In a further aspect, the invention provides a combination of a compound capable of inhibiting phosphorylation and a proteasomal inhibitor for use in treating a disorder or symptom associated with reduced dystroglycan function in a subject.

Preferably, and in accordance with any aspect of the invention, the compound capable of inhibiting ubiquitination is a ubiquitination inhibitor.

Preferably, and in accordance with any aspect of the invention, the compound capable of inhibiting phosphorylation is a tyrosine kinase inhibitor.

Preferably, and in accordance with any aspect of the invention, the disorder is a muscular dystrophy. More preferably, the muscular dystrophy is selected from the group consisting of Duchenne Muscular Dystrophy, Limb Girdle Muscular Dystrophy, Congenital Muscular Dystrophy and Becker Muscular Dystrophy.

Preferably, the Limb Girdle Muscular Dystrophy is selected from the group consisting of Limb Girdle Muscular Dystrophy 2C, Limb Girdle Muscular Dystrophy 2D, Limb Girdle Muscular Dystrophy 2E, and Limb Girdle Muscular Dystrophy 2F.

Preferably, the Congenital Muscular Dystrophy is selected from MDC1A, MDC1B, MDC1D, Fukuyama CMD (FCMD), Muscle eye brain disease (MEB) and Walker Warburg Syndrome (WWS).

Preferably, and in accordance with any aspect of the invention, the symptom is selected from the group consisting of muscle weakness or degeneration, calf hypertrophy, reduced myofibre integrity, elevated serum creatine kinase levels, loss of dystrophin and dystrophin associated proteins, and central nucleation of muscle fibres.

Preferably, and in accordance with any aspect of the invention, the ubiquitination inhibitor is a ubiquitin E1 inhibitor. More preferably, the ubiquitin E1 inhibitor is Pyr-41.

Preferably, and in accordance with any aspect of the invention, the tyrosine kinase inhibitor is an Src family tyrosine kinase inhibitor. More preferably, the Src family tyrosine kinase inhibitor is selected from the group consisting of dasatimib, bosutinib and sracatinib.

Preferably, and in accordance with any aspect of the invention, the proteasomal inhibitor is selected from MG132, MG-115, ALLN, Carfilzomib and bortezomib.

In a further aspect, the invention provides a method for inhibiting degradation of β-dystroglycan, wherein the method includes a step of exposing at least one cell comprising β-dystroglycan to at least one of: (i) a compound capable of inhibiting ubiquitination; and (ii) a compound capable of inhibiting phosphorylation. Preferably, the method is an in vivo method. Alternatively, the method is an in vitro method.

Preferably, the compound is capable of inhibiting ubiquitination of β-dystroglycan.

Alternatively, but also preferably, the compound is capable of inhibiting phosphorylation of β-dystroglycan. Preferably, the compound is capable of inhibiting phosphorylation of a PPxY domain of β-dystroglycan.

Preferably, the at least one cell comprises human β-dystroglycan and the compound is capable of inhibiting phosphorylation of amino acid residue Y892.

Preferably, the method of the invention further comprises a step of exposing the cell to a proteasomal inhibitor.

In a further aspect, the invention provides a β-dystroglycan polypeptide comprising a mutated PPxY domain, wherein the mutated PPxY domain is incapable of undergoing tyrosine phosphorylation.

Preferably, the tyrosine is substituted with an amino acid that is incapable of undergoing phosphorylation. More preferably, the tyrosine is substituted with phenylalanine.

Preferably, the β-dystroglycan polypeptide is a human polypeptide. More preferably, the human polypeptide has an amino acid sequence that is at least 80% identical to SEQ ID NO: 1. Most preferably, the polypeptide consists of the amino acid sequence of SEQ ID NO: 2.

Alternatively, the β-dystroglycan polypeptide is a mouse polypeptide. Preferably, the mouse polypeptide has an amino acid sequence that is at least 80% identical to SEQ ID NO: 3. More preferably, the polypeptide consists of the amino acid sequence of SEQ ID NO:4.

In a further aspect, the invention provides a nucleic acid molecule that encodes the β-dystroglycan polypeptide of the invention.

In a further aspect, the invention provides a plasmid or vector comprising the nucleic acid of the invention.

In a further aspect, the invention provides a recombinant cell comprising the plasmid or vector of the invention.

In a further aspect, the invention provides an antibody or antibody fragment that specifically binds to the mutated β-dystroglycan polypeptide of the invention and does not bind to a wildtype β-dystroglycan polypeptide.

Preferably, the antibody or antibody fragment of the invention is a monoclonal antibody, a humanised antibody, a chimeric antibody or a single chain antibody, or an epitope binding fragment thereof.

In a further aspect, the invention provides for the use of an antibody that specifically binds to a PPxY domain of a wildtype β-dystroglycan polypeptide wherein the tyrosine amino acid of the PPxY domain is unphosphorylated for inhibiting degradation of a β-dystroglycan polypeptide.

In a further aspect, the invention provides an antibody that specifically binds to a PPxY domain of a wildtype β-dystroglycan polypeptide wherein the tyrosine amino acid of the PPxY domain is unphosphorylated for use in treating a disorder or symptom associated with reduced dystroglycan function in a subject.

In a further aspect, the invention provides a method for identifying an agent useful in the treatment of a disorder or symptom associated with reduced β-dystroglycan function, the method comprising the steps of:
  (i) contacting a candidate agent to be tested with at least one cell expressing β-dystroglycan;
  (ii) determining the effect of the agent on β-dystroglycan ubiquitination in the at least one cell,
wherein an agent that decreases or inhibits β-dystroglycan ubiquitination is identified as an agent that is useful in the treatment of a disorder or symptom associated with reduced β-dystroglycan function.

Preferably, the at least one cell is treated with a tyrosine phosphatase inhibitor.

In a further aspect, the invention provides a method for identifying an agent useful in the treatment of a disorder or symptom associated with reduced β-dystroglycan function, the method comprising the steps of:
(i) contacting a candidate agent to be tested with at least one cell expressing β-dystroglycan;
(ii) determining the effect of the agent on phosphorylation of a PPxY domain in β-dystroglycan in the at least one cell,
wherein an agent that decreases or inhibits phosphorylation of the PPxY domain of β-dystroglycan is identified as an agent that is useful in the treatment of a disorder or symptom associated with reduced β-dystroglycan function.

In a further aspect, the invention provides for the use of an agent identified by the methods of the invention to inhibit degradation of β-dystroglycan.

In a further aspect, the invention provides an agent identified by the method of the invention for use in treating a disorder or symptom associated with reduced dystroglycan function in a subject.

In a further aspect, the invention provides a transgenic non-human animal which expresses the β-dystroglycan polypeptide of the invention. Preferably, the transgenic non-human animal is a mouse.

Preferably, the mouse is a mdx mouse.

Alternatively, the mouse is a null model of alpha-sarcoglycan, beta-sarcoglycan, delta-sarcoglycan and gamma-sarcoglycan.

Preferably, the transgenic non-human animal is homozygous for the β-dystroglycan polypeptide of the invention.

BRIEF DESCRIPTION OF THE DRAWINGS

Embodiments of the invention are further described hereinafter with reference to the accompanying drawings:

FIG. 1. Illustrates generation of a Dag1$^{Y890F}$ targeting construct. 1A) is a schematic representation of the targeting construct and genomic locus. Restriction sites for Southern blotting are shown KI=KpnI and EI=EcoRI. Flank and Neo PCR primers used to determine whether the neomycin resistance cassette (PGK Neo) has been excised are represented by arrows. LoxP sites flanking PGK Neo are depicted by arrowheads. The location of the probe used for Southern blotting is indicated. Scalebar=1 kb. 1B) is a representative Southern Blot of restriction digested genomic DNA from four different ES cell clones probed with the probe indicated in A. Whether the band corresponds to a wild-type allele or a targeted allele is indicated. 1C) presents chromatograms of sequences from progeny with the genotypes indicated on the left, the A to T point mutation corresponding to Y890F is indicated with an asterisk. 1D) is a 2% agarose gel electrophoresis of PCR products from the Neo and Flank PCRs used to determine the presence or absence of the neomycin resistance cassette, the genotype of the DNA used as a template is shown on the bottom: +=wild-type allele, neo$^-$=an allele with the neomycin cassette excised; neo$^+$=an allele with the neomycin cassette intact, NTC=the no template control. 1E) is a 3.5% agarose gel electrophoresis of SnaBI and HincII digested PCR products used to genotype progeny for the Y890F and mdx point mutations respectively, genotypes of the samples are shown beneath. 1F shows western blotting of quadriceps femoris samples from wildtype (+/+), heterozygote (+/Y890F) and homozygote (Y890F/Y890F) mice using antibodies against non-phosphorylated β-dystroglycan (β-DG), tyrosine phosphorylated β-DG (pY β-DG) and tubulin as a loading control. 1G shows representative immunofluorescence localisation of tyrosine phosphorylated β-DG in sections of quadriceps femoris from wildtype (+/+), heterozygote (+/Y890F) and homozygote (Y890F/Y890F) mice.

Immunofluorescence localisation to the sarcolemma of the DGC components: β- and β-dystroglycan; β-sarcoglycan; sarcospan; dystrophin and utrophin, was unaltered in Dag1$^{Y890F/Y890F}$ mice. As expected all DGC components were significantly lost from the sarcolemma of mdx muscle, where laminin localisation was unaltered and utrophin showed an increased extra-synaptic localisation. In Dag1$^{Y890F/Y890F}$/mdx mice however, there was a clear restoration of all DGC components examined, even in the absence of dystrophin, but with a concomitant loss of utrophin staining from the sarcolemma.

Figure 4:
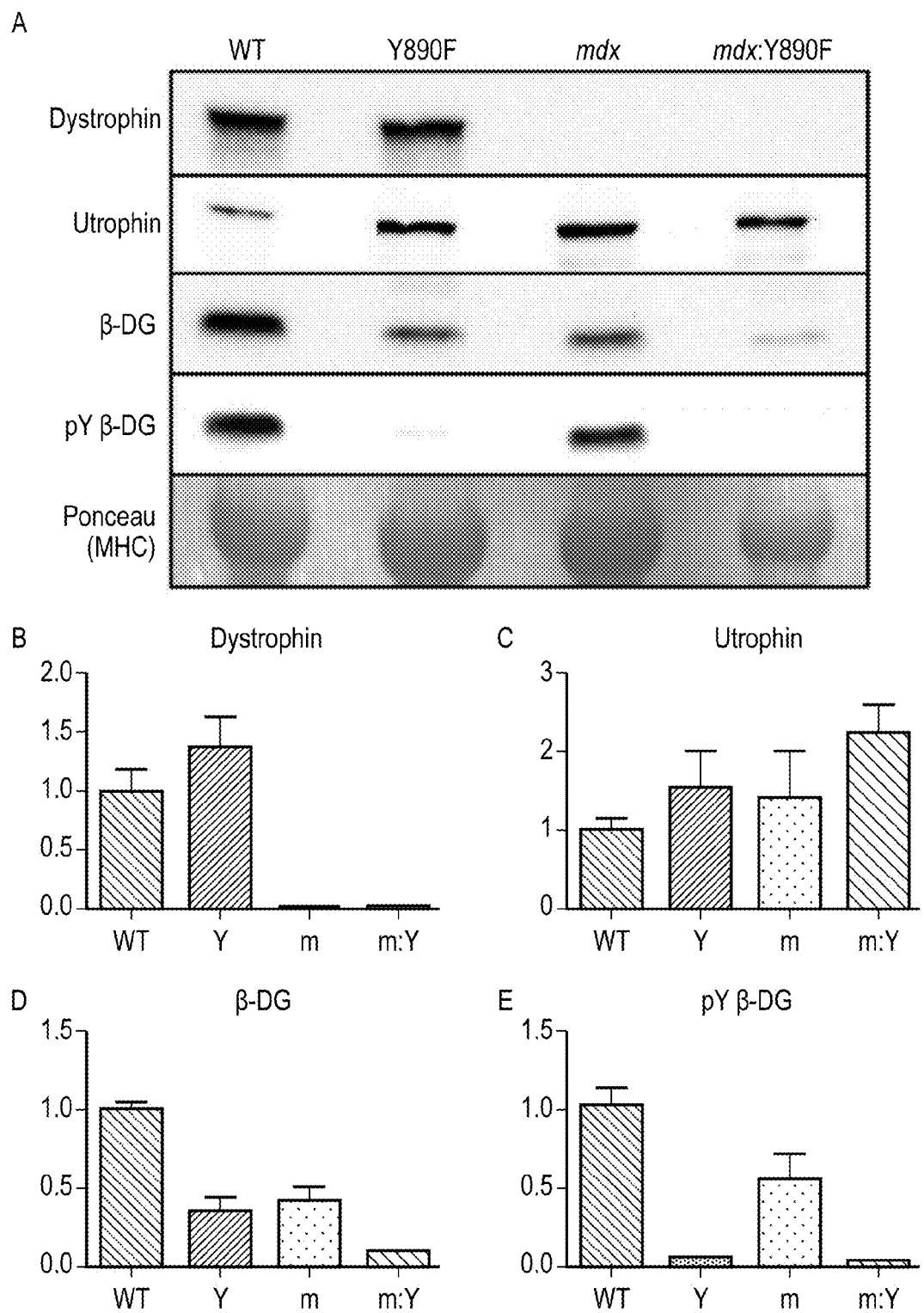

FIG. 4. Illustrates western blot analysis of dystrophin, utrophin and dystroglycan.

In keeping with the genetic background of the respective animal models, dystrophin was not detectable in western blots of muscle from mdx (m) or Dag1$^{Y890F/Y890F}$/mdx Y/m) mice (4A, 4B) and pY β-dystroglycan was not detectable in muscle from Dag1$^{Y890F/Y890F}$ (Y) or Dag1$^{Y890F/Y890F}$/mdx mice (4A, 4E). Compared to wildtype (WT), un-phosphorylated β-dystroglycan was significantly reduced in all mice (4D), but despite an upward trend in utrophin levels from WT to Y to m to Y/m, the differences were not significant (4C). Data are mean±SEM n=4.

Figure 5:
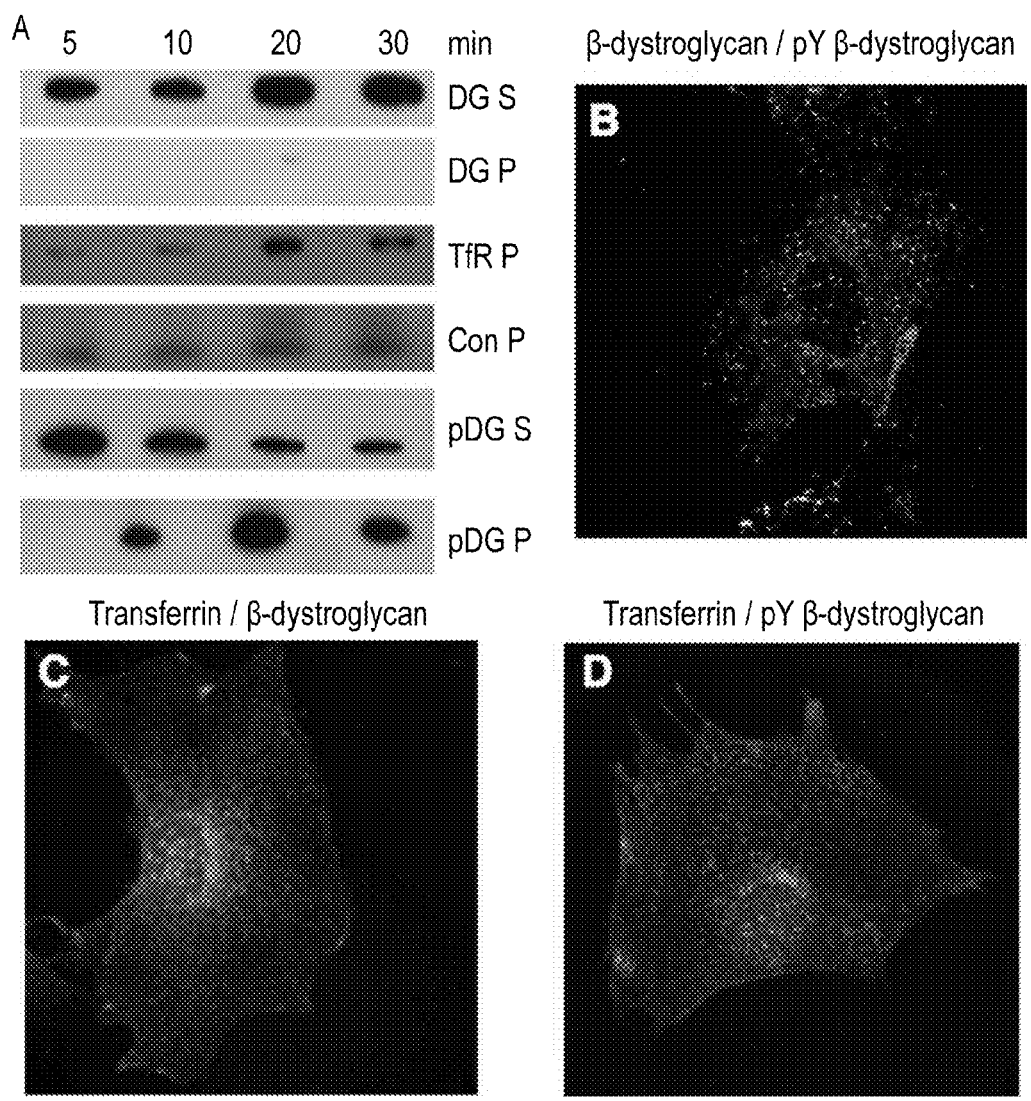

FIG. 5. Illustrates internalisation of pY890 β-dystroglycan in myoblasts.

Cell surface biotinylation followed by recovery of endocytosed biotinylated proteins (5A) revealed that only tyrosine phosphorylated β-dystroglycan (pDG) was internalised and recovered in the pellet fraction (pDG P) with a clear reduction over time of the surface supernatant fraction (pDG S). Unphosphorylated β-dystroglycan (DG) remained on the cell surface (DG S) with no unphosphorylated β-dystroglycan being internalised (DG P). Control western blots for transferrin receptor (TfR P) demonstrate the time course of clathrin mediated endocytosis in these cells, and blotting of an unknown biotinylated protein (Con P) acts as a loading control. Immunofluorescence localisation of β-dystroglycan and transferrin reveal distinct localisation patterns for each. pY β-dystroglycan localised to a population of larger vesicular structures that were less widely distributed through the cell (5B, 5D) whereas unphosphorylated β-dystroglycan was present in smaller vesicular structures that were more widely distributed through the cell (5B, and 5C) with relatively little overlap between phosphorylated and un-phosphorylated dystroglycan other than in the perinuclear area (5B). Neither unphosphorylated nor tyrosine phosphorylated β-dystroglycan (5C and 5D respectively) showed any colocalisation with transferrin (5C and 5D).

Figure 6:
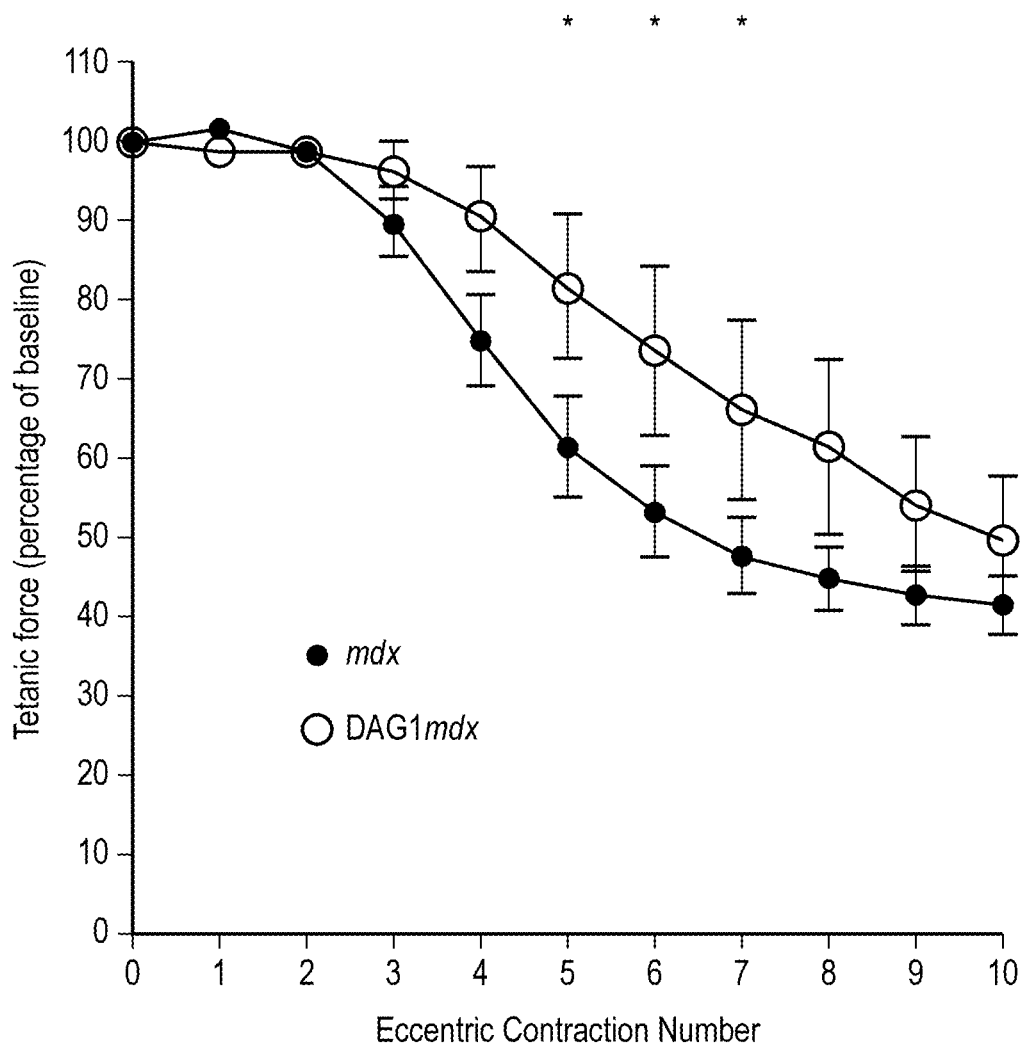

FIG. 6. Illustrates resistance to contraction-induced injury in mdx and Dag1$^{Y890F/Y890F}$/mdx mice.

The TA muscle from anaesthetised Dag1$^{Y890F/Y890F}$/mdx (n=4) and mdx mice (n=5) underwent a protocol of 10 eccentric contractions in situ. Each stretch induced a 10% increase in muscle length during a tetanic contraction. Tetanic force is expressed as a percentage of baseline isometric force produced prior to the first stretch. The drop in tetanic force was significantly reduced in Dag1$^{Y890F/Y890F}$/mdx mice compared to age-matched mdx controls (P=0.006). Dag1$^{Y890F/Y890F}$/mdx mice were significantly stronger than mdx mice at contractions 5, 6 and 7 (P=0.025, 0.025 and 0.040 respectively; Two-way Repeated Measures ANOVA with Tukey's Post-hoc test). TA: tibialis anterior. Error bars represent SEM.

Figure 7:
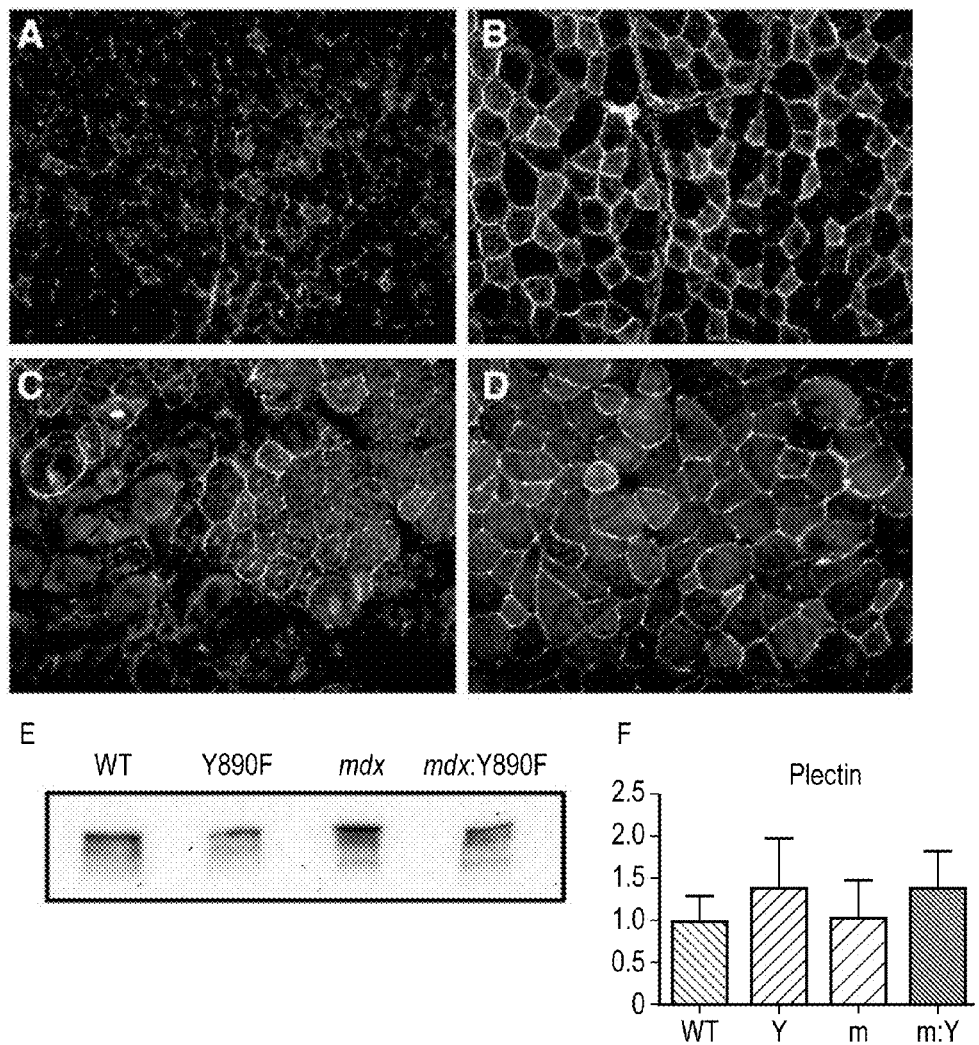

FIG. 7. Illustrates plectin staining is increased at the sarcolemma of Dag1$^{Y890F/Y890F}$/mdx mice. Immunofluorescence localisation of plectin (7A-D) revealed an expected increase in sarcolemmal staining in mdx mice, most often associated with regenerating fibres where plectin staining also localises around the central nuclei (7B). However, there was also a significant localisation of plectin to the sarcolemma in Dag1$^{Y890F/Y890F}$ mice (7C) which was maintained at a similar level in Dag1$^{Y890F/Y890F}$/mdx mice (7D). Quantification of plectin levels by western blotting in wildtype (WT), Dag1$^{Y890F/Y890F}$(Y), mdx (m) or Dag1$^{Y890F/Y890F}$/mdx Y/m) mice (7E,7F) revealed a slight increase in plectin levels in Dag1$^{Y890F/Y890F}$ mice in keeping with the immunohistochemistry (7C), however this increase was not significant (mean±SEM, n=4).

Figure 8:
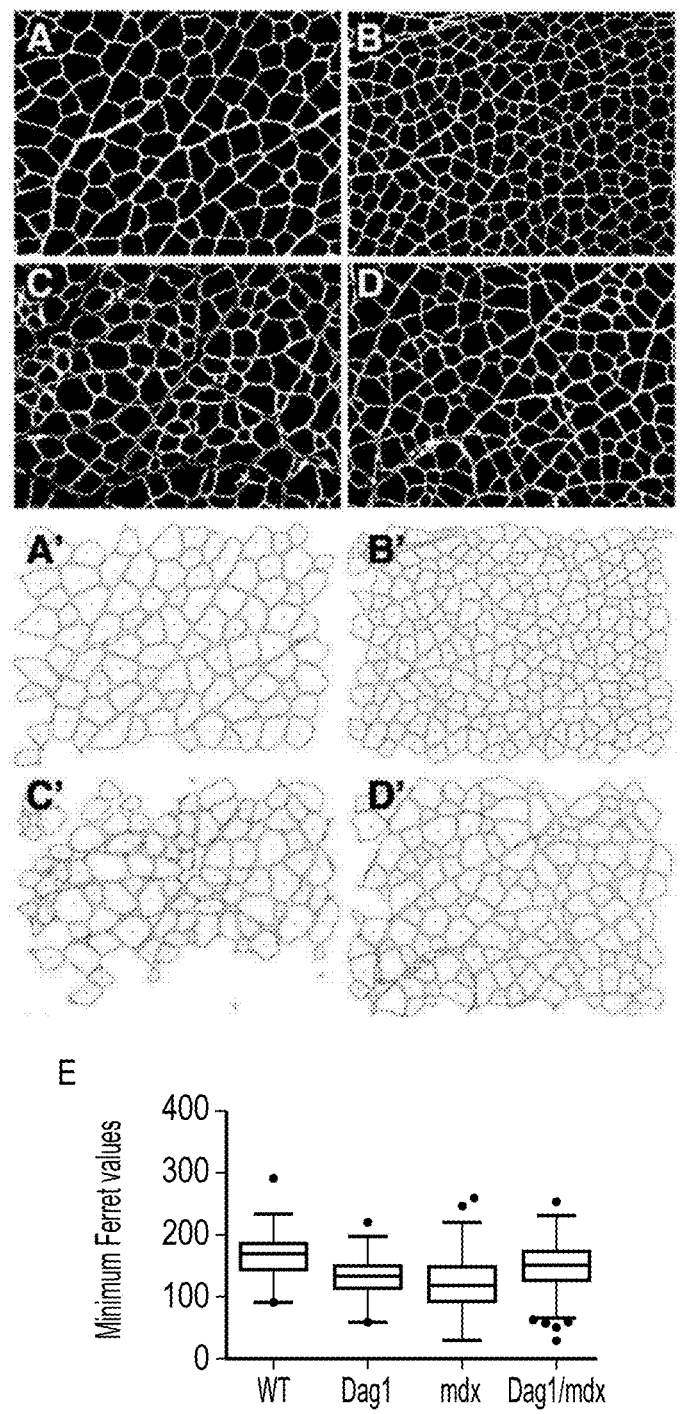

FIG. 8. Illustrates an estimation of fibre size by image analysis. Minimum Ferret's diameter was calculated on laminin stained quadriceps sections of wildtype, mdx, Dag1$^{Y890F/Y890F}$ and Dag1$^{Y890F/Y890F}$/mdx mice (8A-D respectively). Following image processing (8A'-D') myofibre diameters were calculated using the imageJ plugin. Data for at least 150 fibres per mouse from three mice per genotype (two mice in the case of wildtype) are represented in 8E. There was a small but significant reduction in mean Ferret's diameter in Dag1$^{Y890F/Y890F}$ mice compared to wildtype, but this was not different from either mdx alone or Dag1$^{Y890F/Y890F}$/mdx.

Figure 9:
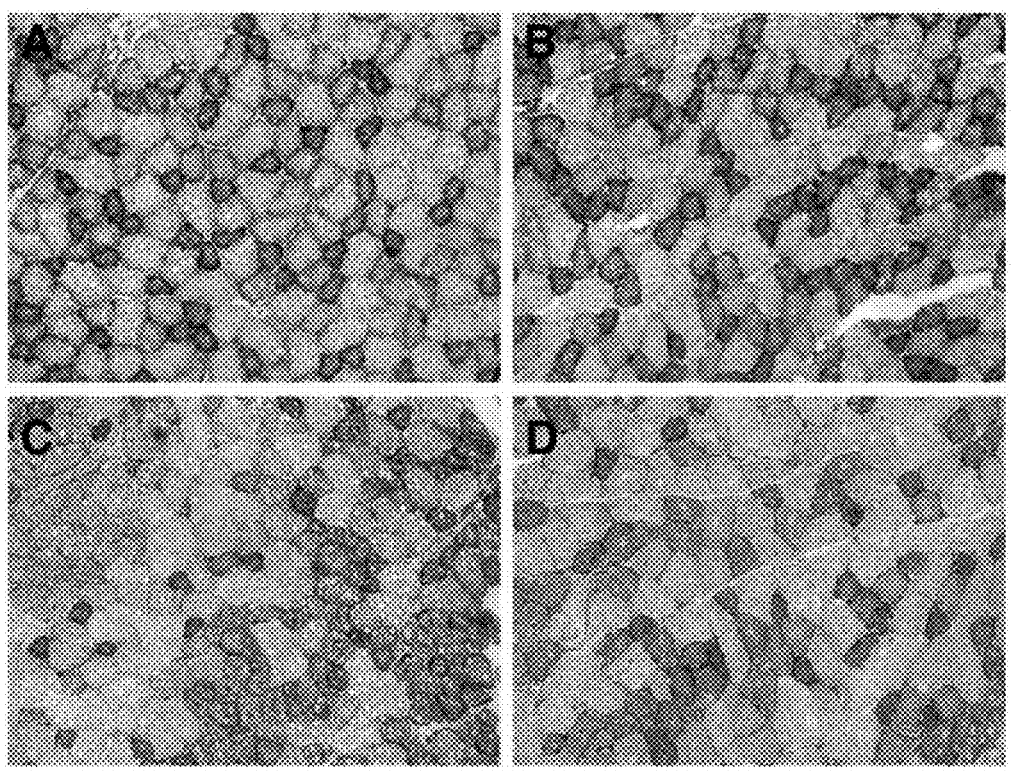

FIG. 9. Illustrates NADH staining of mouse muscle to reveal oxidative fibre type. Sections of mouse quadriceps were stained as detailed in materials and methods. Mouse genotypes are wildtype, mdx, Dag1$^{Y890F/Y890F}$ and Dag1$^{Y890F/Y890F}$/mdx (9A-D respectively). No qualitative difference in fibre type was observed between the different mouse genotypes. Type 1 fibres stain dark whereas type 2 fibres appear pale. Regenerating fibres in the mdx (9C) have a more mottled appearance.

Figure 10:
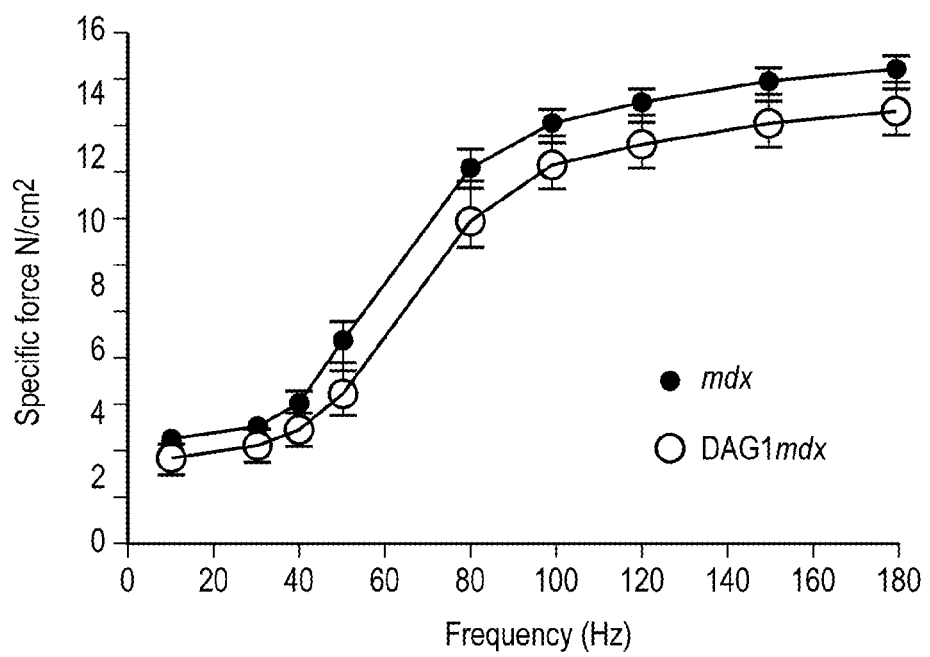

FIG. 10. Illustrates the force-frequency relationship in Dag1$^{Y890F/Y890F}$/mdx and mdx mice. TA muscles from anaesthetised Dag1$^{Y890F/Y890F}$/mdx (n=4) and mdx mice (n=5) underwent a series of isometric contractions in situ induced by stimulation of the common peroneal nerve at 10, 30, 40, 50, 80, 100, 120, 150 and 180 Hz. Stimulations were delivered 1 minute apart. The force frequency data from mdx and Dag1$^{Y890F/Y890F}$ mdx mice were not significantly different from each other (Two way Repeated Measures ANOVA with Tukey's post-hoc comparison). TA: tibialis anterior. Error bars represent SEM.

Figure 11:
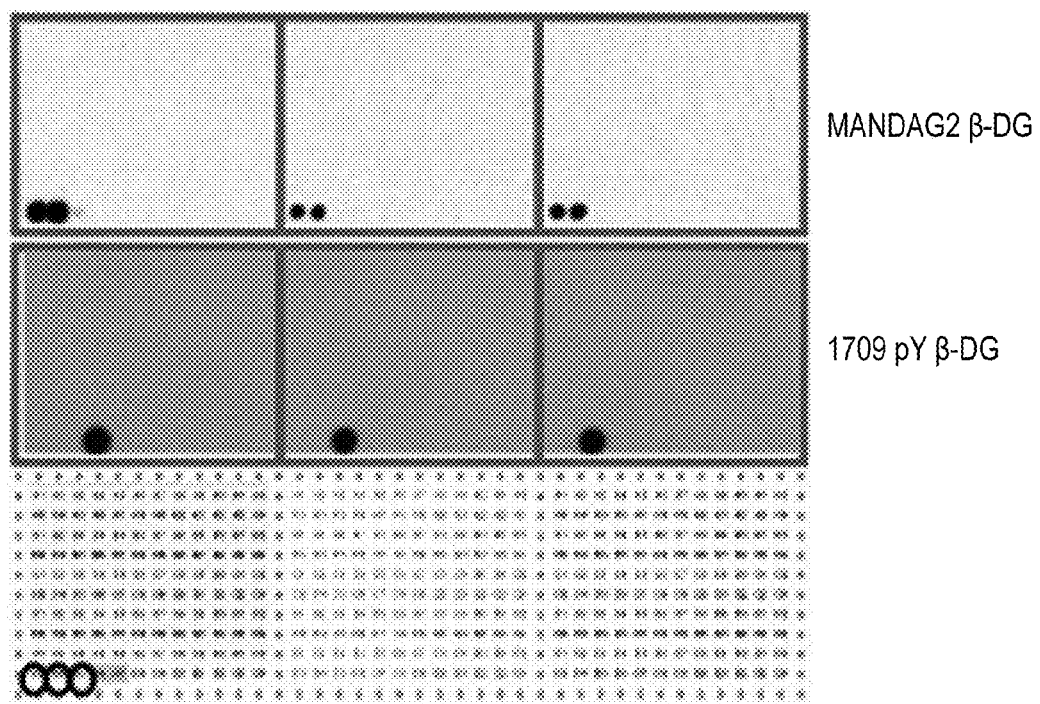

FIG. 11. Illustrates epitope mapping of β-dystroglycan antibodies. Peptide SPOT arrays comprising the entire cytoplasmic domain of β-dystroglycan as 15 residues peptides with a one amino acid overlap (see (45) for full details of peptide composition and sequences) were probed with the β-dystroglycan monoclonal antibody MANDAG2 and the anti pY890 polyclonal serum 1709. MANDAG2 as has been shown previously is specific for the last two peptides of β-dystroglycan (E13 and E14) but does not detect peptide E15 which contains a phosphorylated tyrosine at position 890. The antiserum 1709 on the other hand does not detect any un-phosphorylated peptide on the array, but specifically detects peptide E15 containing pY890 in the context of the c-terminus of β-dystroglycan.

Figure 12:
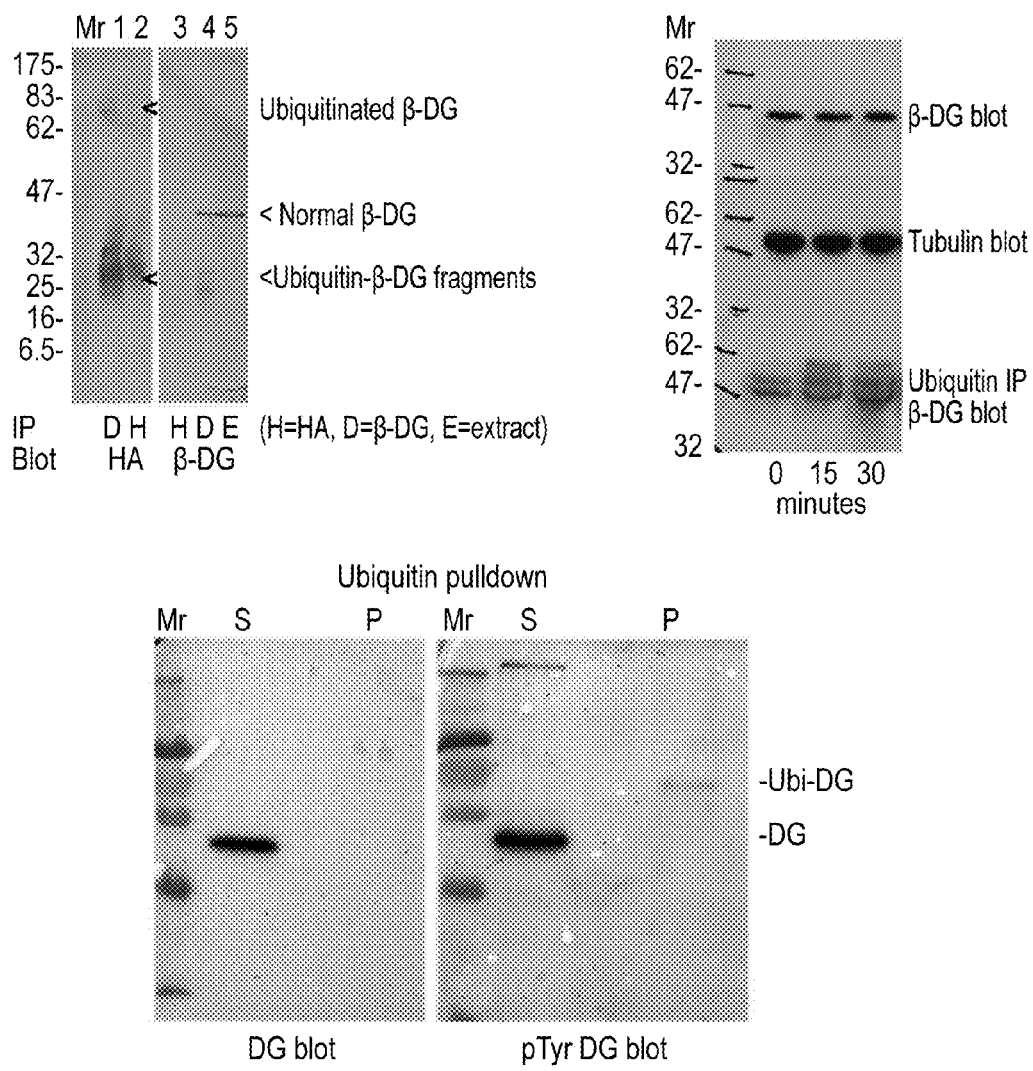

FIG. 12. Illustrates identification of β-dystroglycan ubiquitination following protein tyrosine phosphatase inhibition. Tyrosine phosphatases were inhibited in vitro using peroxyvanadate and samples from cells expressing HA-tagged ubiquitin taken for immunoprecipitation and western blot analysis. Immunoprecipitation with either the HA tag, or b-dystroglycan and blotting for HA revealed the presence of low molecular weight ubiquitin –b-Dystroglycan fragments (degradation products) and high molecular weight ubiquitinated b-dystroglycan (left panels). A time course of treatment revealed an increase in the proportion and number of ubiquitin-b-dystroglycan bands (right panels lower pane).

Figure 13:
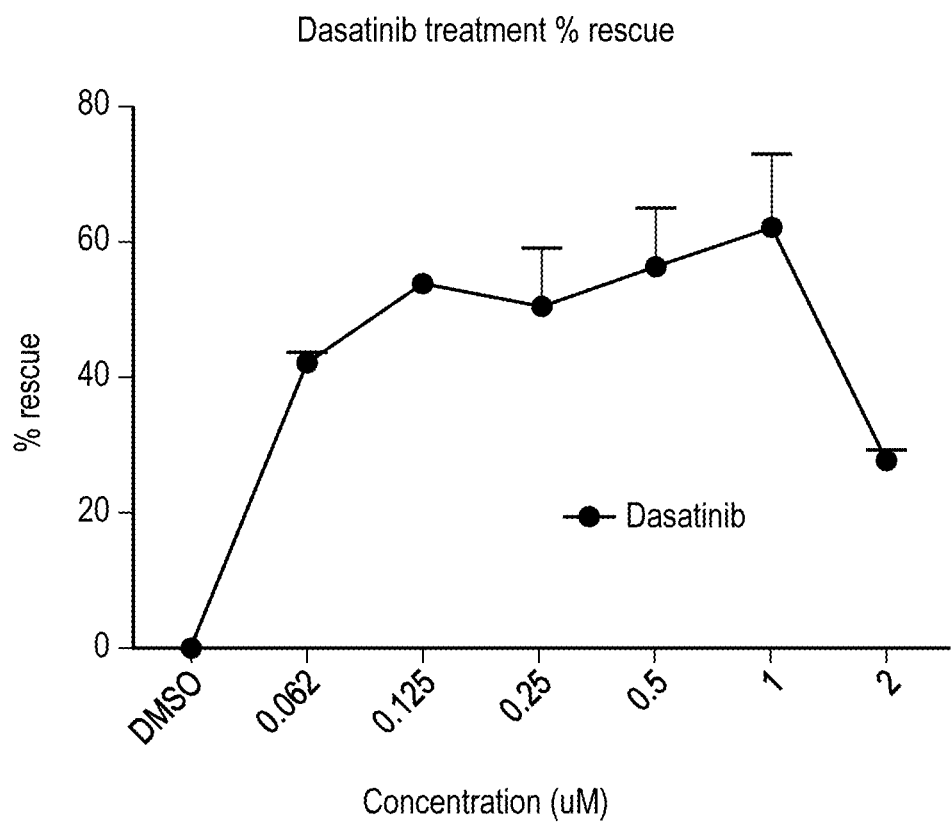

FIG. 13. Illustrates dose dependent rescue of the dystrophic phenotype in sapje fish by the tyrosine kinase inhibitor Dasatinib.

Figure 14:
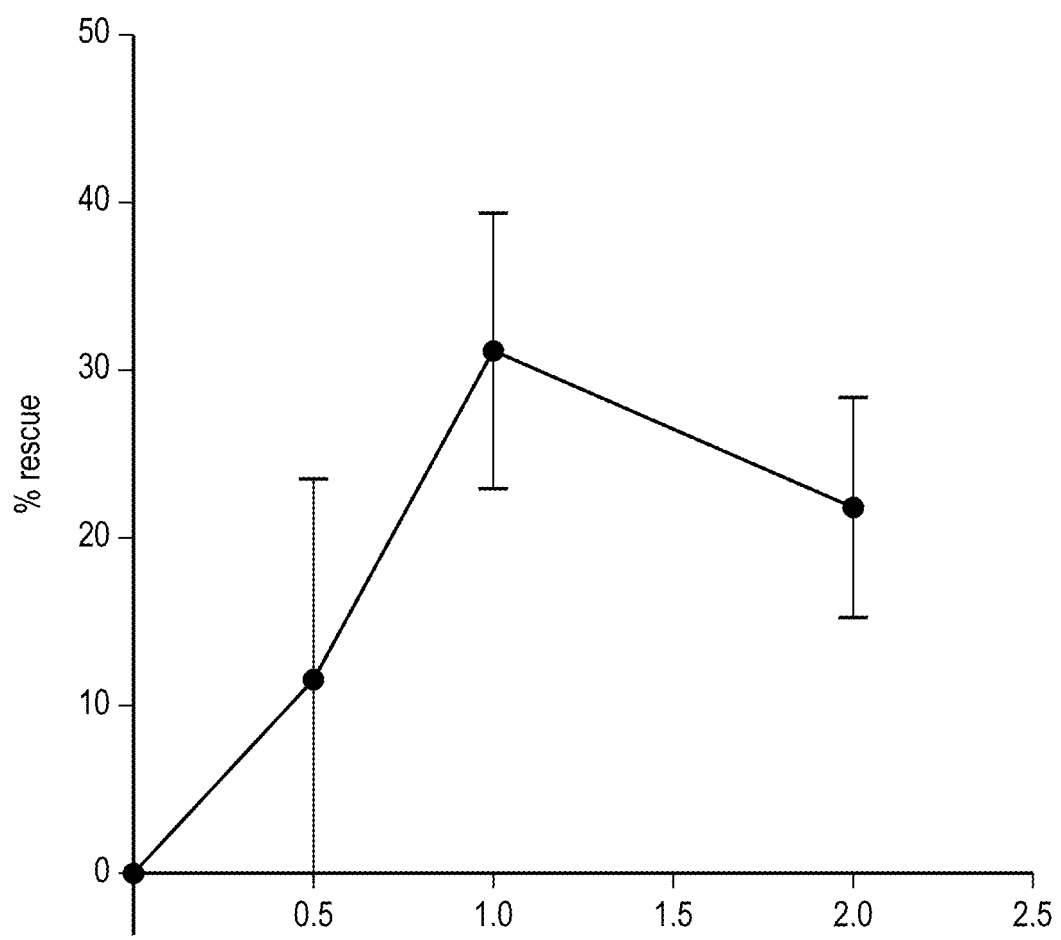

FIG. 14. Illustrates dose dependent rescue of the dystrophic phenotype in sapje fish by the ubiquitination inhibitor Pyr-41.

Figure 15:
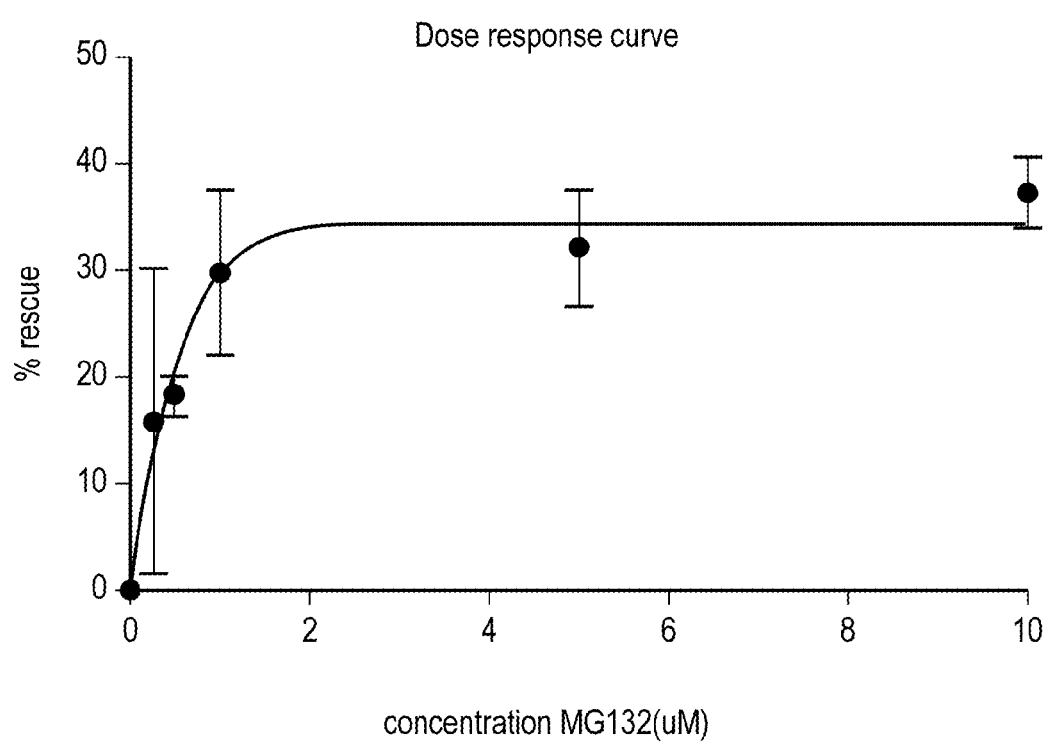

FIG. 15. Illustrates dose dependent rescue of the dystrophic phenotype in sapje fish by the proteasomal inhibitor MG132 (11).

Figure 16:
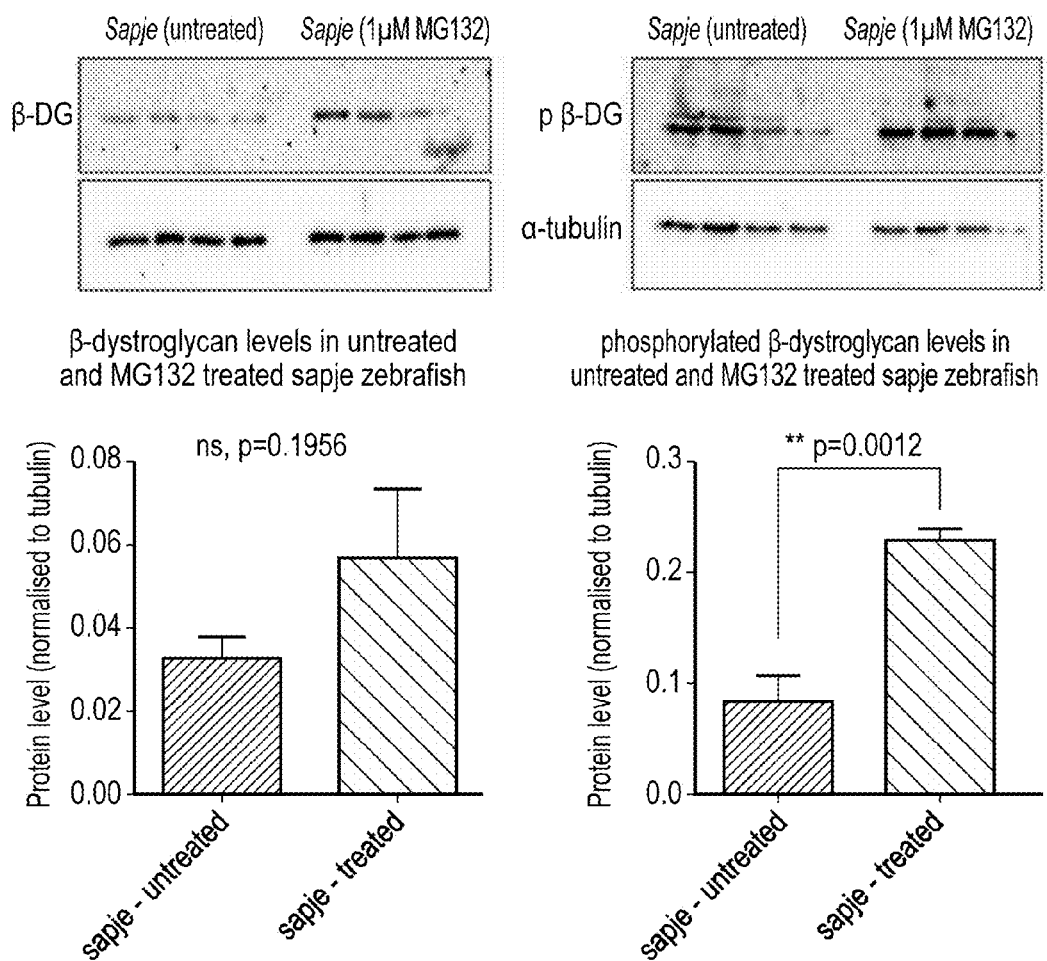

FIG. 16. Illustrates western blot analysis of β-dystroglycan (β-DG) and phosphorylated β-dystroglycan (p β-DG) in sapje fish (blue bars) and in sapje fish treated with 1 μM of the proteasomal inhibitor MG132 (purple bars).

FIG. 17. Provides the polypeptide sequence of SEQ ID NO:1.

FIG. 18. Provides the polypeptide sequence of SEQ ID NO:2.

FIG. 19. Provides the polypeptide sequence of SEQ ID NO:3.

FIG. 20. Provides the polypeptide sequence of SEQ ID NO:4.

FIG. 21. Provides the polypeptide sequence of SEQ ID NO:5.

FIG. 22. Provides the polypeptide sequence of SEQ ID NO:6.

FIG. 23. Provides the polypeptide sequence of SEQ ID NO:7.

Figure 24:
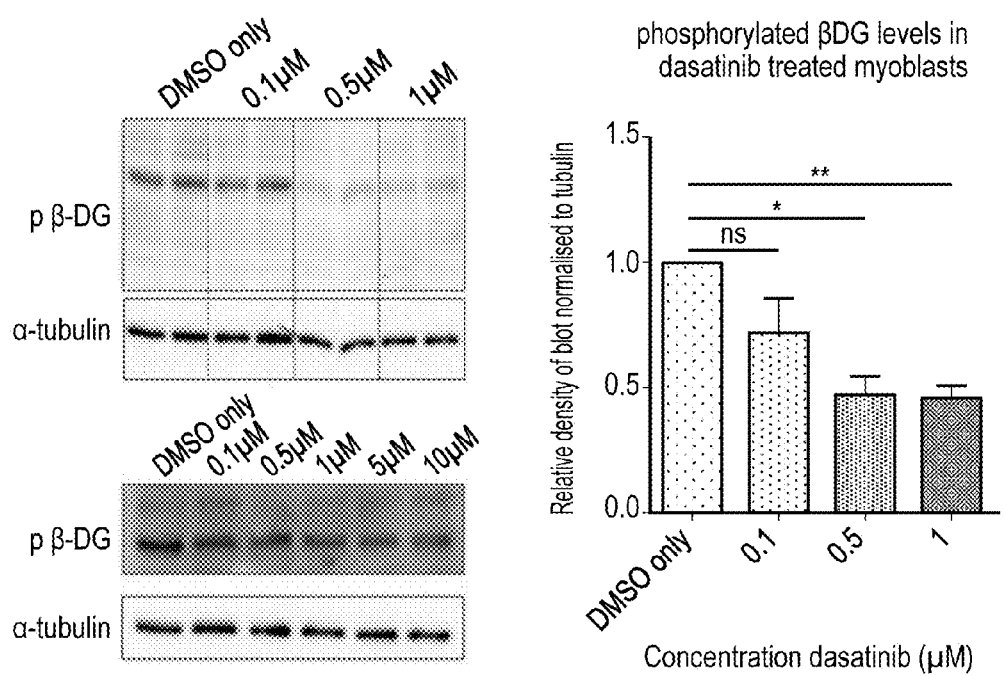

FIG. 24. Shows Dasatinib treatment inhibits dystroglycan phosphorylation in mouse myoblast (muscle precursor) cells.

Figure 25:
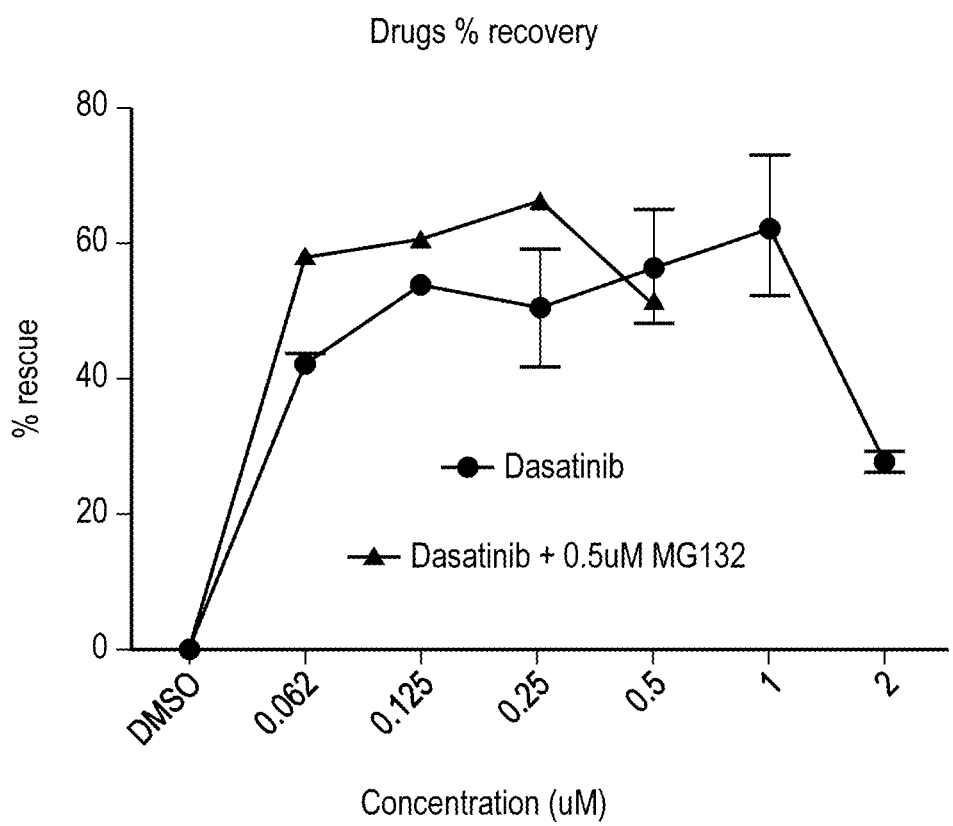

FIG. 25. Shows the additive/synergistic effect of Dasatinib on the dystrophic phenotype of sapje zebrafish.

Figure 26:
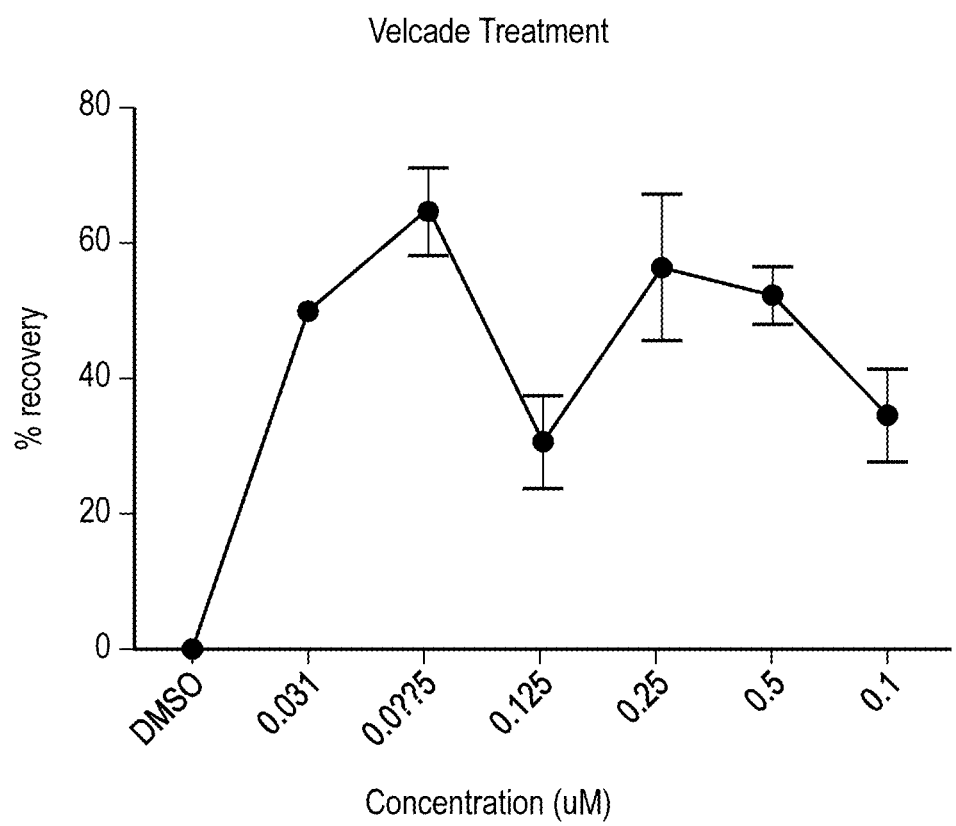

FIG. 26. Shows dose dependent rescue of the dystrophic phenotype in sapje fish by the proteasomal inhibitor bortezomib, which is sold under the trademark VELCADE®.

DETAILED DESCRIPTION

The inventors have surprisingly identified that inhibiting phosphorylation of β-dystroglycan results in a significant improvement in pathophysiology in mdx mice. The inventors have shown that preventing phosphorylation of a specific tyrosine residue within a PPxY domain in β-dystroglycan results in a significant improvement in several parameters of muscle pathophysiology associated with muscular dystrophy including; reduction in centrally nucleated fibres, less Evans blue dye infiltration and lower serum creatine kinase levels. In addition, the inventors have shown that inhibition of tyrosine phosphorylation, ubiquitination or proteasomal degradation in sapje fish improves the dystrophic phenotype. These findings provide for a new therapeutic approach to treating a subject with a disorder or symptom associated with reduced dystroglycan function.

The invention is therefore based on the unexpected finding that phosphorylation of a tyrosine residue of dystroglycan, its subsequent ubiquitination and degradation by the proteasome are all events that can be targeted by compounds such as small molecule inhibitors, so as to provide a systemic and universal treatment for subjects with a disorder or symptom associated with reduced dystroglycan function.

β-Dystroglycan

Dystroglycan is a known transmembrane laminin receptor that consists of a highly glycosylated, extracellular alpha subunit (alpha-Dystroglycan) and a transmembrane beta subunit (beta-Dystroglycan), both of which are encoded by the gene DAG1 and generated by post-translational cleavage and processing.

An 895 amino acid polypeptide sequence of human dystroglycan is designated SEQ ID NO:1 and illustrated in FIG. 17. The human dystroglycan polypeptide sequence is encoded by a nucleic acid molecule, designated SEQ ID NO:5, illustrated in FIG. 21. The polypeptide of SEQ ID NO:1 is processed to release a 29 aa signal peptide from the N-terminus, the alpha-Dystroglycan polypeptide and the beta-Dystroglycan polypeptide. The alpha-Dystroglycan polypeptide consists of amino acid residues 30-653 of SEQ ID NO:1. The beta-Dystroglycan polypeptide consists of amino acid residues 654-895 of SEQ ID NO:1.

A mutant human dystroglycan polypeptide, wherein a tyrosine of a PPxY domain is substituted with phenylalanine, is designated SEQ ID NO:2 and illustrated in FIG. 18. The human β-dystroglycan polypeptide sequence, wherein the tyrosine of the PPxY domain is substituted with phenylalanine consists of amino acid residues 654-895 of SEQ ID NO:2.

An 893 amino acid polypeptide sequence of mouse dystroglycan is designated SEQ ID NO:3 and illustrated in FIG. 19. The mouse dystroglycan polypeptide sequence is encoded by a nucleic acid molecule, designated SEQ ID NO:6, illustrated in FIG. 22. The polypeptide of SEQ ID NO:3 is processed to release a 27 aa signal peptide from the N-terminus, the alpha-Dystroglycan polypeptide and the beta-Dystroglycan polypeptide. The alpha-Dystroglycan polypeptide consists of amino acid residues 28-653 of SEQ ID NO:3. The beta-Dystroglycan polypeptide consists of amino acid residues 654-893 of SEQ ID NO:3.

A mutant mouse dystroglycan polypeptide, wherein a tyrosine of a PPxY domain is substituted with phenylalanine, is designated SEQ ID NO:4 and illustrated in FIG. 20. The mouse β-dystroglycan polypeptide sequence, wherein the tyrosine of the PPxY domain is substituted with phenylalanine consists of amino acid residues 654-893 of SEQ ID NO:2. The mutant mouse dystroglycan polypeptide sequence is encoded by a nucleic acid molecule, designated SEQ ID NO:7, illustrated in FIG. 23.

β-dystroglycan has several motifs in its carboxy-terminus including a PPxY domain, a RxxxPxxP domain and a YxPP domain (Moore and Winder, cell communication and signalling; 2010, 8:3). The PPxY domain (also referred to as a PPxY motif) binds to proteins comprising a WW domain, such as dystrophin and utrophin. Within the PPxY domain, "P" represents proline, "Y" represents tyrosine and "x" represents any amino acid (e.g. any one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine or tryptophan). In human β-dystroglycan, the PPxY domain spans amino acids 889 to 892. In mouse β-dystroglycan, the PPxY domain spans amino acids 887 to 890.

Unless stated otherwise, the terms "dystroglycan", "α-dystroglycan" and "β-dystroglycan" as used herein refer to a dystroglycan, an α-dystroglycan and a β-dystroglycan polypeptide respectively.

Compounds

The invention provides compounds for use in treating a disorder or symptom associated with reduced dystroglycan function in a subject.

As used herein, the term "compound" refers to a substance that is suitable for use in treating a disorder or symptom associated with reduced dystroglycan function in a subject. By way of example, the compound may be a small inhibitory molecule, an anti-proteinase, a metalloproteinase, or an intramembrane proteinase (gamma sectretase) inhibitor. Preferably, the compound is a small inhibitory molecule.

The inventors have surprisingly found that a compound that is capable of inhibiting ubiquitination is useful in the treatment of a disorder or symptom associated with reduced dystroglycan function in a subject. Preferably, the compound is capable of inhibiting ubiquitination of β-dystroglycan. As used herein, the phrase "capable of inhibiting ubiquitination" refers to (but is not limited to) compounds that have the ability to reduce ubiquitination of target proteins. As used herein, "ubiquitination" describes the overall mechanism by which one or more ubiquitin proteins are attached to proteins to label them for proteasomal destruction. The term "ubiquitination" is interchangeable with "ubiquitylation". A compound that is capable of inhibiting ubiquitination may reduce ubiquitination directly (e.g. by inhibiting activation of ubiquitin by the E1 ubiquitin activating enzyme, inhibiting transfer of ubiquitin to the active site of a ubiquitin conjugating enzyme E2, and/or inhibiting the activity of E3 ubiquitin protein ligase) or indirectly (e.g. by affecting upstream pathways (e.g. phosphorylation) that determine whether or not a protein is targeted for the ubiquitin-proteasomal degradation pathway).

Preferably, the compound is a ubiquitination inhibitor. As used herein, the phrase "ubiquitination inhibitor" refers to a compound that is capable of reducing ubiquitination directly (e.g. by inhibiting activation of ubiquitin by the E1 ubiquitin activating enzyme, inhibiting transfer of ubiquitin to the active site of a ubiquitin conjugating enzyme E2, and/or inhibiting the activity of E3 ubiquitin protein ligase). By way of example, the compound may be a ubiquitin E1 inhibitor, such as Pyr-41. The term "ubiquitin E1 inhibitor" is used herein to refer to an inhibitor of the E1 ubiquitin activating enzyme.

As used herein, the terms "inhibit", "down-regulate" and "reduce" refer to an alteration of the level of e.g. ubiquitination, phosphorylation etc such that the aforementioned level of ubiquitination, phosphorylation etc is less than that observed in the absence of the inhibiting substance or compound (e.g. inhibitor). Inhibition may be reversible or irreversible.

A compound may be capable of inhibiting phosphorylation. Preferably, the compound is capable of inhibiting phosphorylation of β-dystroglycan. As used herein, the phrase "capable of inhibiting phosphorylation" refers to (but is not limited to) compounds that have the ability to reduce phosphorylation of target proteins. As used herein, "phosphorylation" describes the overall mechanism by which a phosphate group is added to a protein or other organic molecule. Accordingly, a compound that is capable of inhibiting phosphorylation may reduce phosphorylation directly (e.g. by inhibiting one or more kinases) or indirectly (e.g. by affecting upstream pathways that determine whether or not a protein is phosphorylated or activating phosphatases that removes phosphate groups from proteins). Phosphorylation usually occurs on serine, threonine, tyrosine or histidine residues in eukaryotic proteins. By way of example, tyrosine kinases are the enzymes responsible for tyrosine phosphorylation, which is of particular relevance to the present invention. Preferably, the compound is capable of inhibiting tyrosine phosphorylation.

Preferably, the compound is an Src family tyrosine kinase inhibitor. Src family tyrosine kinases are known to phosphorylate β-dystroglycan. The inventors have shown that Src family tyrosine kinase inhibitors prevent β-dystroglycan degradation and improve dystrophic phenotype of sapje fish. Preferably, the Src family tyrosine kinase inhibitor is selected from the group consisting of dasatinib (sold under the trademark SPRYCEL®), bosutinib, and saracatinib, however, other Src family tyrosine kinase inhibitors may also be used. Several relevant inhibitors that target phosphorylation are known, some of which are clinically approved or awaiting approval as cancer therapies.

A proteasomal inhibitor is also an example of a compound in the context of the invention, as it is suitable for use in treating a disorder or symptom associated with reduced dystroglycan function in a subject. As used herein, the phrase "proteasomal inhibitor" refers to any compound that blocks the action of the proteasome, either directly or indirectly. Several proteasomal inhibitors are known, some of which are clinically approved or awaiting approval as cancer therapies. Suitable examples include MG132, MG-115, ALLN, carfilzomib and bortezomib (sold under the trademark VELCADE®). Treatment with the proteasome inhibitor bortezomib (sold under the trademark VELCADE®) has been shown to restore DGC components in the mdx mouse (Gazzerro. E, et al. Am. J. Pathol., 2010. 176: 1863).

A compound of the invention can be for use or administration alone or in combination with at least one or more other compounds. Administration "in combination with" at least one or more other compounds includes simultaneous (concurrent) and consecutive administration in any order. "Combined use" and "combination" in the context of the invention also includes a pharmaceutical product comprising both the compound and at least one or more other compounds, as discrete separate dosage forms, in separate containers or e.g. in blisters containing both types of drugs in discrete solid dosage units, e.g. in a form in which the dosage units which have to be taken together or which have to be taken within one day are grouped together in a manner which is convenient for the patient. Said pharmaceutical product itself or as a part of a kit may contain instructions for the simultaneous, sequential or separate administration of the discrete separate dosage units, to a subject in need thereof.

For example, a compound capable of inhibiting ubiquitination (e.g. a ubiquitination inhibitor such as a ubiquitin E1 inhibitor, preferably Pyr-41) may be useful in combination with a proteasomal inhibitor (e.g. MG132, MG-115, ALLN, Carfilzomib or bortezomib) and/or a compound capable of inhibiting phosphorylation (e.g. a tyrosine kinase inhibitor such as a Src tyrosine kinase inhibitor, preferably dasatimib, bosutinib or sracatinib).

By way of a further example, a compound capable of inhibiting phosphorylation (e.g. a tyrosine kinase inhibitor such as a Src tyrosine kinase inhibitor, preferably dasatinib, bosutinib or sracatinib) may be useful in combination with a proteasomal inhibitor (e.g. MG132, MG-115, ALLN, Carfilzomib or bortezomib) and/or a compound capable of inhibiting ubiquitination (e.g. a ubiquitination inhibitor such as a ubiquitin E1 inhibitor, preferably Pyr-41).

By way of a further example, a proteasomal inhibitor (e.g. MG132, MG-115, ALLN, Carfilzomib or bortezomib) may be useful in combination with a compound capable of inhibiting phosphorylation (e.g. a tyrosine kinase inhibitor such as a Src tyrosine kinase inhibitor, preferably dasatimib, bosutinib or saracatinib) and/or a compound capable of inhibiting ubiquitination (e.g. a ubiquitination inhibitor such as a ubiquitin E1 inhibitor, preferably Pyr-41).

Combinatorial therapy of two or more of a proteasomal inhibitor, a ubiquitination inhibitor and a tyrosine kinase inhibitor should provide a successful treatment regimen for muscular dystrophy by targeting simultaneously the phosphorylation of dystroglycan on tyrosine, and the increased degradation of dystroglycan and other DGC components that occurs when dystrophin is missing. Such a combinatorial therapy could also be of use as an adjunct to improve the efficacy of known therapies for a disorder or symptom associated with reduced dystroglycan function (e.g. muscular dystrophy) such as exon skipping, utrophin upregulation and nonsense codon read-through. As used herein, the phrase "improve the efficacy" refers to an increase or an improvement in the therapeutic activity of a known therapy for such disorders or symptoms.

Reference herein to a "compound" is intended to include one or more compounds according to the invention.

The inventors have surprisingly found that preventing dystroglycan phosphorylation of the tyrosine amino acid residue in the PPxY domain of β-dystroglycan increases the levels of plectin in the sarcolemma of dystrophic mice.

The finding that plectin levels increase in the sarcolemma of dystrophic Dag1$^{Y890F/Y890F}$ mdx mice suggests that plectin is a further therapeutic candidate for a disorder or symptom associated with reduced β-dystroglycan in a subject. Plectin is therefore a potential therapeutic agent for treating a disorder or symptom associated with reduced β-dystroglycan in a subject, either when administered alone, or in combination with a compound of the present invention.

Plectin is an approximately 500 kDa protein of the plakin family, which interlinks different elements of the cytoskeleton. The plectin polypeptide acts as a link between the three main components of the cytoskeleton; microtubules, actin microfilaments and intermediate filaments. It also links the cytoskeleton to junctions present in the plasma membrane that structurally connect different cells. Plectin therefore plays an important role in the mechanical integrity of tissue.

The human plectin polypeptide is shown in GenBank Accession Number: CAA91196.1. Plectin undergoes alternative splicing, forming at least nine isoforms of which four are in muscle. All the plectin isoforms are useful in the methods of the invention, with isoform plectin 1f being of particular use.

Treatment of a Subject

The inventors have surprisingly found that the compounds of the invention are useful in treating a disorder or symptom associated with reduced dystroglycan function in a subject.

As used herein, the terms "treat", "treating" and "treatment" are taken to include an intervention performed with the intention of preventing the development or altering the pathology of a disorder or symptom. Accordingly, "treatment" refers to both therapeutic treatment and prophylactic or preventative measures, wherein the object is to prevent or slow down (lessen) the targeted pathological disorder or symptom.

As used herein, the phrase "a disorder associated with reduced dystroglycan function" refers to, but is not limited to, any disease or disorder resulting directly or indirectly from and/or completely or partially from a reduction in dystroglycan function. In this context, "a disorder associated with reduced dystroglycan function" is intended to include muscular dystrophy.

As used here, the terms "disease" and "disorder" are used interchangeably.

As used herein, a "muscular dystrophy" is intended to include Duchenne, Becker, limb-girdle, congenital, facioscapulohumeral, mytonic, oculopharyngeal, distal and Emery-Dreifuss muscular dystrophy as well as muscular dystrophy-like conditions. Preferably, the muscular dystrophy is selected from the group consisting of Duchenne Muscular Dystrophy (DMD), Limb Girdle Muscular Dystrophy (LGMD), Congenital Muscular Dystrophy (CMD) and Becker Muscular Dystrophy (BMD).

As used herein, the terms "Limb Girdle Muscular Dystrophy" and "LGMD" are intended to include LGMD1A, LGMD1B, LGMD1C, LGMD1D, LGMD1E, LGMD1F, LGMD1G, LGMD2A, LGMD2B, LGMD2C, LGMD2D, LGMD2E, LGMD2F, LGMD2G, LGMD2H, LGMD2I, LGMD2J, LGMD2K, LGMD2L, LGMD2M, LGMD2N and LGMD2O. Preferably, the Limb Girdle Muscular Dystrophy is selected from the group consisting of Limb Girdle Muscular Dystrophy 2C, Limb Girdle Muscular Dystrophy 2D, Limb Girdle Muscular Dystrophy 2E, and Limb Girdle Muscular Dystrophy 2F.

As used herein, the terms "Congenital Muscular Dystrophy" and "CMD" are intended to include Laminin-$\alpha$2-deficient CMD (MDC1A), Ullrich congenital muscular dystrophy (UCMDs 1, 2 and 3), Walker-Warburg syndrome (WWS), Muscle-eye-brain disease (MEB), Fukuyama CMD (FCMD), CMD plus secondary laminin deficiency 1 and 2 (MDC1B and MDC1C), CMD with meta retardation and pachygyria (MDC1D) and rigid spine with muscular dystrophy type 1 (RSMD). Preferably, the Congenital Muscular Dystrophy is selected from the group consisting of MDC1A, MDC1B, MDC1D, Fukuyama CMD (FCMD), Muscle eye brain disease (MEB) and Walker Warburg Syndrome (WWS).

As used herein, the phrase "a symptom associated with reduced dystroglycan function" refers to, but is not limited to, any symptom resulting directly or indirectly from and/or completely or partially from a reduction in dystroglycan function. In this context, "a symptom" is a departure from a normal function or feeling in the subject. The symptom may be chronic, relapsing or remitting. The phrase "a symptom associated with reduced dystroglycan function" is intended to include, but not be limited to muscle weakness or degeneration, calf hypertrophy, reduced myofibre integrity, elevated serum creatine kinase levels, loss of dystrophin and dystrophin associated proteins, and central nucleation of muscle fibres.

Methods for assessing and/or identifying muscle weakness or degeneration, calf hypertrophy, reduced myofibre integrity, elevated serum creatine kinase levels, loss of dystrophin and dystrophin associated proteins, and central nucleation of muscle fibres are well known. By way of example, but without limitation, loss of dystrophin and dystrophin associated proteins may be assessed at a histological or a molecular (e.g. using PCR) level.

As used herein "a reduction in dystroglycan function" is intended to include any measurable decrease in dystroglycan function. Several methods for measuring dystroglycan function are known. One suitable method is western blotting. An example of a measurable decrease in dystroglycan function is a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or 100%, reduction compared to normal function.

As used here in the term "subject" refers to an individual, e.g., a human, pig, horse, mouse, cow, rat etc having or at risk of having a disorder or symptom associated with reduced dystroglycan function e.g. a muscular dystrophy. Preferably, the subject is a subject having a muscular dystrophy. The subject may be a patient i.e. a subject in need of treatment in accordance with the invention. In one embodiment, the subject has received treatment for the disorder or symptom associated with reduced dystroglycan function. Alternatively, the subject has not been treated prior to treatment in accordance with the present invention.

The compounds of the invention can be incorporated into pharmaceutical compositions suitable for administration. Such compositions typically comprise the compound and a pharmaceutically acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application.

When administered, the pharmaceutical compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents or compounds.

The compositions of the invention can be administered by any conventional route, including injection or by gradual infusion over time. The administration may, for example, be topical, oral, intravenous, intraperitoneal, intramuscular, intracavity, subcutaneous, or transdermal, intranasal, intracerebral or epidural.

The compositions of the invention are for administration in an effective amount. An "effective amount" is the amount of a composition that alone, or together with further doses, produces the desired response.

The compositions used are preferably are sterile and contain an effective amount of the active ingredient for producing the desired response in a unit of weight or volume suitable for administration to a subject. The response can, for example, be measured by measuring the physiological effects of the composition, such as decrease of disease symptoms etc. Other assays will be known to one of ordinary skill in the art and can be employed for measuring the level of the response.

The compound(s) of the present invention may also be used to improve muscle condition in a subject. By way of example, muscle condition may be improved in a subject by administering a compound of the invention to a subject. The method may be used, for example, to improve muscle condition in animals, or humans, particularly in respect of farming and or sports.

There is provided a method of treating a disorder or symptom associated with reduced dystroglycan function comprising administering a compound capable of inhibiting ubiquitination to a subject in need thereof.

There is also provided a method of treating a disorder or symptom associated with reduced dystroglycan function comprising administering a compound capable of inhibiting ubiquitination to a subject in need thereof in combination with at least one compound selected from a proteasomal inhibitor and a compound capable of inhibiting phosphorylation.

There is also provided a method of treating a disorder or symptom associated with reduced dystroglycan function comprising administering a compound capable of inhibiting phosphorylation to a subject in need thereof in combination with at least one compound selected from a proteasomal inhibitor and a compound capable of inhibiting ubiquitination.

There is also provided a method of treating a disorder or symptom associated with reduced dystroglycan function comprising administering a proteasomal inhibitor to a subject in need thereof in combination with at least one compound selected from a compound capable of inhibiting ubiquitination and a compound capable of inhibiting phosphorylation.

There is also provided a method of treating a disorder or symptom associated with reduced dystroglycan function comprising administering a combination of a compound capable of inhibiting ubiquitination and at least one compound selected from a proteasomal inhibitor and a compound capable of inhibiting phosphorylation to a subject in need thereof.

There is also provided a method of treating a disorder or symptom associated with reduced dystroglycan function comprising administering a combination of a compound capable of inhibiting phosphorylation and a proteasomal inhibitor to a subject in need thereof.

Method for Inhibiting Degradation of β-Dystroglycan

The surprising finding that the compounds of the invention affect β-dystroglycan degradation may also be used to provide a method for inhibiting degradation of β-dystroglycan.

Accordingly, in one aspect, the invention provides a method for inhibiting degradation of β-dystroglycan, wherein the method includes a step of exposing at least one cell comprising β-dystroglycan to at least one of: (i) a compound capable of inhibiting ubiquitination; and (ii) a compound capable of inhibiting phosphorylation.

Accordingly, the phrase "inhibiting degradation" refers to an alteration in the level of β-dystroglycan, e.g. a reduction or down regulation in break down or degradation. Degradation of β-dystroglycan may be inhibited directly or indirectly.

The method may be an in vivo method (e.g., by culturing the at least one cell with the compound) or, alternatively, an in vitro method (e.g., by administering the compound to a subject).

An in vitro method may be used to treat cells in culture.

Preferably the cells are striated muscle myoblast cells. More preferably the cells are muscle satellite cells.

Alternatively, said cell is selected from the group consisting of: a nerve cell; a mesenchymal cell; a muscle cell (cardiomyocyte, smooth muscle cell, vascular muscle cell or myotube); a liver cell; a blood cell (e.g. erythrocyte, CD4+ lymphocyte, CD8+ lymphocyte; pancreatic β cell; an endothelial cell; an epidermal keratinocyte; a fibroblast (e.g. dermal, corneal; intestinal mucosa, oral mucosa, bladder, urethral, prostate, liver); an epithelial cell (e.g. corneal, dermal, corneal; intestinal mucosa, oral mucosa, bladder, urethral, prostate, liver); a neuronal glial cell or neural cell; a hepatocyte stellate cell; a mesenchymal cell; a muscle cell; a kidney cell; a blood cell (e.g. CD4+ lymphocyte, CD8+ lymphocyte; or a pancreatic β cell, an embryonic stem cell Preferably the cells are mammalian cells. More preferably the cells are human.

In one embodiment, the compound of the invention is provided in a culture medium. In one embodiment, the compound is present at the start of culture. Alternatively, the compound is present after the start of culture. Alternatively, the compound is present continuously during culture.

Preferably the cultured cells are clonally homogeneous.

In one embodiment, the at least one cell is transformed or transfected with a nucleic acid encoding a β-dystroglycan polypeptide. Preferably the at least one cell is transiently transfected. Alternatively, (or additionally) the at least one cell naturally expresses a β-dystroglycan polypeptide.

Cells can be grown or cultured in the manner with which the skilled worker is familiar, depending on the cell type.

The culturing of mammalian cells has become a routine procedure and cell culture conditions which allow cells to proliferate are well defined. Typically, cell culture of mammalian cells requires a sterile vessel, usually manufactured from plastics, defined growth medium and, in some examples, feeder cells and serum, typically calf serum.

In vitro methods, including cell culture may be carried out in any suitable vessel. Preferably the vessel is selected from the group consisting of: a petri-dish; cell culture bottle or flask; multiwell plate. "Vessel" is construed as any means suitable to contain a cell culture.

In one embodiment, the method further comprises a step of exposing the cell to a proteasomal inhibitor.

The cell may be exposed to more than one compound of the invention. The cell may be exposed to the compounds simultaneously (concurrently) or consecutively, in any order. In one embodiment, at least one compound is present at the start of culture. Alternatively, at least one compound is present after the start of culture. Alternatively, at least one compound is present continuously during culture.

An in vivo method may be used to treat a subject having a disease, disorder or symptom, or at risk of having a disease, disorder or symptom, associated the reduced dystroglycan function. In addition, an in vivo method may be used to treat a subject having a disease, disorder, or symptom or at risk of having a disease, disorder, or symptom that may be treated by restoring or increasing dystroglycan function.

In one embodiment, the method involves administering one or more compounds of the invention.

The method may be a method to stimulate dystroglycan expression or activity. It is beneficial to stimulate dystroglycan expression or activity in diseases, disorders or symptoms in which dystroglycan is abnormally down regulated, or in diseases, disorders or symptoms in which increased dystroglycan activity is likely to have a beneficial effect.

Diseases, disorders or symptoms that may be treated by the method of the invention are listed in detail above.

According to a yet further aspect of the invention there is provided a method of treatment of a subject, preferably a mammal, more preferably a human, comprising administering to said subject a compound according to the invention.

Accordingly, the in vivo methods of the invention may be prophylactic and/or therapeutic.

β-Dystroglycan Polypeptides and Nucleic Acids

The invention is based on the surprising finding that mutation of the PPxY domain in β-dystroglycan, such that the mutated PPxY domain is incapable of undergoing tyrosine phosphorylation, inhibits β-dystroglycan degradation and significantly improves the pathophysiology of mdx mice.

Accordingly, in one aspect, the invention provides a β-dystroglycan polypeptide comprising a mutated PPxY domain, wherein the mutated PPxY domain is incapable of undergoing tyrosine phosphorylation.

In one embodiment, the tyrosine amino acid residue (Y) in the PPxY domain is substituted with an amino acid that is incapable of undergoing phosphorylation. The tyrosine amino acid residue may be substituted with any suitable alternative amino acid residue, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, or tryptophan. Preferably, the tyrosine amino acid residue is substituted with any one of arginine, histidine, lysine, aspartic acid, glutamic acid, asparagine, glutamine, cysteine, selenocysteine, glycine, proline, alanine, valine, isoleucine, leucine, methionine, phenylalanine, or tryptophan. Most preferably, the tyrosine amino acid residue is substituted with phenylalanine.

Preferably, the β-dystroglycan is a human dystroglycan. Preferably the human polypeptide has an amino acid sequence that is at least 80, 85, 90, 91, 92, 93, 94, 95, 96, 97, 99, 100% identical to the entire length of SEQ ID NO: 1, still more preferably at least 80, 85, 90, 91, 92, 93, 94, 95, 96, 97, 99, 100% identical to the entire length of amino acid residues 654-895 of SEQ ID NO:1. More preferably, the β-dystroglycan consists of the amino acid sequence of SEQ ID NO: 2, still more preferably the β-dystroglycan consists of amino acid residues 654-895 of SEQ ID NO: 2.

Alternatively, the β-dystroglycan is a mouse dystroglycan. Preferably the mouse polypeptide has an amino acid sequence that is at least 80, 85, 90, 91, 92, 93, 94, 95, 96, 97, 99, 100% identical to the entire length of SEQ ID NO: 3, still more preferably at least 80, 85, 90, 91, 92, 93, 94, 95, 96, 97, 99, 100% identical to the entire length of amino acid residues 654-893 of SEQ ID NO:3. More preferably, the β-dystroglycan consists of the amino acid sequence of SEQ ID NO: 4, still more preferably the β-dystroglycan consists of amino acid residues 654-893 of SEQ ID NO: 4.

The invention further provides a nucleic acid sequence which encodes the human β-dystroglycan comprising a mutated PPxY domain, wherein the tyrosine amino acid residue is substituted with phenylalanine.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

Polypeptides of the present invention can have amino acid sequences sufficiently or substantially identical to the amino acid sequences of SEQ ID NO:1 to 4, more preferably to amino acid residues 654-895 of SEQ ID NO: 2. The terms "sufficiently identical" or "substantially identical" are used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as sufficiently or substantially identical.

The invention also provides a nucleic acid molecule which encodes the mouse β-dystroglycan comprising a mutated PPxY domain, wherein the tyrosine amino acid residue is substituted with phenylalanine.

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA.

In one embodiment, the nucleic acid molecule comprises the nucleotide sequence of SEQ ID NO: 7, or a portions or fragment thereof. In one embodiment the nucleic acid molecule comprises a nucleotide sequence encoding a polypeptide of any one of SEQ ID NO's: 2 or 4, more preferably encoding a polypeptide comprising or consisting of amino acid residues 654-895 of SEQ ID NO:2.

In one embodiment, the nucleic acid sequence is at least about: 60%, 65%, 70%, 75%, 80%, 85%, 90%, 91%, 92%, 93%, 94%, 95%, 96%, 97%, 98%, 99% or 100%, identical to the entire length of the nucleotide sequence shown in SEQ ID NO:6. Alternatively, the nucleic acid sequence encodes a polypeptide that is at least about: 60%, 65%, 70%, 75%, 80%, 85%, 90%, 91%, 92%, 93%, 94%, 95%, 96%, 97%, 98%, 99% or 100%, identical to the entire length SEQ ID NO's: 2 or 4, more preferably encodes a polypeptide that is at least about: 60%, 65%, 70%, 75%, 80%, 85%, 90%, 91%, 92%, 93%, 94%, 95%, 96%, 97%, 98%, 99% or 100%, identical to the entire length of amino acid residues 654-895 of SEQ ID NO:2.

Preparation of Expression Vectors

Preferably expression vectors and plasmids of the present invention comprise a nucleic acid sequence encoding a dystroglycan polypeptide comprising a mutated PPxY domain, wherein the mutated PPxY domain is incapable of undergoing tyrosine phosphorylation as herein before described.

A man of skill in the art will be aware of the molecular techniques available for the preparation of expression vectors.

The nucleic acid molecule for incorporation into the expression vector of the invention, as described above, can be prepared by synthesizing nucleic acid molecules using mutually priming oligonucleotides and the nucleic acid sequences described herein.

A number of molecular techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the nucleic acid molecule to the expression vector. In one embodiment, the nucleic acid molecule is generated by restriction endonuclease digestion. Preferably, the nucleic acid molecule is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a nucleic acid molecule carrying polymeric linker sequences at its ends. These nucleic acid molecules are then cleaved with the appropriate restriction enzyme and ligated to an expression vector that has been cleaved with an enzyme that produces termini compatible with those of the nucleic acid molecule.

Alternatively, a vector comprising ligation-independent cloning (LIC) sites can be employed. The required PCR amplified nucleic acid molecule can then be cloned into the LIC vector without restriction digest or ligation (Aslanidis and de Jong, *Nucl. Acid. Res.* 18, 6069-6074, (1990), Haun, et al, *Biotechniques* 13, 515-518 (1992).

In order to isolate and/or modify the nucleic acid molecule of interest for insertion into the chosen plasmid, it is preferable to use PCR. Appropriate primers for use in PCR preparation of the sequence can be designed to isolate the required coding region of the nucleic acid molecule, add restriction endonuclease or LIC sites, place the coding region in the desired reading frame.

In a preferred embodiment a nucleic acid molecule for incorporation into an expression vector of the invention, is prepared by the use of the polymerase chain reaction as disclosed by Saiki et al (1988) *Science* 239, 487-491, using appropriate oligonucleotide primers. The coding region is amplified, whilst the primers themselves become incorporated into the amplified sequence product. In a preferred embodiment the amplification primers contain restriction endonuclease recognition sites which allow the amplified sequence product to be cloned into an appropriate vector.

The expression vectors of the invention can contain a single copy of the nucleic acid molecule described previously, or multiple copies of the nucleic acid molecule described previously.

Host Cells

Another aspect the invention provides a cell for use in the expression system of the present invention which comprises an expression vector, comprising a nucleic acid molecule as hereinbefore described. In an alternative embodiment the cell comprises an expression vector of the present invention, comprising a nucleic acid molecule described herein, or portions or fragments thereof, the vector further comprising sequences which allow it to homologously recombine into a specific site of the cell's genome.

The cell for use in the expression system of the present invention may be an aerobic cell or alternatively a facultative anaerobic cell. Preferably, the cell is a bacterial cell. Alternatively, the cell may be a yeast cell (e.g. *Saccharomyces, Pichia*), an algae cell, an insect cell, a vertebrate cell, or a plant cell.

Standard techniques for propagating vectors in prokaryotic hosts are well-known to those of skill in the art (see, for example, Ausubel et al. Short Protocols in Molecular Biology 3rd Edition (John Wiley & Sons 1995)).

To maximize recombinant protein expression, the expression vectors of the invention may express the nucleic acid molecule incorporated therein in a host bacteria with an impaired capacity to proteolytically cleave the recombinant protein (Gottesman, S., (1990) Gene Expression Technology: Methods in Enzymology 185, Academic Press, San Diego, Calif., 119-128). Alternatively, the nucleic acid molecule incorporated into an expression vector of the invention, can be modified so that the individual codons for each amino acid are those preferentially utilized in the host cell. Such alteration of nucleic acid sequences of the invention can be carried out by standard DNA synthesis techniques.

The expression vector of the present invention can be introduced into cells by conventional transformation or transfection techniques.

"Transformation" and "transfection", as used herein, refer to a variety of techniques known in the art for introducing foreign nucleic acids into a host cell. Transformation of appropriate cells with an expression vector of the present invention is accomplished by methods known in the art and typically depends on both the type of vector and cell. Said techniques include, but are not limited to calcium phosphate or calcium chloride co-precipitation, DEAE-dextran-mediated transfection, lipofection, chemoporation or electroporation.

Techniques known in the art for the transformation of host cells are disclosed in for example, Sambrook et al (1989) Molecular Cloning, A Laboratory Manual, Cold Spring Harbor Laboratory, Cold Spring Harbor, N.Y.; Ausubel et al (1987) Current Protocols in Molecular Biology, John Wiley and Sons, Inc., NY; Cohen et al (1972) Proc. Natl. Acad. Sci. USA 69, 2110; Luchansky et al (1988) Mol. Microbiol. 2, 637-646. All such methods are incorporated herein by reference.

Successfully transformed cells, that is, those cells containing the expression vector of the present invention, can be identified by techniques well known in the art. For example, cells transfected with the expression vector of the present invention can be cultured to produce the β-dystroglycan protein. Cells can be examined for the presence of the expression vector DNA by techniques well known in the art. Alternatively, the presence of the β-dystroglycan protein, or portion and fragments thereof can be detected using antibodies which hybridize thereto.

In a preferred embodiment the invention comprises a culture of transformed (recombinant) cells. Preferably the culture is clonally homogeneous.

The recombinant cell can contain a single copy of the expression vector described previously, or alternatively, multiple copies of the expression vector.

Antibodies

In one embodiment of the invention an antibody is provided, or at least an effective binding part thereof, which binds to a mutant β-dystroglycan polypeptide according to the invention, i.e. amino acid residues 654-895 of SEQ ID NO:2, more preferably that binds to the mutated PPxY domain of SEQ ID NO:2.

In one embodiment, the "at least an effective binding part" of the antibody is an antibody fragment. The antibody fragment may be, but is not limited to, a fab fragment, a F(ab')2 fragment, or a fragment produced by a fab expression library.

In one embodiment, the antibody or antibody fragment is a monoclonal antibody, a humanised antibody, a chimeric antibody or a single chain antibody, or an epitope binding fragment thereof.

The term "antibody" as used herein refers to immunoglobulin molecules and immunologically active portions thereof, i.e., molecules that contain an antigen binding site which specifically binds an antigen, such as a β-dystroglycan. A molecule which specifically binds to β-dystroglycan is a molecule which binds β-dystroglycan, but does not substantially bind other molecules in a sample, e.g., a biological sample, which naturally contains β-dystroglycan. Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

The antibody may be a polyclonal or a monoclonal antibody that binds β-dystroglycan. As used herein, the term "monoclonal antibody" refers to a population of antibody molecules that contain only one species of an antigen binding site capable of immunoreacting with a particular epitope of β-dystroglycan. A monoclonal antibody composition thus typically displays a single binding affinity for a particular β-dystroglycan protein with which it immunoreacts.

Preferably, the antibody is humanised. A humanised monoclonal antibody to a β-dystroglycan polypeptide is produced as a fusion polypeptide in an expression vector suitably adapted for transfection or transformation of prokaryotic or eukaryotic cells. In a further embodiment of the invention, said antibody is humanised by recombinant methods to combine the complimentarity determining regions of said antibody with both the constant (C) regions and the framework regions from the variable (V) regions of a human antibody.

Preferably, said antibody is provided with a marker including a conventional label or tag, for example a radioactive and/or fluorescent and/or epitope label or tag.

Alternatively, said antibody is a chimeric antibody. Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is desirable when using therapeutic antibodies in the treatment of diseases. Humanised antibodies are designed to have less "foreign" antibody regions and are therefore thought to be less immunogenic than chimeric antibodies.

In one embodiment, the antibody, or at least an effective binding part thereof (e.g. an antibody fragment), specifically binds to a β-dystroglycan polypeptide comprising a mutated PPxY domain, wherein the mutated PPxY domain is incapable of undergoing tyrosine phosphorylation. Most preferably, the antibody or at least an effective binding part thereof, specifically binds to a β-dystroglycan polypeptide comprising a mutated PPxY domain, wherein the mutated PPxY domain is incapable of undergoing tyrosine phosphorylation (e.g. the polypeptide shown in SEQ ID NO: 2 or SEQ ID NO:4 or amino acid residues 654-895 of SEQ ID NO:2) and does not bind to wildtype β-dystroglycan polypeptide (e.g. the polypeptide shown in SEQ ID NO: 1 or SEQ ID NO:3).

In an alternative embodiment, the antibody, or at least an effective binding part thereof (e.g. an antibody fragment), specifically binds to a PPxY domain of a wildtype β-dystroglycan polypeptide (e.g. naturally occurring; e.g. the PPxY domain of the β-dystroglycan polypeptide shown in SEQ ID NO: 1 or SEQ ID NO:3) wherein the tyrosine amino acid of the PPxY domain is unphosphorylated. In other words, the antibody, or at least an effective binding part thereof, specifically binds to a wildtype β-dystroglycan polypeptide wherein the PPxY domain is unphosphorylated. The antibody etc does not necessarily have to bind to the PPxY domain per se in this context, but may bind to an epitope of a wildtype β-dystroglycan polypeptide that is only accessible when the PPxY domain is in the unphosphorylated state. The antibody, or at least an effective binding part thereof (e.g. an antibody fragment), in accordance with this aspect of the invention is useful in a method for inhibiting degradation of a β-dystroglycan polypeptide. The method may be an in vivo method or alternatively an in vitro method.

Alternatively, or in addition, the antibody, or at least an effective binding part thereof (e.g. an antibody fragment), in accordance with this aspect of the invention is useful for treating a disorder or symptom associated with reduced dystroglycan function in a subject. Relevant disorders and symptoms are discussed in detail above.

Screening Methods

In one aspect, the invention provides screening methods for identifying an agent useful in the treatment of a disorder or symptom associated with reduced β-dystroglycan function.

As used herein, in the contest of the screening assays of the invention, the terms "compound" and "agent" are used interchangeably.

In one embodiment, a method for identifying an agent useful in the treatment of a disorder or symptom associated with reduced β-dystroglycan function is provided, the method comprising the steps of: contacting a candidate agent to be tested with at least one cell expressing β-dystroglycan; determining the effect of the agent on β-dystroglycan ubiquitination in the at least one cell; wherein an agent that decreases or inhibits β-dystroglycan ubiquitination is identified as an agent that is useful in the treatment of a disorder or symptom associated with reduced β-dystroglycan function.

In an alternative embodiment, a method for identifying an agent useful in the treatment of a disorder or symptom associated with reduced β-dystroglycan function is provided, the method comprising the steps of: contacting a candidate agent to be tested with at least one cell expressing β-dystroglycan; determining the effect of the agent on phosphorylation of a PPxY domain in β-dystroglycan in the at least one cell; wherein an agent that decreases or inhibits phosphorylation of a PPxY domain in β-dystroglycan is identified as an agent that is useful in the treatment of a disorder or symptom associated with reduced β-dystroglycan function.

The screening methods can be cell free assays or cell based assays. The assays determine the ability of a candidate agent to decrease or inhibit β-dystroglycan ubiquitination or decrease or inhibit phosphorylation of a PPxY domain in β-dystroglycan, and thus be useful in the treatment of a disorder or symptom associated with reduced β-dystroglycan function.

Agents thus identified can be used to decrease or inhibit β-dystroglycan ubiquitination or decrease or inhibit phosphorylation of a PPxY domain in β-dystroglycan in a subject and therefore can be of therapeutic or prophylactic use, as identified above.

In accordance with the invention, a cell-based assay system can be used to screen for agents that are useful in the treatment of a disorder or symptom associated with reduced β-dystroglycan function. To this end, cells that endogenously express β-dystroglycan can be used to screen for compounds. Alternatively, cell lines genetically engineered to express β-dystroglycan can be used for screening purposes.

To be useful in screening assays, the host cells expressing functional β-dystroglycan should give a significant response to an agent that is capable of decreasing or inhibiting β-dystroglycan ubiquitination, or an agent that is capable of decreasing or inhibiting phosphorylation of a PPxY domain in β-dystroglycan, preferably greater than 5-fold reduction over background.

In a cell based assay system the cells expressing β-dystroglycan are exposed to a test compound (or candidate agent) or to vehicle controls (e.g., placebos). After exposure, the cells can be assayed to measure the level of β-dystroglycan phosphorylation (of the PPxY domain) or to measure the level of β-dystroglycan ubiquitination.

Standard methods are known in the art to measure phosphorylation or ubiquitination (see examples section below).

The response produced by cells that are not treated with a candidate agent can be determined and used as a control. Different types of controls may be used, and can easily be determined by a person of skill in the art.

In addition to cell based assays, non-cell based assay systems may be used to screen for agents that are useful in the treatment of a disorder or symptom associated with reduced β-dystroglycan function.

For example, soluble β-dystroglycan may be recombinantly expressed and utilized in non-cell based assays to identify compounds that decrease or inhibit β-dystroglycan ubiquitination or decrease or inhibit phosphorylation of a PPxY domain in β-dystroglycan.

The methods described above can identify agents which decrease or inhibit β-dystroglycan ubiquitination or decrease or inhibit phosphorylation of a PPxY domain in β-dystroglycan.

Agents which may be screened in accordance with the invention include, but are not limited to peptides, antibodies and fragments thereof, and other organic compounds (e.g., peptidomimetics).

Transgenic Non-Human Animals

Transgenic non-human animals may be used as animal models for a disorder or symptom associated with reduced β-dystroglycan in accordance with the invention.

Such animal models may be used as test substrates for the identification of drugs, pharmaceuticals, therapies and interventions which may be effective in treating such disorders. For example, animal models may be exposed to a compound, suspected of decreasing or inhibiting β-dystroglycan ubiquitination, phosphorylation or proteasomal degradation, at a sufficient concentration and for a time sufficient to elicit a response (e.g. a therapeutic response) in the exposed animals. The response of the animals to the exposure may be monitored by assessing the reversal of disorders associated with reduced β-dystroglycan function, such as muscular dystrophy. With regard to intervention, any treatments which reverse any disorder-like symptoms should be considered as candidates for therapeutic intervention.

In one aspect of the invention, transgenic non-human animals that express the β-dystroglycan polypeptide of the invention (i.e. a β-dystroglycan polypeptide comprising a mutated PPxY domain, wherein the mutated PPxY domain is incapable of undergoing tyrosine phosphorylation) are provided. Animals of any species, including, but not limited to, mice, zebrafish, rats, rabbits, guinea pigs, pigs, micropigs, goats, and non-human primates, e.g., baboons, monkeys, and chimpanzees may be used to generate transgenic animals in accordance with the invention.

Any technique known in the art may be used to introduce the dystroglycan transgene into animals to produce the founder lines of transgenic animals. Such techniques include, but are not limited to pronuclear microinjection (Hoppe, P. C. and Wagner, 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313321); electroporation of embryos (Lo, 1983, Mol Cell. Bio 3:1803-1814); and sperm-mediated gene transfer (Lavitrano et al., 1989, Cell 57:717-723); etc. For a review of such techniques, see Gordon, 1989, Transgenic Animals, Intl. Rev. Cytol. 115:171-229, which is incorporated by reference herein in its entirety.

The present invention provides for transgenic animals that carry the dystroglycan transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232-6236). The regulatory sequences required for such a cell-type specific activation will depend upon the particular cell type of interest, and will be apparent to those of skill in the art.

Once founder animals have been generated, (e.g. the transgenic mice referred to as $Dag1^{Y890F/Y890F}$ in the examples below) standard techniques such as Southern blot analysis or PCR techniques are used to analyze animal tissues to determine whether integration of the transgene has taken place. The level of mRNA expression of the transgene in the tissues of the founder animals may also be assessed using techniques which include but are not limited to Northern blot analysis of tissue samples obtained from the animal, in situ hybridization analysis, and RT-PCR.

The founder animals may be crossed, for example with other animal models of a relevant disorder or symptom. By way of example, the $Dag1^{Y890F/Y890F}$ mice described in the examples below may be crossed with the mdx mouse (a mouse model for duchenne muscular dystrophy) or with a mouse that is a model for another relevant disorder (e.g. known LGMD mouse models such as the null models of alpha-sarcoglycan, beta-sarcoglycan, delta-sarcoglycan and gamma-sarcoglycan protein/gene). The crossed transgenic animals may be used in further screening assays to identify candidate therapeutic agents. By way of example, a $Dag1^{Y890F/Y890F}$ LGMD mouse model may be used to screen for LGMD therapeutics. The transgenic animals also have the potential to screen for other pathways not directly related to the phosphorylation of δ-dystroglycan, such as Akt, and ERK. The Akt and ERK pathway shave been demonstrated to be aberrant in LGMD and a $Dag1^{Y890F}$ LGMD mouse model may provide a relevant model to examine the effect of regulating these pathways.

EXAMPLES

Section A: Preventing Phosphorylation of Dystroglycan Ameliorates the Dystrophic Phenotype in Mdx Mouse
Section A Materials and Methods
Generation of a $Dag1^{Y890F}$ Targeting Construct:

To generate the targeting vector a 9.8 kb XhoI-EcoRI fragment that included a portion of intron 1 and the entire exon 2 of the Dag1 gene was subcloned from Bacterial artificial chromosome (BAC) clone bmQ433-E3 (GeneService) into similarly digested pBluescript SK(+)vector. The A to T nucleotide change (underlined) corresponding to the Y890F substitution was introduced by site directed PCR mutagenesis using the forward primer (5'-ATACCGATCACCCCCTCCGTTTGTTCCCCCT-3') and reverse primer (5'-ACGGAGGGGGTGATCGGTATGGGGTCATGT-3') and the GeneTailor™ site-directed mutagenesis System (Invitrogen). A BclI site in intron 1 was used to insert the Phospho-glycerate Kinase (PGK) neomycin resistance selection cassette flanked by lox P sites which was amplified from a pPGKNeoDTA using the forward primer (5'-TAGGATCCATAACTTCGTATAATGTATGCTA-3') and reverse primer 5'-TAGGATCCATAACTTCGTATAGCATACATTA-3') containing BamHI restriction sites (underlined). In addition HpaI and XhoI sites in the vector backbone, outside the region of homology, were used to insert a PGK diphtheria toxin A (DTA) cassette for negative selection. The PGKDTA cassette was amplified from pPGKNeoDTA using forward primer 5'-TACTCGAGGACCTGCAGCCCAAGCTA-3' and reverse primer 5'-TAGTTAACTGTCCAATTATGTCACACCACA-3' containing XhoI and HpaI sites respectively.

The final targeting vector (see FIG. 1A) was verified by restriction digest and direct sequencing.

After linearization of the targeting vector using XhoI, embryonic stem (ES) cell electroporation and blastocyst injection was performed by the Mouse Engineering Services of the University of Sheffield (MESUS).

Verification of the correct recombination event within neomycin resistant protamine-Cre (42) ES cell clones was performed by Southern analysis of EcoRI and KpnI digested genomic DNA using a probe located within intron 1 (FIG. 1A). WT chromosomes resulted in a 16.4 kb EcoRI fragment and a 6.8 kb KpnI fragment (FIGS. 1A and 1B). Properly targeted chromosomes produced a smaller 5.8 kb EcoRI fragment resulting from the presence of an additional EcoRI site within the neomycin resistance cassette and a larger 8.6 kb KpnI fragment resulting from the insertion of the ~1.8 kb neomycin cassette (FIGS. 1A and 1B). Genomic DNA from positive clones and subsequent progeny was also amplified and sequenced to confirm the presence of the point mutation (FIG. 10). In male chimeras, when PC3 ES cells differentiate into spermatids, Cre recombinase is expressed and results in the excision of the floxed PGK-Neo cassette (42). Excision of the Neo cassette was confirmed in this chimera and subsequent progeny by PCR using one set of primers that flank the loxP sites as follows: forward primer 5'-ATGAGTTGGATTTCCCAGCA-3' and reverse primer 5'-ATGGCCTGGCCTAAAATGAT-3' giving rise to the following products: 104 bp in WT progeny(+); 177 bp in progeny with the neo cassette excised (Neo⁻) but retaining a single loxP site and 1872 bp (not shown) in progeny where the neo cassette is still intact (Neo⁺, FIG. 1D) and another that utilise the same forward primer and a reverse primer located in the neo gene 5'-ATCGCCTTCTATCGCCTTCT-3' giving rise to the following products 499 bp where the neo cassette is still intact and no product in WT and neo excised progeny (FIG. 1D).

Chimaeric animals were then bred to heterozygosity by crossing with C57Bl6 mice. Sequencing of the Dag1 gene in targeted heterozygotes demonstrated equal proportions of both the WT adenine and MUT thymidine bases specifying the p.Y890F substitution (FIG. 10). Breeding to homozygous WT or MUT genotypes was confirmed by PCR amplification, restriction enzyme digestion and agarose gel electrophoresis (FIG. 1E, see Genotyping section below). Homozygous WT, heterozygous $Dag1^{Y890F/+}$ and homozygous $Dag1^{Y890F/Y890F}$(MUT) mice at the specified ages were used in subsequent studies. To look at the effect of the Y890F mutation on muscle pathology in dystrophin deficient muscular dystrophy $Dag1^{Y890F/Y890F}$ mice were backcrossed with $Dmd^{mdx/mdx}$ mice, the mouse model of dystrophin deficiency (Kind Gift from Steve Laval, Newcastle) for 4 generations. Mice heterozygous for the Y890F mutation and either homozygous or hemizygous for the mdx mutation ($Dag1^{Y890F/+}/Dmd^{mdx/Y}$ or Dag1) were crossed to generate double homozygous offspring of both sexes (Dag1$^{Y890F/Y890F}$/Dmd$^{mdx/Y}$ and Dag1$^{Y890F/Y890F}$/Dmd$^{mdx/mdx}$) and male mice that were hemizygous for the mdx mutation and heterozygous for the Y890F Dag1 mutation (Dag1$^{Y890F/+}$/Dmd$^{mdx/Y}$) for use in the subsequent studies described herein.

All animals were maintained in a high health status facility at the University of Sheffield according to the UK Home Office guidelines with access to food and water ad libidum. All animal studies were approved by both the ethical committee at the University of Sheffield and the UK Home Office.

Genotyping:

Mouse ear biopsies were lysed overnight at 55° C. in tail lysis buffer (50 mM TrisHCl pH 8.5; 2 mM EDTA pH 8; 0.5% Tween; 300 mg/ml Proteinase K). The following day the lysate was diluted four fold with water and 2 ml used for genotyping by PCR. Genotyping for Dag1$^{Y890F/Y890F}$ mutants was performed by PCR amplification of a 107 bp fragment of the Dag1 gene using the forward primer 5'-ATACCGATCACCCCCTACGT-3' and reverse primer 5'-CGGTCTCTACAGACAACAC-3'. PCR products were digested with SnaBI restriction enzyme (New England Bio-Labs, Ipswich, Mass., USA) and subjected to 3.5% agarose gel electrophoresis. PCR fragments containing the Y890F mutation are undigested by SnaBI (107 bp), whereas WT fragments are digested (89 bp)(FIG. 1E). Genotyping for the mdx point mutation was performed by PCR amplification of a 157 bp fragment of the Dmd gene using the forward primer 5'-GCAAAGTTCTTTGAAAGGTCAA-3' and the reverse primer 5'-CACCAACTGGGAGGAAAGTT-3'. PCR products were digested with HincII restriction enzyme (New England Biolabs). PCR fragments containing the mdx point mutation are undigested by HincII whereas WT fragments are digested (137 bp) FIG. 1E.

Histology and Pathophysiology:

Samples of quadriceps muscle were dissected from 4-6 week old animals covered in optimal cutting temperature (OCT) compound (VWR International) and frozen in liquid nitrogen cooled isopentane. Serial transverse cryosections were cut using a Bright 3500 cryostat and mounted on positively charged glass slides (VWR International). 8 µm cryosections were fixed in 3% acetic acid for 2 min and briefly rinsed in tap water before staining in Gills haematoxylin (Fisher Scientific, Fair Lawn, N.J.) for 2 min. Sections were rinsed briefly in tap water to remove excess stain then placed in 1% acid alcohol for ~5 s. Sections were rinsed in tap water then in 5% Scott's solution for ~5 s before a final rinse in tap water. Sections were then stained with eosin for 90 s (Sigma-Aldrich) rinsed in tap water and mounted using Hydromount (National Diagnostics).

Similarly prepared 6 µm cryosections were also labelled for individual components of the dystrophin glycoprotein complex using the following antibodies: anti-αDG (VIA4-1) (1:50, 4° C., Upstate biotechnology), anti-βDG (Mandag2, 1:10, 4° C.), anti-αSG (1:100, 23° C., Novocastra), anti-βSG (1:50, 23° C., Novocastra), anti-laminin-α2 (1:100, 23° C., ENZO life sciences), anti-utrophin (Rab5 rabbit polyclonal c-terminal, 1:4000, 23° C.), anti-pan plectin #46 (1:200, 4° C., a gift from Gerhard Wiche, Vienna), anti-dystrophin (DYS1, 1:20 4° C., Novocastra), anti-sarcospan (PGM2, 1:50 4° C., BioServUK Ltd, UK). The PGM2 Rabbit polyclonal antibodies to murine Sspn were raised using a synthetic peptide (Sspn aa 3-16, GenBank accession number U02487, SI-Biologics Ltd, UK). Antibodies were affinity purified from rabbit serum before use.

A mouse on mouse kit sold under the trademark M.O.M.™ Kit (Vector, Burlingame, Calif.) was used with all primary mouse antibodies and the manufacturer's protocol was followed. When using rabbit and rat antibodies, sections were blocked in PBS containing 3% BSA, 0.5% Triton X-100 and 2% FBS for 1 hr at room temperature and incubated with primary antibodies under humidified conditions as above. Sections were washed three times for two min each in PBS and incubated with secondary antibodies: Fluorescein conjugated anti-rabbit/rat IgG at 1:100 for 1 hr at room temperature in darkness (Vector). Sections were washed again as before and mounted with Hydromount (national diagnostics, Atlanta, Ga., USA) containing 1% DABCO (Sigma-Aldrich). Fluorescence was visualized using a microscope sold under the trademark ZEISS® AXIOSKOP® 2 and images were captured using software sold under the trademark QCAPTURE®.

The number of fibres with centrally placed nuclei was determined by staining sections of quadriceps muscle with an anti-laminin-α2 antibody (as above) which highlights the sarcolemma and allows delineation of individual fibres. The secondary antibody used was a Fluorescein conjugated anti-rat IgG (Vector) and was incubated with sections at 1:100 for RT at 1 hr, sections were then mounted with Hydromount containing 1% DABCO and DAPI (Molecular Probes) to stain the nuclei. Images of laminin-α2 staining of sarcolemma and DAPI staining of nuclei were merged in software sold under the trademark PHOTOSHOP® CS5 and central nuclei were counted using cell counter in Image J 64. Analysis and statistical data was calculated in software sold under the trademark Graphpad PRISM®.

Sarcolemmal Integrity:

4-6 week old animals were injected intraperitonealy with 0.05 mg/g Evans Blue Dye (Sigma Aldrich) diluted to 10 mg/ml in sterile PBS. 16 h later the quadriceps and diaphragm were excised, frozen and cryosectioned as described above. The uptake of Evans blue dye was assessed by fluorescence microscopy (microscope detailed).

All animals had a sample of blood taken from a superficial tail vein. The whole blood was allowed to coagulate at room temperature for 60 min before being stored at +4° C. for 1 hr prior to centrifugation at 800 g for 10 min. The serum was removed and either assayed for creatine kinase immediately or stored in aliquots at −80° C. Serum from animals homozygous for the mdx point mutation were used diluted 1:100 with sample buffer, serum from all other animals were used diluted 1:20. Levels of serum creatine kinase were measured in duplicate samples with a commercially available CK ELISA kit (Uscn Life Science Inc. Wuhan, P.R. China) and the manufacturer's directions followed. The plate was read on at 450 nm on a plate reader sold under the trademark FLUOSTAR® OPTIMA (BMG-LABTECH Gmbh, Ortenberg, Germany) and expressed as U/L.

In Vivo Muscle Physiology:

Mice were surgically prepared as described previously (20, 43). Normothermia was maintained throughout the procedure by placing the animal on a heat pad (Harvard Apparatus, Edenbridge, UK) and under a light source. The TA tendon was attached to the lever arm of a 305B dual-mode servomotor transducer (Aurora Scientific, Aurora, Ontario, Canada) via a loop of 4-0 braided silk and a custom made steel s-hook. The sciatic nerve was placed over a bipolar platinum electrode. The muscle was stimulated via supramaximal square-wave pulses of 0.02 ms (701A stimulator; Aurora Scientific), and data acquisition and servomotor control were conducted using a Lab-View-based DMC program (Dynamic muscle control and Data Acquisition; Aurora Scientific).

Isometric Force Measurement:

5 stimulations at a frequency of 50 Hz were used to induce submaximal contractions in the TA muscle as a warm up. The muscle's optimum length ($L_o$) was then determined by measuring a series of twitches at increasing resting tensions. The resting tension that produced the strongest twitch was then used throughout. To allow the force-frequency relationship to be determined isometric contractions were induced by a series of stimulations at 10, 30, 40, 50, 80, 100, 120, 150 and 180 Hz delivered 1 minute apart. The maximum isometric tetanic force ($P_o$) was determined from the plateau of the force-frequency curve. Muscle length was measured using digital callipers. Muscle cross-sectional area was estimated using the following formula: TA weight (g)/(TA fibre length (cm)×muscle density (g/cm³)). Where TA fibre length is $L_o$×0.6 cm and muscle density is 1.06 g/cm³. The specific force (N/cm2) was then calculated by dividing $P_o$ by TA muscle cross-sectional area.

Eccentric Contraction Protocol:

After completing the final isometric contraction the muscle was allowed to rest for 5 minutes before the eccentric contraction protocol was initiated. A tetanic contraction was induced using a stimulus of 120 Hz for 700 ms. During the last 200 ms of this contraction the muscle is stretched by 10% of $L_o$ at a velocity of 0.5 $L_o$ s$^{-1}$ and relaxed at −0.5 $L_o$s$^{-1}$. The isometric tension recorded prior to the first stretch is used as a baseline. The muscle is then subjected to 10 eccentric contractions separated by a 2 minute rest period to avoid the confounding effect of muscle fatigue. The isometric tension prior to each stretch is recorded and expressed as a percentage of the baseline tension. The mouse is then euthanised and the muscle is carefully removed and weighed.

In Vitro Assays and Western Blotting

Cell Surface Biotinylation Assays:

H2kb-tsA58 mouse myoblasts (18) maintained as described previously (44), were placed on ice, washed three times in chilled PBS and incubated for 30 minutes with 0.5 mg/ml Sulfo-NHS-SS-Biotin (Thermo Scientific) in PBS on ice. Cells were washed three times with serum free media to remove uncoupled biotin and returned to 37° C. to allow endocytosis to proceed. At various time points cells were placed on ice and washed twice in chilled MesNa stripping buffer (50 mM Tris-HCL pH 8.6, 100 mM NaCl, 1 mM EDTA), followed by 3×20 min washes in chilled MesNa stripping buffer with 0.2% BSA (w/v) and 100 mM MesNa (Sigma) added fresh. Cells were then washed in chilled PBS containing 500 mM iodoacetamide (Sigma) and left on ice for 10 minutes, before being washed a further three times in chilled PBS before lysis in radioimmunoprecipitation buffer (6). As a control for stripping, the experiment was repeated as above, except the cells were not incubated at 37° C. but were stripped immediately after biotinylation and washing with serum free media. Samples were analysed by SDS-PAGE and western blotting for phosphorylated and non-phosphorylated β-dystroglycan and transferrin receptor as control. SDS-PAGE and western blotting of muscle samples was carried out as below described previously (6, 22, 45).

Quantification of Muscle Proteins:

Hamstring muscle was snap frozen in liquid nitrogen and stored at −80° C. prior to use. Approximately 100 mg of tissue was weighed, ground to a powder under liquid nitrogen, resuspended in RIPA buffer (50 mM Tris-HCl pH 7.5, 150 mM NaCl, 1 mM EGTA, 1 mM EDTA, 1% Triton X-100, 0.5% sodium deoxycholate, 0.1% SDS, 1 mM azide, 1 mM sodium orthovanadate, 5 mM sodium fluoride, 1 mM PMSF, 10 μM TPCK, 10 μM leupeptin, 1 μM pepstatin, 10 μg/ml aprotinin, 1 mM benzamidine) at a ratio of 1 ml per 100 mg of tissue and homogenised in a dounce homogeniser for 10 strokes. Samples were incubated on a roller for 30 min at 4° C., before sonicating and centrifuging at 15000 g for 15 min. Supernatant was resuspended in Laemli sample buffer, boiled for 10 min and 30 μl was run out on 4-15% polyacrylamide gels sold under the trademark CRITERION™ TGX™ (Bio-Rad). Following transfer and blotting as above, chemiluminescence signals were imaged on an image capture system sold under the trademark CHEMIDOC™ XRS+ (Bio-Rad). Quantification was carried out in software sold under the trademark IMAGE LAB™ (Bio-Rad) using volume measurements for each band with rolling disk background subtraction (diameter 10 mm). Values were normalized against concavalin A lectin signal and represented as a ratio of the average wild type signal for each antibody. Primary Antibodies; β-DG (43Dag1 1/50, Vector Labs), pY β-DG (1709 1/1000), utrophin (Rab5 rabbit polyclonal c-terminal 1/5000), plectin (#46 1/3000, a kind gift from Gehard Wiche), dystrophin (DYS 1/100, Novacastra) and concavalin A lectin biotin conjugate (1/2500, Vector Labs). Secondary Antibodies; Peroxidase conjugated anti-mouse raised in goat (1/10000 Sigma), peroxidase conjugated anti-rabbit raised in goat (1/20000 Sigma) and peroxidase conjugated extravidin (Sigma 1/10000).

Section A Results

Generation of a Dag1$^{Y890F}$ Mouse

In order to assess the role of Y890 in regulating dystroglycan function in vivo, a targeted substitution of tyrosine 890 to phenylalanine (Y890F) was generated in mouse using standard techniques: homologous recombination in ES cells (see FIG. 1), injection into blastocyst, selection of germline transmission of the targeting construct, breeding to homozygosity and back-crossing for 5 generations onto mdx mice. Both heterozygous and homozygous Dag1$^{Y890F}$ mice appeared normal and healthy and were born at expected Mendelian ratios. To date in mice up to 8 months old, no deleterious effect of the substitution has been noted. Western blot and immunohistochemistry analysis of heterozygous and homozygous Dag1$^{Y890F}$ revealed normal levels of total β-dystroglycan compared to wildtype, but with reduced levels of detectable pY890 β-dystroglycan in heterozygotes and an absence in homozygotes (FIG. 1G,F).

Figure 2:
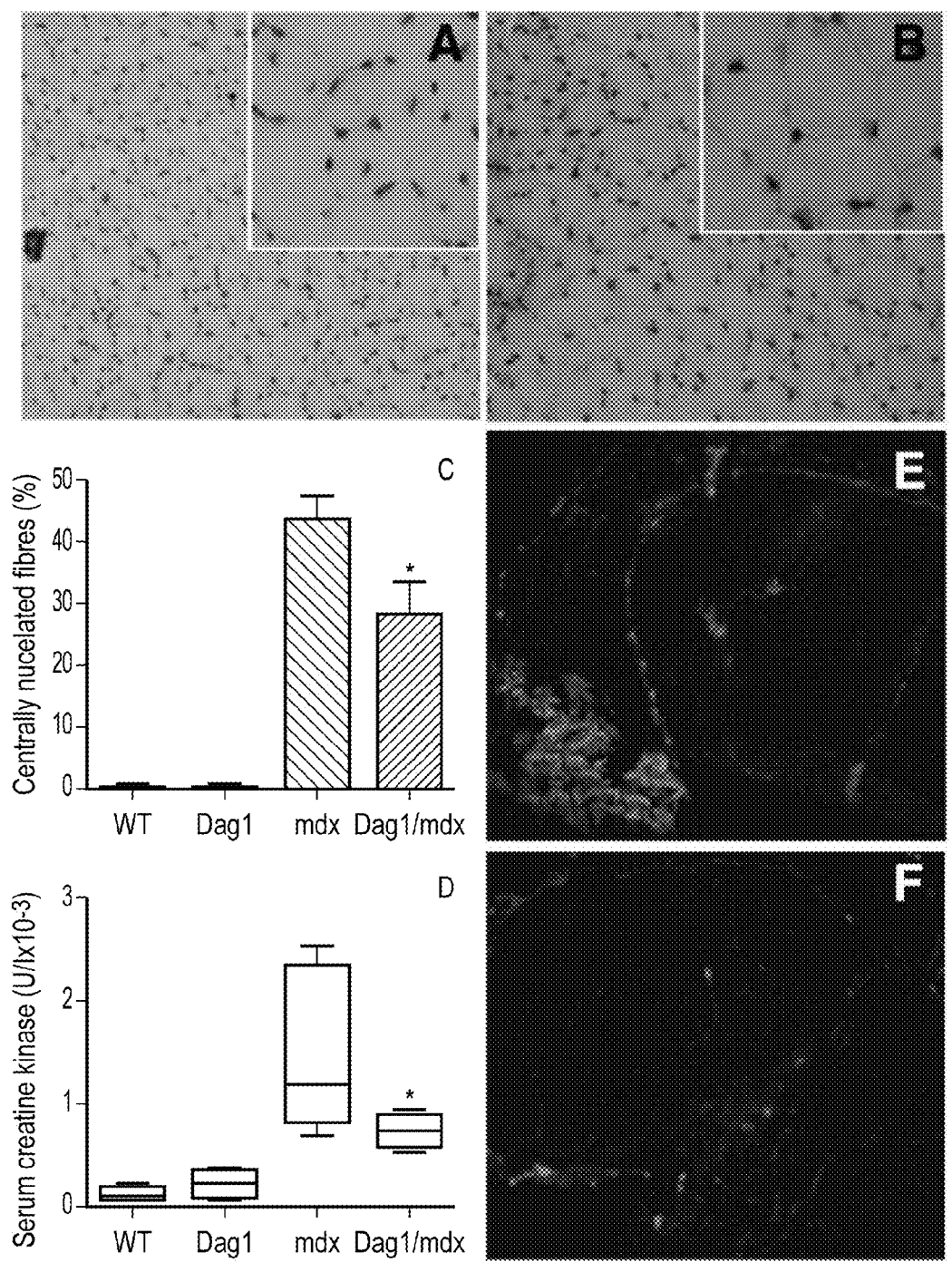
FIG. 2. Illustrates pathophysiological analysis of Dag1$^{Y890F/Y890F}$ and Dag1$^{Y890F/Y890F}$/mdx muscle. Haematoxylin and eosin staining of quadriceps muscle revealed an improved muscle pathology in Dag1$^{Y890F/Y890F}$/mdx (2B and inset) compared to mdx alone (2A and inset), with larger more even fibre size and a reduction in centrally nucleated fibres (CNF). Central nucleation was quantified by counting more than 100 fibres per section from 3 different animals of the indicated genotype (2C). Whilst Dag1$^{Y890F/Y890F}$ had a very low number of CNF and was no different from wild-type, compared to mdx, Dag1$^{Y890F/Y890F}$/mdx showed a significant 30% reduction in CNF. Mean±sem p=0.043. Serum creatine kinase (CK) levels were similarly unaffected in Dag1$^{Y890F/Y890F}$ mice (n=4), whereas the introduction of Dag1$^{Y890F/Y890F}$ into mdx (n=4) caused a dramatic and significant 50% reduction in CK levels compared to mdx alone (n=7; 2D). In keeping with the findings in 2A-D above, qualitative analysis of muscle integrity by Evans blue dye infiltration also revealed a clear reduction in fibre damage in quadriceps femoris muscle from Dag1$^{Y890F/Y890F}$/mdx (2F) compared to mdx (2E).

Preventing Dystroglycan Phosphorylation on Tyrosine 890 Improves Muscle Pathology in Dystrophic Mice In order to assess whether the introduction of a Y890F substitution in dystroglycan had any beneficial effect on dystrophin deficiency, Dag1$^{Y890F/Y890F}$/mdx mice were generated. Samples of muscle and serum from wildtype, Dag1$^{Y890F/Y890F}$, mdx and Dag1$^{Y890F/Y890F}$/mdx mice were examined for the following markers of muscle damage: infiltration of Evans blue dye; serum creatine kinase levels and centrally nucleated fibres. The introduction of the Y890F substitution into dystroglycan by itself had no effect on pathophysiological parameters of muscle. However, when crossed with mdx, Dag1$^{Y890F/Y890F}$ caused a significant reduction in: the numbers of centrally nucleated fibres (FIGS. 2A and B); the infiltration of EBD (FIG. 2C) and the levels of serum creatine kinase (FIG. 2D). The number of fibres with centrally located nuclei was decreased by 35% and the levels of serum creatine kinase were halved when compared to mdx alone. The improvement in muscle pathophysiology in Dag1$^{Y890F/Y890F}$/mdx compared to mdx are consistent with an overall reduction in muscle damage as indicated by both the reduced infiltration of Evans blue dye into Dag1$^{Y890F/Y890F}$/mdx muscle and leakage of creatine kinase into the blood stream from Dag1$^{Y890F/Y890F}$/mdx muscle. Moreover, the reduction in central fibre nucleation likely reflects a reduction in muscle regeneration as a consequence of reduced degeneration. Therefore at the level of histopathology the Y890F substitution in dystroglycan appears to have improved significantly the dystrophic phenotype observed in mdx mice.

Preventing Dystroglycan Phosphorylation on Tyrosine 890 Restores Sarcolemmal Expression of the DGC in Dystrophic Mice.

Figure 3:
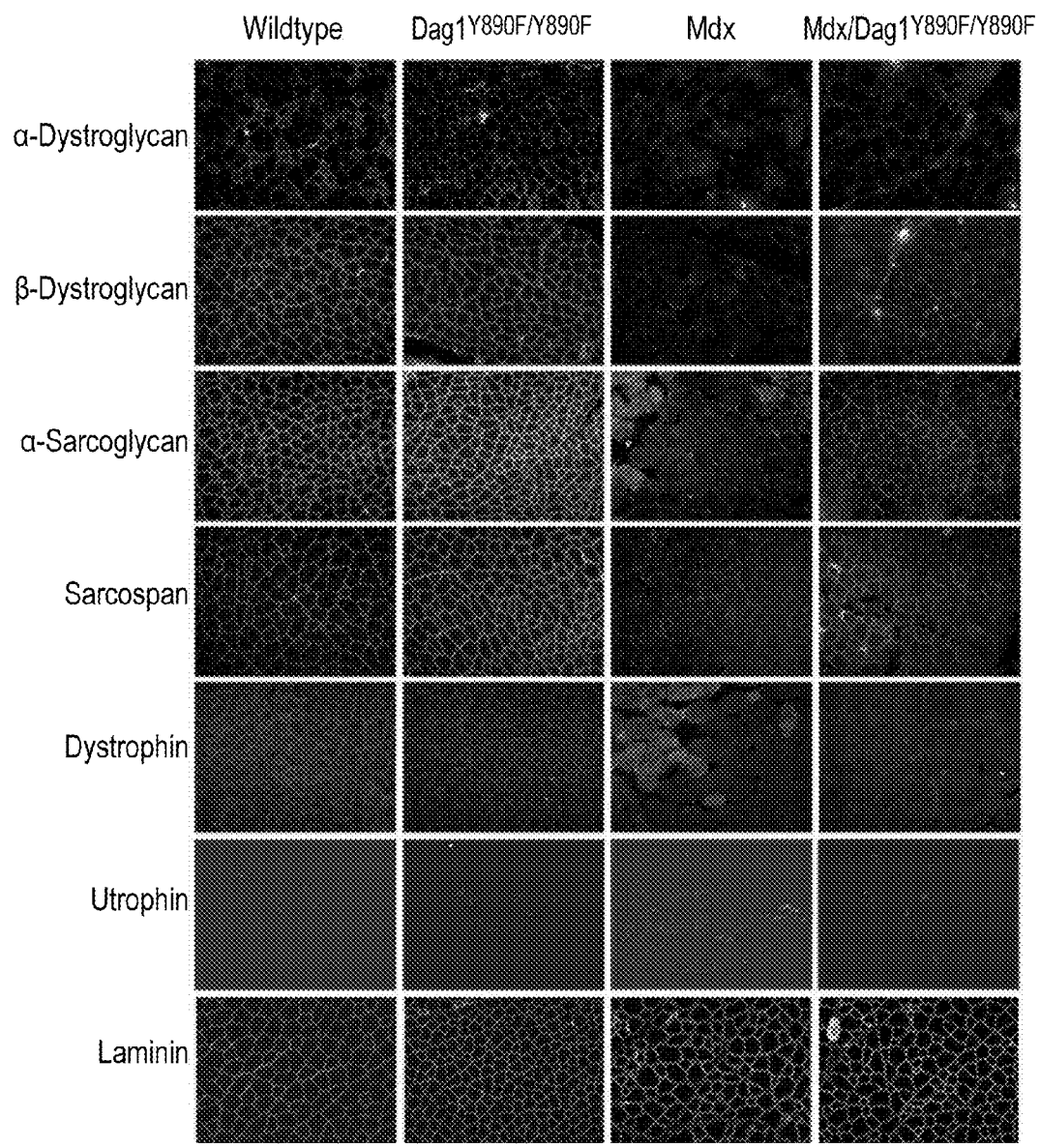
FIG. 3. Illustrates restoration of DGC components in Dag1$^{Y890F/Y890F}$/mdx muscle.

The absence of dystrophin in muscle leads the loss of the other components of the DGC from the sarcolemma (13). This in turn leads to a perturbation in the connection between the extracellular matrix and intracellular actin cytoskeleton which is thought to be one of the main reasons for the contraction induced muscle damage observed with dystrophin deficiency (14). Preventing phosphorylation of dystroglycan on tyrosine 890 had no obvious detrimental effects on the localisation of the following key members of the DGC: β- and β-dystroglycan, dystrophin, □-sarcoglycan and sarcospan (FIG. 3) or on the localisation of laminin in the extracellular matrix and utrophin in the neuromuscular junction. However, preventing phosphorylation of dystroglycan in the absence of dystrophin i.e. in Dag1$^{Y890F/Y890F}$/mdx muscle restored β- and β-dystroglycan, □-sarcoglycan and sarcospan to the sarcolemma (FIG. 3). Laminin was maintained in the sarcolemma of Dag1$^{Y890F/Y890F}$/mdx muscle at similar levels to those found in wild-type and mdx muscle (FIG. 3). In previous studies sarcolemmal utrophin was shown to be upregulated in DMD and mdx (15, 16). In the Dag1$^{Y890F/Y890F}$/mdx muscle sarcolemma however, utrophin staining returned to the more restricted neuromuscular junction distribution seen in wild-type muscle (FIG. 3). Therefore, in the absence of dystrophin the Y890F substituted dystroglycan was not only protected from degradation but also contributed to the preservation of other DGC components. Interestingly the Y890F substituted dystroglycan did not support the extrasynaptic localisation of utrophin seen in mdx alone. The staining of muscle sections with laminin gave the impression that there was an increase in the number of smaller muscle fibres in the Dag1$^{Y890F/Y890F}$ mice. Quantification of fibre size did reveal an approximate 25% reduction in minimum Ferret's diameter in Dag1$^{Y890F/Y890F}$ mice but this was not associated with any apparent change in fibre type based on assessment of glycolytic activity nor any change in specific force (FIGS. 8 to 10).

Although from the immunofluorescence analysis there are clear changes in both the apparent amounts and localisation of DGC components (FIG. 3). Quantification of actual protein levels by western blotting suggest that most of the changes observed by immunofluorescence are due to either loss of protein by degradation (in the case of mdx) or redistribution of protein within the muscle fibre rather than any actual increase in protein synthesis in the case of Dag1$^{Y890F/Y890F}$/mdx (FIG. 4). As expected from their respective genotypes, Dp427 dystrophin was absent from mdx and Dag1$^{Y890F/Y890F}$/mdx mice, and pY890 β-dystroglycan was not detectable in Dag1$^{Y890F/Y890F}$ or Dag1$^{Y890F/Y890F}$/mdx mice. Whilst there was an apparent change in unphosphorylated β-dystroglycan levels in the different mice this was to be expected. Both of the antibodies most commonly used to detect β-dystroglycan (43DAG/8D5 and MANDAG2) have Y890 in their epitope ((6) and FIG. 11) so are sensitive to the Y890F substitution. Attempts to generate antisera against a Y890F substituted peptide were not successful. Moreover it is well documented that β-dystroglycan levels are reduced in mdx though not absent (see (17) for example). As expected utrophin levels appear increased in mdx mice, however western blot analysis suggests an increase in Dag1$^{Y890F/Y890F}$ and Dag1$^{Y890F/Y890F}$/mdx mice too (FIG. 4A). Utrophin is apparent at NMJ in all mice (FIG. 3), but despite the apparent upward trend in total utrophin levels in Dag1$^{Y890F/Y890F}$. mdx and Dag1$^{Y890F/Y890F}$/mdx (FIG. 4C), a redistribution of utrophin to the sarcolemma is only apparent in mdx (FIG. 3).

In Vitro Analysis of pY890 β-Dystroglycan

Western blotting of mouse muscle with an antibody against pY890 β-dystroglycan (antibody 1709 (5)) revealed as expected a complete absence of β-DG phosphorylation on tyrosine 890 in muscle samples (FIG. 4), this not only verified the genetic change at the protein level, but provided further evidence for the specificity of our pY890 antiserum (see also FIG. 11). However to further confirm the fate of phosphorylated β-DG in muscle cells we carried out surface biotinylation experiments to determine the role of β-dystroglycan phosphorylation in the internalisation process. Previous analysis of dystroglycan function by microscopy in myoblast cells has revealed a phosphorylation-dependent internalisation of β-dystroglycan in response to constitutive Src activation (7). In order to more rigorously determine the role of dystroglycan phosphorylation on tyrosine 890 in this process, we analysed the fate of dystroglycan in H2k myoblast cells (18) over time using a cell surface biotinylation assay. We monitored non-phosphorylated β-dystroglycan with the monoclonal antibody MANDAG2 (19) which is sensitive to the phosphorylation of β-dystroglycan at Y890 (6), and monitored β-dystroglycan phosphorylated at Y890 with antibody 1709 (5) which is specific for Y890 phosphorylated dystroglycan and does not detect unphosphorylated β-dystroglycan (FIG. 11). Following cell-surface biotinylation, in contrast to non-phosphorylated β-dystroglycan which was detected on the membrane only and not in the internalised fraction, tyrosine phosphorylated β-dystroglycan was detected at the cell surface and in the cytosol (FIG. 5A). Furthermore, there was a time-dependent decrease in the amount of cell surface phosphorylated β-dystroglycan and a concomitant increase in cytosolic phosphorylated β-dystroglycan (FIG. 5A). These data suggest therefore that phosphorylation of β-dystroglycan on tyrosine 890 is a signal for the internalisation and potentially the degradation of β-dystroglycan. In support of this, immunofluorescence localisation of intracellular vesicles containing β-dystroglycan with either MANDAG2 or 1709 antibodies revealed differing cellular distributions with respect to each other and to transferrin receptor containing endocytic vesicles (FIG. 5B-D).

Preventing Dystroglycan Phosphorylation on Tyrosine 890 Confers Partial Protection Against Contraction Induced Injury in Dystrophic Mice.

Given the marked improvement in histopathology and the clear restoration of DGC components in mdx mice expressing Y890F dystroglycan, we examined the extent of any functional improvement in mouse muscle. To assess the functional benefit of preventing dystroglycan phosphorylation on tyrosine 890, TA muscles from anaesthetised Dag1$^{Y890F/Y890F}$/mdx (were subjected to a protocol of 10 eccentric (lengthening) contractions in situ. The protocol induced a 10% stretch during each of 10 maximal isometric contractions stimulated 2 minutes apart. Isometric tetanic force was measured prior to each stretch and expressed as a percentage of baseline isometric force.

Gene targeted Dag1$^{Y890F/Y890F}$ mice did not demonstrate a drop in isometric force during the eccentric contraction protocol (data not shown) which is similar to wild-type mice (20). When Dag1$^{Y890F/Y890F}$ mice were crossed with mdx mice a modest but highly significant improvement in resistance to eccentric contraction-induced injury was seen compared to mdx control mice of the same age (P=0.006; FIG. 6). Specifically Dag1$^{Y890F/Y890F}$/mdx mice were significantly stronger than control mice after eccentric contractions 5, 6 and 7 (P=0.025, 0.025 and 0.040 respectively; FIG. 6). Maximum isometric specific force produced by Dag1$^{Y890F/Y890F}$/mdx mice was 13.5±0.745 N/cm$^2$ which was not significantly different from mdx control mice. There was also no significant difference in the force-frequency curves between Dag1$^{Y890F/Y890F}$/mdx and mdx mice (FIG. 10) or TA muscle size (table 1).

TABLE 1

Dag1$^{Y890F/Y890F}$/mdx TA size and force production are not significantly different to that of mdx mice. Mean ± SEM.

|  | Mouse weight (g) | TA weight (mg) | TA length (mm) | Tetanic force (N) | Specific force (N/cm$^2$) |
|---|---|---|---|---|---|
| mdx (n = 5) | 29.9 ± 0.485 | 92.7 ± 3.66 | 11.5 ± 0.116 | 1.87 ± 0.076 | 14.8 ± 0.404 |
| DAG1mdx (n = 4) | 31.9 ± 1.43 | 99.2 ± 4.36 | 11.2 ± 0.139 | 1.86 ± 0.036 | 13.5 ± 0.745 |

The physiological studies described above demonstrate that the Y890F substitution not only reduces muscle damage and restores DGC components at the sarcolemma, but can also contribute to a modest but significant improvement in resistance to eccentric contraction in mdx muscle.

Preventing Dystroglycan Phosphorylation on Tyrosine 890 Increases Levels of Plectin in the Sarcolemma of Dystrophic Mice.

Given the role of dystroglycan as an adhesion receptor and scaffold for several cytoskeletal anchoring proteins (4) the inventors hypothesise that most likely candidate to contribute to the dystroglycan Y890F mediated rescue of the mdx phenotype would be utrophin. As discussed above utrophin is naturally upregulated in DMD and mdx muscle (15, 16), is known to bind to dystroglycan (6), and is itself protective when overexpressed in mdx muscle (21). However utrophin was not localised to the sarcolemma in Dag1$^{Y890F/Y890F}$/mdx muscle (FIG. 3). Therefore, improvement in the dystrophic phenotype i.e. decreased number of centrally located nuclei, reduction in serum creatine kinase levels and the improvement in resistance to eccentric contraction-induced injury, which was observed by preventing dystroglycan phosphorylation on tyrosine 890 cannot be attributed to an increase in sarcolemmal utrophin. Plectin is a cytolinker protein predominantly found in skeletal muscle where it is localised at the sarcolemma, z-disks and mitochondria. Plectin is also upregulated in dystrophin deficient muscle (22). Plectin interacts with β-dystroglycan at multiple sites in the cytoplasmic domain (22) and its interaction may therefore be not affected directly by phosphorylation of β-dystroglycan or by the substitution of Y890 to phenylalanine. We therefore investigated whether plectin could be providing the link between dystroglycan and the actin cytoskeleton in the absence of dystrophin in the Dag1$^{Y890F/Y890F}$/mdx muscle. Samples of wild-type, Dag1$^{Y890F/Y890F}$, mdx and Dag1$^{Y890F/Y890F}$/mdx muscle were examined for expression and localisation of plectin (FIG. 7). Consistent with our previous findings (22), plectin immunolocalisation at the sarcolemma is low in wildtype muscle but increased in mdx muscle where it appears to preferentially stain regenerating fibres i.e. those with centrally located nuclei. Surprisingly however, in Dag1$^{Y890F/Y890F}$ muscle, plectin staining of the sarcolemma appeared to be increased uniformly when compared to wildtype muscle. Furthermore, the increase in plectin staining was also observed at the sarcolemma of Dag1$^{Y890F/Y890F}$/mdx muscles when compared to mdx muscle (FIG. 7). However total plectin levels revealed by western blotting (FIG. 7E) may not accurately reflect specific changes in individual isoforms, as it is known that plectin 1f is the predominant isoform localised at the costameres at the sarcolemma (22), whereas plectin isoforms 1, 1d and 1b are associated with nuclei, Z discs and mitochondria respectively (23). Our findings support the hypothesis that phosphorylation of dystroglycan on Y890 is a key event in the aetiology of the dystrophic phenotype in the mdx mouse and that plectin is a candidate to maintain the link between the extracellular matrix and the cytoskeleton in the absence of dystrophin.

Section A Discussion

This study demonstrates that preventing phosphorylation of a key tyrosine residue on murine dystroglycan –Y890, ameliorates many of the main pathological symptoms associated with dystrophin deficiency in the mdx mouse. Muscle degeneration/regeneration was reduced as shown by a decrease in the number of centrally located nuclei, myofibre integrity was increased with a 50% reduction in serum creatine kinase levels, whilst there was also restoration of DGC components to the sarcolemma and an improvement in the resistance to eccentric contraction-induced injury. The Y890F mutation alone did not appear to have any detrimental side effects, with the only observed change from wildtype being a slight reduction in fibre diameter and an increase in plectin staining at the sarcolemma. The overt health of the Y890F knock-in mice, and the significant improvement in dystrophic pathology observed when crossed onto an mdx background, identifies dystroglycan phosphorylation as a potential therapeutic target and provides a new paradigm for the treatment of DMD. Although in this study we have used a genetic approach to remove an important phosphorylation site in dystroglycan, future therapeutic approaches would be aimed at targeting the signalling pathways that lead to the phosphorylation of dystroglycan or the subsequent degradation process.

The potential for therapeutic restoration of dystroglycan function to the sarcolemma has been assessed previously, but without success. Restoration of dystrophin or utrophin in mdx mice, by genetic, viral or chemical means is able to restore dystroglycan and other DGC components and effect a significant rescue of the dystrophic phenotype, indeed a number of therapeutic strategies are predicated on the success of this approach. In these cases however, a 'corrected' dystrophin (exon skipping strategies) a replacement dystrophin (gene and cell based approaches) or a dystrophin homologue (utrophin upregulation) is required to achieve a functional rescue, see (24, 25) for recent reviews. In all these cases there was an attempt to restore a fully functional DGC with appropriate connections between extracellular matrix and sarcolemmal cytoskeleton. Other approaches have attempted to restore the DGC by different means, including transgenic overexpression of Dp71 a short 3' product of the Dmd gene that includes the WW domain that provides interactions with dystroglycan (10, 11), or by simply overexpressing dystroglycan in order to increase the amount at the sarcolemma (12). High level overexpression of Dp71 in mdx increases DGC components at the sarcolemma but does not result in the redistribution/downregulation of utrophin, nor does it improve other aspects of the dystrophic pathology (10, 11). At first sight these data appear paradoxical, but if one considers that the level of utrophin upregulation present is no different from mdx, which in itself cannot be fully protective as there is a dystrophic phenotype. Utrophin clearly does exert some protective function, as knockout of utrophin in mdx leads to a much more severe phenotype (26, 27). However, even in the presence of some utrophin and with an increase in other DGC components Dp71 cannot make connections to the cytoskeleton and therefore does not stabilise the sarcolemma (10, 11). As the authors of both these studies discuss, restoration of the DGC is by Dp71 binding to dystroglycan and reduction of DGC component degradation.

From our studies we would further surmise that this is due to the protective effect of Dp71 binding to β-dystroglycan via the PPPY motif and reducing tyrosine phosphorylation and as a consequence dystroglycan degradation, By similar reasoning, we hypothesise that simply overexpressing dystroglycan also fails to rescue the dystrophic mdx phenotype in the same manner. Whilst elevated levels of both □- and β-dystroglycan and a significant increase in sarcolemmal localisation of these proteins have been achieved in muscle by transgenic overexpression, there was not a concomitant increase in utrophin or sarcoglycan, nor was there any improvement in dystrophic pathology (12). In this case there may be three factors which taken together explain the failure of increased dystroglycan to rescue the dystrophic phenotype: first is that even though dystroglycan levels are increased, possibly because there is not a coordinated upregulation of sarcoglycans and other DGC proteins, the complexes formed at the sarcolemma are not competent to stabilise the sarcolemma. Secondly, as in the case of Dp71 overexpression, there is no increase in a cytolinker protein such as utrophin that can provide the link to the extracellular matrix and thirdly, whilst dystroglycan levels are increased, dystroglycan may be turned over rapidly as it could be susceptible to phosphorylation mediated degradation. In the present study by contrast, dystroglycan is expressed at normal levels from its own promoter, tyrosine 890 has been substituted to phenylalanine so cannot be phosphorylated. Although utrophin levels do not remain elevated, plectin expression/localisation at the sarcolemma is increased providing a stabilising link from dystroglycan to the cytoskeleton. The data presented here describing the rescue of the dystrophic phenotype achieved in mdx by changing a single phosphorylation site in dystroglycan, represents a new paradigm in the aetiology and potential treatment of DMD.

The inventors have hypothesised that phosphorylation of dystroglycan targets it for degradation. Previous work from the Lisanti group had identified Src, but not other family kinases or FAK, as capable of phosphorylating dystroglycan on Y890 (28), and that pY890 dystroglycan was internalised into vesicular structures that colocalised with cSrc when dystroglycan and cSrc were co-expressed in Cos-7 cells (7). Furthermore immunofluorescence localisation of pY890 β-dystroglycan in normal mouse muscle revealed a punctate staining pattern in the interior of the fibres and not at the sarcolemma as seen with non-phosphorylated dystroglycan (7). Using a membrane targeted β-dystroglycan cytoplasmic domain construct, they also demonstrated that the β-dystroglycan construct was targeted to late endosomes dependent on Src phosphorylation of Y890 (7). These data are consistent with the inventors findings in myoblast cells (FIG. 5) that only endogenous phosphorylated β-dystroglycan is internalised from the membrane. The fate of internalised phosphorylated β-dystroglycan, it has not been demonstrated whether β-dystroglycan is also internalised, is presumed to be proteasomal degradation—along with other DGC components that are internalised in mdx and DMD. Based on this premise, it has been proposed that blocking the ultimate step in the pathway, namely the proteasome, might be able to restore DGC components to the sarcolemma (8). Treatment with proteasomal inhibitors does indeed restore dystroglycan and other DGC components to the membrane and in appropriate models can be demonstrated to improve muscle pathophysiology in mdx mice, explants from DMD and BMD patients and in sapje a zebrafish model of DMD (8, 9, 29-31). Our mouse genetic model also suggests that blocking the first step in the pathway—namely tyrosine phosphorylation of β-dystroglycan also has specific and beneficial effects in improving the dystrophic phenotype. Consequently appropriate therapeutic agents that inhibit Src kinase may also prove to be beneficial in treating DMD. Like proteasomal inhibitors however, clinically approved tyrosine kinase inhibitors, mostly in use as anti-cancer agents, have significant side effects. However, having identified drugable targets at two different points in a pathway leading to the loss of dystroglycan and DGC function in DMD, it should be possible to apply combinatorial therapies to achieve synergistic effects at much lower doses thus alleviating the side effects.

Utrophin upregulation occurs spontaneously to a certain extent in DMD (32, 33) and also in mdx (15, 16) where it has a clear protective effect (26, 27). Furthermore, forced expression of utrophin ameliorates the dystrophic phenotype in mdx, whether via a transgene (21), or by enhancing promoter activity pharmacologically (34). Moreover, as noted above, Dp71 overexpression in mdx protects the DGC and maintains levels of utrophin seen in mdx alone. By stabilising dystroglycan and other DGC components at the sarcolemma we therefore expected to achieve a rescue of the dystrophic phenotype in part by the actions of utrophin in anchoring the DGC to the sarcolemma. As our data show however, utrophin levels were not maintained in mdx expressing Y890F dystroglycan, but instead, plectin levels were upregulated. This unexpected finding raises some interesting questions: when the DGC is restored by preventing dystroglycan phosphorylation what are the mechanisms that lead to the preferential increase in plectin rather than utrophin at the sarcolemma, and how can plectin apparently effect such a rescue of the mdx phenotype? From the phenotypes of epidermolysis bullosa simplex with muscular dystrophy, we know that mutations in plectin contribute to sarcolemmal integrity (35-37), and that plectin is enriched at the sarcolemma in DMD (38) and plectin 1f specifically in the costameres of mdx mice (22). More recently a mutation in exon 1f of plectin has been shown to give rise to an autosomal recessive limb girdle muscular dystrophy (LGMD2) phenotype independently of any dermatological symptoms (39). Therefore plectin, like utrophin, is one of the family of large cytolinker proteins that contribute to sarcolemmal integrity and are naturally upregulated, or redistributed, in a protective role in dystrophic muscle. From this brief review of plectin function in muscle, it is clear that plectin is already contributing to muscle architecture and is naturally upregulated in dystrophic conditions. But why plectin and not utrophin localisation to the sarcolemma in our Y890F/mdx model? Part of the answer may lie in the nature of the mutation that was introduced into dystroglycan in this study. Changing the WW domain interaction motif PPPY to PPPF would not be predicted to support efficient binding of the utrophin WW domain (6, 40, 41). The inventors previous biochemical analysis of plectin, dystrophin and dystroglycan interactions (22), reveals the ability of plectin to bind to two sites on dystroglycan, including one that overlaps with the dystrophin WW domain interaction site—but importantly is not itself a WW domain interaction as plectin does not contain a WW domain. As previously published, in the mdx mouse plectin can bind to dystroglycan through both interaction sites including the c-terminal PPPY motif (22). In the Y890F mouse the ability of dystrophin to interact with the mutated PPPF motif is also weakened allowing increased plectin binding. In the mdx/Y890F mouse where dystroglycan phosphorylation is prevented and is therefore stabilised at the sarcolemma, plectin interaction/recruitment at the sarcolemma is further enhanced leading to a rescue of the dystrophic phenotype. The scheme put forward in the inventors 2007 publication (see FIG. 10 in (22)) to explain the role of plectin in mdx mouse, also fits well with the role of plectin in the current mdx/Y890F mouse model. The inventors cannot rule out a role for increased utrophin levels in the rescue of the mdx phenotype, however it is unlikely that these alone are sufficient. It is possible that interactions between plectin and utrophin could replace interactions between plectin and dystrophin, but this is not supported by available utrophin localisation data in the $Dag1^{Y890F/Y890F}$ or $Dag1^{Y890F/Y890F}/$mdx muscle. Furthermore detailed examination of the interactions between plectin, dystroglycan and utrophin are clearly warranted.

Thus the inventors have developed a new model of muscular dystrophy that for the first time not only reveals the importance of dystroglycan phosphorylation in the aetiology of muscular dystrophy, but also provides a new rationale for therapeutic intervention in Duchenne muscular dystrophy. Whether combinatorial drug treatment would provide sufficient therapeutic benefit on its own remains to be tested, however the promising genetic (this study) and pharmacological (8, 9, 29-31) interventions suggest at the very least that these approaches could be powerful adjuncts to other therapies such as exon skipping or utrophin upregulation.

Section B: Tyrosine Phosphorylation of Dystroglycan Drives Ubiquitination in Tissue Culture Cells Section B Materials and Methods Tyrosine phosphatases were inhibited in myoblast cells in vitro using peroxyvanadate and samples from cells expressing HA-tagged ubiquitin were taken for immunoprecipitation and western blot analysis. Immunoprecipitation with either the HA tag, or β-dystroglycan at various time points was followed by Western blotting for the HA epitope, β-dystroglycan or tubulin as a loading control.

Section B Results

Identification of β-Dystroglycan Ubiquitination Following Protein Tyrosine Phosphatase Inhibition.

Tyrosine phosphatases were inhibited in vitro using peroxyvanadate and samples from cells expressing HA-tagged ubiquitin taken for immunoprecipitation and western blot analysis. Immunoprecipitation with either the HA tag, or β-dystroglycan and blotting for HA revealed the presence of low molecular weight ubiquitin-β-Dystroglycan fragments (degradation products) and high molecular weight ubiquitinated β-dystroglycan (FIG. 12; left panels). Time course of treatment revealed an increase in the proportion and number of ubiquitin-β-dystroglycan bands (FIG. 12; right panels lower pane). As illustrated by FIG. 12 specific pulldown of β-dystroglycan with a ubiquitin binding protein reveals that only tyrosine phosphorylated β-dystroglycan is ubiquitinated (higher band in the 'P' fraction in the right hand blot: Ubi-DG). Whereas non-phosphorylated β-dystroglycan is not recovered with the ubiquitin binding protein and is not visible as a higher band on the left hand blot.

Therefore increasing the level of dystroglycan phosphorylation by inhibiting tyrosine phosphatases also increases both the level of dystroglycan ubiquitination and the level of dystroglycan degradation.

Section C: Preventing Phosphorylation of Dystroglycan Ameliorates the Dystrophic Phenotype in Sapje Zebrafish.

Section C Materials and Methods

Zebrafish embryos were collected from group matings of heterozygous sapje ta222a (a dystrophin mutant) and homozygous for a transgene that labels all the fast muscle with GFP (actin:GFP;). At 24 hours post fertilization (hpf) embryos were dechorionated enzymatically, washed and arrayed into multiwell plates with 40 embryos per treatment (5 embryos per well). Sapje embryos are produced at normal Mendelian frequencies, so from 40 embryos we expect 10 homozygote for sapje. Compounds to be tested were added to a final concentration based on available clinical or mouse studies for EC50. All plates included negative controls. Live embryos were assayed for muscle degeneration using actin:GFP as a marker of muscle integrity in sapje fish. Fluorescent scans for GFP along the body axis of wildtype siblings or mutant fish reveal a dramatic profile of fluorescence intensity which clearly distinguished the normal muscle from damaged muscle.

Section C Results

Sapje zebrafish carry a heterozygous mutation in the dystrophin gene (46). When present as a homozygous copy, the fish exhibit a muscle disruption phenotype which is believed to be a correlate of muscular dystrophy in mammals. Consequently zebrafish embryos carrying with a homozygous sapje mutation are a useful model for drug screening for muscular dystrophy therapeutics (47). The inventors have investigated the sapje model in this regard by targeting the pathways leading to the degradation of dystroglycan. The inventors propose that tyrosine phosphorylation of b-dystroglycan leads to the internalisation of the protein and its subsequent degradation through the ubiquitin proteasomal pathway. the inventors have developed a mouse model where b-dystroglycan cannot be phosphorylated on tyrosine. When crossed with mdx mice, the dystrophic phenotype of the mdx mouse is improved significantly (48). This suggests that preventing the tyrosine phosphorylation of b-dystroglycan, in this case by direct genetic intervention, could be of therapeutic benefit. However treatment of people with Duchenne muscular dystrophy would ideally require a simple to administer drug therapy. The inventors have now demonstrated using sapje zebrafish that preventing the phosphorylation of b-dystroglycan pharmacologically using the tyrosine kinase inhibitor Dasatinib (49) improves significantly the dystrophic phenotype of the fish (FIG. 13A). The improved phenotype also correlates with a reduction in dystroglycan phosphorylation in the fish (FIG. 13B).

Qualitatively similar results, but based on less extensive data, have also been achieved with the specific Src kinase inhibitor Saracatinib (50).

As illustrated in FIG. 13C Dasatinib inhibits the phosphorylation of β-dystroglycan in dystrophic sapje zebrafish as determined by western blotting (top panel) and is demonstrated to have a significant quantifiable effect at 10 µM in reducing dystroglycan phosphorylation in sapje zebrafish larvae (middle panel). The lower panel shows a dose response curve for the effect of Dasatinib treatment on improving the dystrophic phenotype in sapje zebrafish.

In keeping with the original hypothesis, these data suggest that pharmacological inhibition of b-dystroglycan phosphorylation on tyrosine is of potential therapeutic benefit. One presumed intermediate step in the degradation of b-dystroglycan is ubiquitination which ultimately leads to the protein being targeted for ubiquitin-mediated proteasomal degradation. There are relatively few inhibitors of this pathway, however one experimental drug Pyr-41 has been shown to inhibit the ubiquitin activating enzyme E1 (51). Limited analysis of the effects of Pyr-41 on the phenotype of sapje zebrafish revealed a small but positive benefit of treatment with Pyr-41 compared to the vehicle (DMSO) alone (FIG. 14).

Previous studies in mice and explants from patients have demonstrated the benefit of proteasomal blockade in rescuing the dystrophic phenotype (8, 9, 29, 30). The inventors have recently demonstrated a similar benefit in sapje zebrafish with the proteasomal inhibitor MG132 (31) and FIG. 15. Furthermore, analysis of the dystroglycan status of sapje fish treated with MG132 reveals a significant increase on the amounts of both phosphorylated and non-phosphorylated b-dystroglycan in treated animals (FIG. 16). Qualitatively similar results, but based on less extensive data, have also been achieved with the clinically approved proteasomal inhibitor bortezomib (sold under the trademark VELCADE®).

Section C Discussion

These data demonstrate that blocking any one of the steps in the tyrosine phosphorylation-dependent ubiquitin-mediated proteasomal degradation of dystroglycan has beneficial effects in the musculature of the dystrophic sapje zebrafish. Inhibition of either the tyrosine phosphorylation, or the ubiquitination, or the degradation of b-dystroglycan each had beneficial effects. Whilst none of the drug treatments alone achieved a complete rescue, the possibility that combinations of these agents may have increased potency is extremely promising. These data therefore provide proof of principle that a combinatorial approach to the treatment of Duchenne muscular dystrophy could be achieved by the inhibition of the tyrosine phosphorylation, ubiquitination and degradation of dystroglycan in striated muscle.

Section D: Dasatinib Treatment Inhibits Dystroglycan Phosphorylation in Mouse Myoblast (Muscle Precursor) Cells As illustrated in FIG. 24, treatment of myoblast cells with the tyrosine kinase inhibitor Dasatinib reduces the levels of tyrosine phosphorylated b-dystroglycan as determined by western blotting of myoblast cell lysates (left hand panel shows 2 independent experiments). Data are shown graphically in quantified form on the right. Dasatinib inhibits significantly the tyrosine phosphorylation of b-dystroglycan and in a dose dependent manner.

Section E: Additive/Synergistic Effect of Dasatinib on the Dystrophic Phenotype of Sapje Zebrafish.

FIG. 25 shows the Additive/synergistic effect of 0.5 µM MG132 on the dose-dependent effect of Dasatinib on the dystrophic phenotype of sapje zebrafish. The addition of 0.5 µM MG132 has a potentiating effect on the actions of Dasatinib at 0.062, 0.125 and 0.25 µM.

The data demonstrates that inhibiting two different parts of the same pathway involved in the loss of dystroglycan—namely tyrosine phosphorylation and proteasomal degradation have a more than additive, i.e. a synergistic effects, and thereby demonstrates the efficacy of a combinatorial approach.

Section F: Dose Dependent Rescue of the Dystrophic Phenotype in Sapje Fish by the Proteasomal Inhibitor Bortezomib FIG. 26 illustrates dose dependent rescue of the dystrophic phenotype in sapje fish by the proteasomal inhibitor bortezomib (sold under the trademark VELCADE®).

Figure 27:
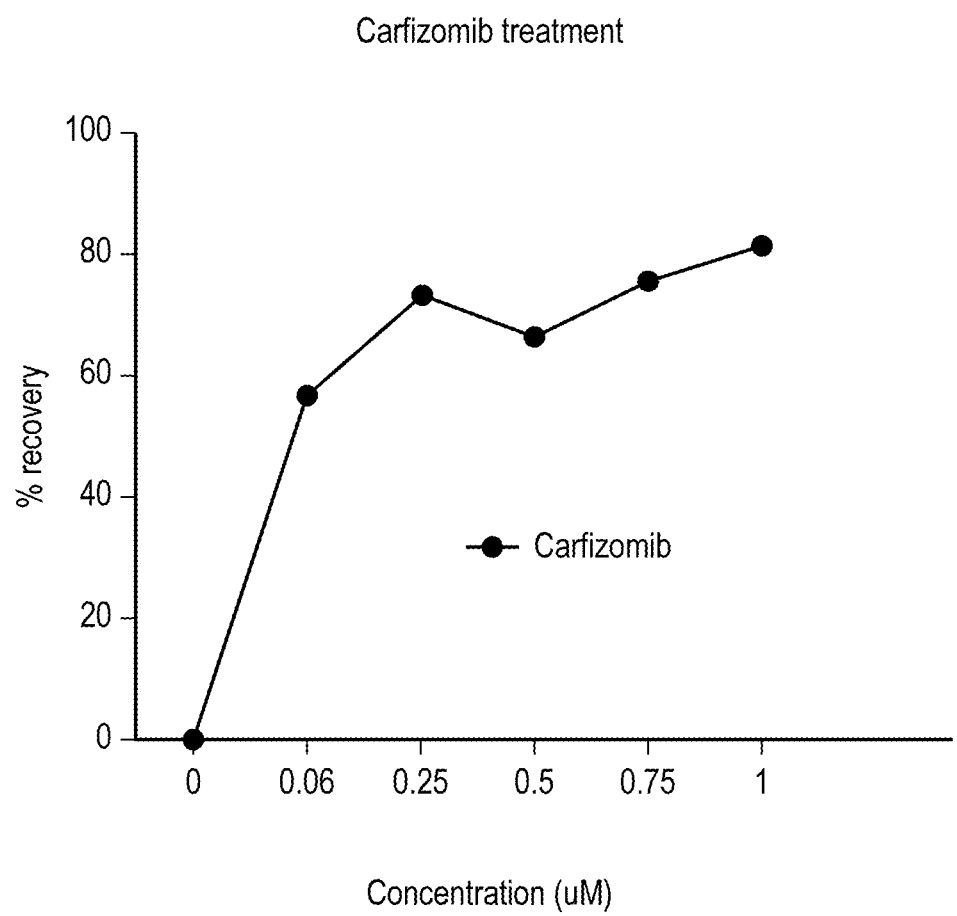

Section G: Dose Dependent Rescue of the Dystrophic Phenotype in Sapje Fish by the Proteasomal Inhibitor Carfilzomib FIG. 27 illustrates dose dependent rescue of the dystrophic phenotype in sapje fish by the proteasomal inhibitor Carfilzomib Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

1. Ervasti, J. M. and Campbell, K. P. (1993) A role for the dystrophin glycoprotein complex as a transmembrane linker between laminin and actin. *J. Cell. Biol.*, 112, 809-823.
2. Ervasti, J. M. (2003) Costameres: the Achilles' Heel of Herculean Muscle. *J. Biol. Chem.*, 278, 13591-13594.

3. Winder, S. J. (2001) The complexities of dystroglycan. *Trends Biochem. Sci.*, 26, 118-124.
4. Moore, C. and Winder, S. J. (2010) Dystroglycan versatility in cell adhesion: a tale of multiple motifs. *Cell Corn. Signal.*, 8, 3.
5. Ilsley, J. L., Sudol, M. and Winder, S. J. (2001) The interaction of dystrophin with b-dystroglycan is regulated by tyrosine phosphorylation. *Cell. Signal.*, 13, 625-632.
6. James, M., Nuttall, A., Ilsley, J. L., Ottersbach, K., Tinsley, J. N., Sudol, M. and Winder, S. J. (2000) Adhesion-dependent tyrosine phosphorylation of b-dystroglycan regulates its interaction with utrophin. *J. Cell Sci.*, 113, 1717-1726.
7. Sotgia, F., Bonuccelli, G., Bedford, M., Brancaccio, A., Mayer, U., Wilson, M. T., Campos-Gonzalez, R., Brooks, J. W., Sudol, M. and Lisanti, M. P. (2003) Localization of Phospho-b-dystroglycan (pY892) to an Intracellular Vesicular Compartment in Cultured Cells and Skeletal Muscle Fibers in Vivo. *Biochem.*, 42, 7110-7123.
8. Bonuccelli, G., Sotgia, F., Schubert, W., Park, D. S., Frank, P. G., Woodman, S. E., Insabato, L., Cammer, M., Minetti, C. and Lisanti, M. P. (2003) Proteasome Inhibitor (MG-132) Treatment of mdx Mice Rescues the Expression and Membrane Localization of Dystrophin and Dystrophin-Associated Proteins. *Am J Pathol*, 163, 1663-1675.
9. Assereto, S., Stringara, S., Sotgia, F., Bonuccelli, G., Broccolini, A., Pedemonte, M., Traverso, M., Biancheri, R., Zara, F., Bruno, C. et al. (2006) Pharmacological Rescue of the Dystrophin Complex in Duchenne and Becker Skeletal Muscle Explants by Proteasomal Inhibitor Treatment. *Am J Physiol Cell Physiol*, 290, C577-582.
10. Cox, G. A., Sunada, Y., Campbell, K. P. and Chamberlain, J. S. (1994) Dp71 can restore the dystrophin-associated glycoprotein complex in muscle but fails to prevent dystrophy. *Nature Genet.*, 8, 333-339.
11. Greenberg, D. S., Sunada, Y., Campbell, K. P., Yaffe, D. and Nudel, U. (1994) Exogenous Dp71 restores the levels of dystrophin-associated proteins but does not alleviate muscle damage In mdx mice. *Nature Genet.*, 8, 340-344.
12. Hoyte, K., Jayasinha, V., Xia, B. and Martin, P. T. (2004) Transgenic Overexpression of Dystroglycan Does Not Inhibit Muscular Dystrophy in mdx Mice. *Am J Pathol*, 164, 711-718.
13. Ervasti, J. M., Ohlendieck, K., Kahl, S. D., Gayer, M. G. and Campbell, K. P. (1990) Deficiency of a glycoprotein component of the dystrophin complex in dystrophic muscle. *Nature*, 345, 315-319.
14. Batchelor, C. and Winder, S. (2006) Sparks, signals and shock absorbers: how dystrophin loss causes muscular dystrophy. *Trends Cell Biol.*, 16, 198-205.
15. Nguyen, T., Ellis, J. M., Love, D. R., Davies, K. E., Gatter, K. C., Dickson, G. and Morris, G. E. (1991) Localization of the DMDL gene-encoded dystrophin-related protein using a panel of nineteen monoclonal antibodies: Presence at neuromuscular junctions, in the sarcolemma of dystrophic skeletal muscle in vascular and other smooth muscles, and in proliferating brain cell lines. *J. Cell Biol.*, 115, 1695-1700.
16. Matsumura, K., Ervasti, J. M., Ohlendieck, K. and al., e. (1992) Association of dystrophin-related protein with dystrophin-associated protein in mdx mouse muscle. *Nature*, 360, 588-591.
17. Cluchague, N., Moreau, C., Rocher, C., Pottier, S., Leray, G., Cherel, Y. and Le Rumeur, E. (2004) beta-Dystroglycan can be revealed in microsomes from mdx mouse muscle by detergent treatment. *FEBS Letters*, 572, 216-220.
18. Morgan, J. E., Beauchamp, J. R., Pagel, C. N., Peckham, M., Ataliotis, P., Jat, P. S., Noble, M. D., Farmer, K. and Partridge, T. A. (1994) Myogenic Cell Lines Derived from Transgenic Mice Carrying a Thermolabile T Antigen: A Model System for the Derivation of Tissue-Specific and Mutation-Specific Cell Lines. *Dev. Biol.*, 162, 486-498.
19. Pereboev, A., Ahmed, N., Man, N. t. and Morris, G. (2001) Epitopes in the interacting regions of beta-dystroglycan (PPxY motif) and dystrophin (WW domain). *Biochim. Biophys. Acta*, 1527, 54-60.
20. Sharp, P. S., Bye-a-Jee, H. and Wells, D. J. (2011) Physiological Characterization of Muscle Strength With Variable Levels of Dystrophin Restoration in mdx Mice Following Local Antisense Therapy. *Mol Ther*, 19, 165-171.
21. Tinsley, J. M., Potter, A. C., Phelps, S. R., Fisher, R., Trickett, J. I. and Davies, K. E. (1996) Amelioration of the dystrophic phenotype of mdx mice using a truncated utrophin transgene. *Nature*, 384, 349-353.
22. Rezniczek, G. A., Konieczny, P., Nikolic, B., Reipert, S., Schneller, D., Abrahamsberg, C., Davies, K. E., Winder, S. J. and Wiche, G. (2007) Plectin 1f scaffolding at the sarcolemma of dystrophic (mdx) muscle fibers through multiple interactions with β-dystroglycan. *J. Cell Biol.*, 176, 965-977.
23. Konieczny, P., Fuchs, P., Reipert, S., Kunz, W. S., Zeold, A., Fischer, I., Paulin, D., Schroder, R. and Wiche, G. (2008) Myofiber integrity depends on desmin network targeting to Z-disks and costameres via distinct plectin isoforms. *The Journal of Cell Biology*, 181, 667-681.
24. Goyenvalle, A., Seto, J. T., Davies, K. E. and Chamberlain, J. (2011) Therapeutic approaches to muscular dystrophy. *Human Molecular Genetics*, 20, R69-R78.
25. Pichavant, C., Aartsma-Rus, A., Clemens, P. R., Davies, K. E., Dickson, G., Takeda, S. i., Wilton, S. D., Wolff, J. A., Wooddell, C. I., Xiao, X. et al. (2011) Current Status of Pharmaceutical and Genetic Therapeutic Approaches to Treat DMD. *Mol Ther*, 19, 830-840.
26. Deconinck, A. E., Rafael, J. A., Skinner, J. A., Brown, S. C., Potter, A. C., Metzinger, L., Watt, D. J., Dickson, J. G., Tinsley, J. M. and Davies, K. E. (1997) Utrophin-dystrophin-deficient mice as a model for Duchenne muscular dystrophy. *Cell*, 90, 717-727.
27. Grady, R. M., Teng, H., Nicholl, M. C., Cunningham, J. C., Wilkinson, R. S. and Sanes, J. R. (1997) Skeletal and cardiac myopathies in mice lacking utrophin and dystrophin: a model for Duchenne muscular dystrophy. *Cell*, 90, 729-738.
28. Sotgia, F., Lee, H., Bedford, M., Petrucci, T. C., Sudol, M. and Lisanti, M. P. (2001) Tyrosine phosphorylation of b-dystroglycan at its WW domain binding motif, PPxY, recruits SH2 domain containing proteins. *Biochemistry*, 40, 14585-14592.
29. Bonuccelli, G., Sotgia, F., Capozza, F., Gazzerro, E., Minetti, C. and Lisanti, M. P. (2007) Localized treatment with a novel FDA-approved proteasome inhibitor blocks the degradation of dystrophin and dystrophin-associated proteins in mdx mice. *Cell Cycle*, 6, 1242-1248.
30. Gazzerro, E., Assereto, S., Bonetto, A., Sotgia, F., Scarff, S., Pistorio, A., Bonuccelli, G., Cilli, M., Bruno, C., Zara, F. et al. (2010) Therapeutic Potential of Proteasome Inhibition in Duchenne and Becker Muscular Dystrophies. *Am. J. Pathol.*, 176, 1863-1877.

31. Lipscomb, L., Parkin, C. A., Juusola, M. I. and Winder, S. J. (2011) The proteasomal inhibitor MG132 prevents muscular dystrophy in zebrafish. *PLoS Currents*, 3, RRN1286.
32. Karpati, G., Carpenter, S., Morris, G. E., Davies, K. E., Guerin, C. and Holland, P. (1993) Localization and quantitation of the chromosome 6-encoded dystrophin-related protein in normal and pathological human muscle. *J. Neuropathol. Exp. Neurol.*, 52, 119-128.
33. Clerk, A., Morris, G. E., Dubowitz, V., Davies, K. E. and Sewry, C. A. (1993) Dystrophin-related protein, utrophin in normal and dystrophic human fetal skeletal muscle. *Histochem. J.*, 25, 554-561.
34. Tinsley, J. M., Fairclough, R. J., Storer, R., Wilkes, F. J., Potter, A. C., Squire, S. E., Powell, D. S., Cozzoli, A., Capogrosso, R. F., Lambert, A. et al. (2011) Daily Treatment with SMTC1100, a Novel Small Molecule Utrophin Upregulator, Dramatically Reduces the Dystrophic Symptoms in the mdx Mouse. *PLoS One*, 6, e19189.
35. Smith, F. J. D., Eady, R. A. J., Leigh, I. M., McMillan, J. R., Rugg, E. L., Kelsell, D. P., Bryant, S. P., Spurr, N. K., Geddes, J. F., Kirtschig, G. et al. (1996) Plectin deficiency results in muscular dystrophy with epidermolysis bullosa. *Nature Genet.*, 13, 450-457.
36. Andrä, K., Lassmann, H., Bittner, R., Shorny, S., Fässler, R., Propst, F. and Wiche, G. (1997) Targeted inactivation of plectin reveals essential function in maintaining the integrity of skin, muscle, and heart cytoarchitecture. *Genes & Dev.*, 11, 3143-3156.
37. Pulkkinen, L., Smith, F. J. D., Shimizu, H., Murata, S., Yaoita, H., Hachisuka, H., Nishikawa, T., McLean, W. H. I. and Uitto, J. (1996) Homozygous Deletion Mutations in the Plectin Gene (PLEC1) in Patients with Epidermolysis Bullosa Simplex Associated with Late-Onset Muscular Dystrophy. *Human Molecular Genetics*, 5, 1539-1546.
38. Schröder, R., Mundegar, R., Treusch, M., Schlegel, U., Blümcke, I., Owaribe, K. and Magin, T. (1997) Altered distribution of plectin/HD1 in dystrophinopathies. *Eur J Cell Biol.*, 74, 165-171.
39. Gundesli, H., Talim, B., Korkusuz, P., Balci-Hayta, B., Cirak, S., Akarsu, N. A., Topaloglu, H. and Dincer, P. (2010) Mutation in Exon 1f of PLEC, Leading to Disruption of Plectin Isoform 1f, Causes Autosomal-Recessive Limb-Girdle Muscular Dystrophy. *Am. J. Hum. Genet.*, 87, 834-841.
40. Hu, H., Columbus, J., Zhang, Y., Wu, D., Lian, L., Yang, S., Goodwin, J., Luczak, C., Carter, M., Chen, L. et al. (2004) A map of WW domain family interactions. *PROTEOMICS*, 4, 643-655.
41. Otte, L., Wiedemann, U., Schlegel, B., Pires, J. R., Beyermann, M., Schmieder, P., Krause, G., Volkmer-Engert, R., Schneider-Mergener, J. and Oschkinat, H. (2003) WW domain sequence activity relationships identified using ligand recognition propensities of 42 WW domains. *Protein Science*, 12, 491-500.
42. McArthur, T. and Ohtoshi, A. (2007) A Brain-Specific Homeobox Gene, Bsx, Is Essential for Proper Postnatal Growth and Nursing. *Mol. Cell. Biol.*, 27, 5120-5127.
43. Foster, H., Sharp, P. S., Athanasopoulos, T., Trollet, C., Graham, I. R., Foster, K., Wells, D. J. and Dickson, G. (2008) Codon and mRNA Sequence Optimization of Microdystrophin Transgenes Improves Expression and Physiological Outcome in Dystrophic mdx Mice Following AAV2/8 Gene Transfer. *Mol Ther*, 16, 1825-1832.
44. Thompson, O., Kleino, I., Crimaldi, L., Gimona, M., Saksela, K. and Winder, S. J. (2008) Dystroglycan, Tks5 and Src mediated assembly of podosomes in myoblasts. *PLoS One*, 3, e3638.
45. Thompson, O., Moore, C. J., Hussain, S.-A., Kleino, I., Peckham, M., Hohenester, E., Ayscough, K. R., Saksela, K. and Winder, S. J. (2010) Modulation of cell spreading and cell-substrate adhesion dynamics by dystroglycan. *J. Cell Sci.*, 123, 118-127.
46. Bassett, D. I., Bryson-Richardson, R. J., Daggett, D. F., Gautier, P., Keenan, D. G. and Currie, P. D. (2003) Dystrophin is required for the formation of stable muscle attachments in the zebrafish embryo. *Development*, 130, 5851-5860.
47. Bassett, D. I. and Currie, P. D. (2003) The zebrafish as a model for muscular dystrophy and congenital myopathy. *Hum. Mol. Genet.*, 12, R265-270.
48. Miller, G., Moore, C. J., Terry, R., Riviere, T. L., Mitchell, A., Piggott, R., Lipscomb, L., Dear, T. N., Wells, D. J. and Winder, S. J. (Submitted) Preventing dystroglycan tyrosine phosphorylation ameliorates the dystrophic phenotype in mdx mouse.
49. Luo, F. R., Yang, Z., Camuso, A., Smykla, R., McGlinchey, K., Fager, K., Flefleh, C., Castaneda, S., Inigo, I., Kan, D. et al. (2006) Dasatinib (BMS-354825) Pharmacokinetics and Pharmacodynamic Biomarkers in Animal Models Predict Optimal Clinical Exposure. *Clinical Cancer Research*, 12, 7180-7186.
50. Green, T. P., Fennell, M., Whittaker, R., Curwen, J., Jacobs, V., Allen, J., Logie, A., Hargreaves, J., Hickinson, D. M., Wilkinson, R. W. et al. (2009) Preclinical anticancer activity of the potent, oral Src inhibitor AZD0530. *Molecular Oncology*, 3, 248-261.
51. Yang, Y., Kitagaki, J., Dai, R.-M., Tsai, Y. C., Lorick, K. L., Ludwig, R. L., Pierre, S. A., Jensen, J. P., Davydov, I. V., Oberoi, P. et al. (2007) Inhibitors of Ubiquitin-Activating Enzyme (E1), a New Class of Potential Cancer Therapeutics. *Cancer Research*, 67, 9472-9481.

What is claimed is:

1. A method of treating muscular dystrophy and/or inhibiting degradation of β-dystroglycan in a subject in need thereof, the method comprising a step of administering to the subject a therapeutically effective amount of at least one compound selected from the group consisting of dasatinib, bosutinib, saracatinib, and Pyr-41.

2. The method according to claim 1, further comprising a step of administering to the subject a therapeutically effective amount of a compound selected from the group consisting of carfilzomib, MG132, MG-115, ALLN, and bortezomib.

3. The method according to claim 1, wherein the subject is in need of treatment for muscular dystrophy selected from the group consisting of Duchenne Muscular Dystrophy, Limb Girdle Muscular Dystrophy, Congenital Muscular Dystrophy and Becker Muscular Dystrophy.

4. The method according to claim 3, wherein the subject is in need of treatment for Limb Girdle Muscular Dystrophy selected from the group consisting of Limb Girdle Muscular Dystrophy 2C, Limb Girdle Muscular Dystrophy 2D, Limb Girdle Muscular Dystrophy 2E, and Limb Girdle Muscular Dystrophy 2F.

5. The method according to claim 3, wherein the subject is in need of treatment for Congenital Muscular Dystrophy selected from the group consisting of MDC1A, MDC1B, MDC1D, Fukuyama CMD (FCMD), Muscle eye brain disease (MEB) and Walker Warburg Syndrome (WWS).

6. The method according to claim 1, wherein the subject is in need of treatment for a symptom selected from the group consisting of muscle weakness or degeneration, calf hypertrophy, reduced myofibre integrity, elevated serum creatine kinase levels, loss of dystrophin and dystrophin associated proteins, and central nucleation of muscle fibres.

7. The method according to claim 1, wherein the step of administering includes administering an antibody that specifically binds to a PPxY domain of a wildtype β-dystroglycan polypeptide, and wherein the tyrosine amino acid of the PPxY domain is unphosphorylated.

8. A method for inhibiting degradation of β-dystroglycan, the method comprising a step of exposing at least one cell comprising β-dystroglycan to at least one compound selected from the group consisting of dasatinib, bosutinib, saracatinib, and Pyr-41.

9. The method according to claim 8, further comprising a step of exposing the at least one cell comprising β-dystroglycan to a compound selected from the group consisting of carfilzomib, MG132, MG-115, ALLN, and bortezomib.

* * * * *